US007947456B2

(12) United States Patent
Khurana et al.

(10) Patent No.: US 7,947,456 B2
(45) Date of Patent: *May 24, 2011

(54) ASSESSING BRAIN ANEURYSMS

(75) Inventors: Gautam Khurana, Forrest (AU); Fredric B. Meyer, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.
This patent is subject to a terminal disclaimer.

(21) Appl. No.: 12/716,098

(22) Filed: Mar. 2, 2010

(65) Prior Publication Data

US 2010/0158811 A1 Jun. 24, 2010

Related U.S. Application Data

(63) Continuation of application No. 11/912,540, filed as application No. PCT/US2005/014868 on Apr. 29, 2005, now Pat. No. 7,709,204.

(51) Int. Cl.
*C12Q 1/68* (2006.01)

(52) U.S. Cl. ........................................................ 435/6

(58) Field of Classification Search ........................ None
See application file for complete search history.

(56) References Cited

U.S. PATENT DOCUMENTS 7,709,204 B2 * 5/2010 Khurana et al. .................. 435/6

FOREIGN PATENT DOCUMENTS

WO WO 99/57318 11/1999

OTHER PUBLICATIONS

International Preliminary Report on Patentability for PCT/US2005/014868 (Mar. 19, 2009), 5 pages.
GenBank Accession No. AF519768 dated Jul. 9, 2002, 18 pages.
GenBank Single Nucleotide Polymorphism Database No. rs3918201 revised May 25, 2006, 2 pages.
GenBank Single Nucleotide Polymorphism Database No. rs1007311 revised May 25, 2006, 2 pages.
GenBank Single Nucleotide Polymorphism Database No. rs1008140 revised May 25, 2006, 2 pages.
GenBank Single Nucleotide Polymorphism Database No. rs10255980 revised May 25, 2006, 2 pages.
GenBank Single Nucleotide Polymorphism Database No. rs10531586 revised May 25, 2006, 2 pages.
GenBank Single Nucleotide Polymorphism Database No. rs10539415 revised May 25, 2006, 2 pages.
GenBank Single Nucleotide Polymorphism Database No. rs10539416 revised May 25, 2006, 2 pages.
GenBank Single Nucleotide Polymorphism Database No. rs10595051 revised May 25, 2006, 2 pages.
GenBank Single Nucleotide Polymorphism Database No. rs1065300 revised May 25, 2006, 2 pages.
GenBank Single Nucleotide Polymorphism Database No. rs10952298 revised May 25, 2006, 2 pages.
GenBank Single Nucleotide Polymorphism Database No. rs11371169 revised May 25, 2006, 2 pages.
GenBank Single Nucleotide Polymorphism Database No. rs11771443 revised May 25, 2006, 2 pages.
GenBank Single Nucleotide Polymorphism Database No. rs11974098 revised May 25, 2006, 2 pages.
GenBank Single Nucleotide Polymorphism Database No. rs12937 revised May 25, 2006, 2 pages.
GenBank Single Nucleotide Polymorphism Database No. rs13305982 revised May 25, 2006, 2 pages.
GenBank Single Nucleotide Polymorphism Database No. rs13305984 revised May 25, 2006, 2 pages.
GenBank Single Nucleotide Polymorphism Database No. rs13305985 revised May 25, 2006, 2 pages.
GenBank Single Nucleotide Polymorphism Database No. rs13310763 revised May 25, 2006, 2 pages.
GenBank Single Nucleotide Polymorphism Database No. rs13310774 revised May 25, 2006, 2 pages.
GenBank Single Nucleotide Polymorphism Database No. rs13310854 revised May 25, 2006, 2 pages.
GenBank Single Nucleotide Polymorphism Database No. rs13311166 revised May 25, 2006, 2 pages.
GenBank Single Nucleotide Polymorphism Database No. rs13311313 revised May 25, 2006, 2 pages.
GenBank Single Nucleotide Polymorphism Database No. rs13420 revised May 25, 2006, 2 pages.
GenBank Single Nucleotide Polymorphism Database No. rs1541861 revised May 25, 2006, 2 pages.
GenBank Single Nucleotide Polymorphism Database No. rs1799983 revised May 25, 2006, 3 pages.
GenBank Single Nucleotide Polymorphism Database No. rs1799984 revised May 25, 2006, 2 pages.
GenBank Single Nucleotide Polymorphism Database No. rs1799985 revised May 25, 2006, 2 pages.
GenBank Single Nucleotide Polymorphism Database No. rs1800779 revised May 25, 2006, 2 pages.
GenBank Single Nucleotide Polymorphism Database No. rs1800780 revised May 25, 2006, 14 pages.
GenBank Single Nucleotide Polymorphism Database No. rs1800781 revised May 25, 2006, 2 pages.
GenBank Single Nucleotide Polymorphism Database No. rs1800782 revised May 25, 2006, 2 pages.
GenBank Single Nucleotide Polymorphism Database No. rs1800783 revised May 25, 2006, 2 pages.
GenBank Single Nucleotide Polymorphism Database No. rs1808593 revised May 25, 2006, 3 pages.
GenBank Single Nucleotide Polymorphism Database No. rs2070744 revised May 25, 2006, 3 pages.
GenBank Single Nucleotide Polymorphism Database No. rs2243310 revised May 25, 2006, 2 pages.
GenBank Single Nucleotide Polymorphism Database No. rs2243311 revised May 25, 2006, 2 pages.
GenBank Single Nucleotide Polymorphism Database No. rs2256314 revised May 25, 2006, 2 pages.

(Continued)

*Primary Examiner* — James Martinell
(74) *Attorney, Agent, or Firm* — Fish & Richardson P.C.

(57) ABSTRACT

This document provides methods and materials related to assessing brain conditions within mammals. For example, methods and materials that can be used to determine whether or not a mammal (e.g., a human) with a brain aneurysm is likely to experience brain aneurysm rupture are provided.

20 Claims, 19 Drawing Sheets

OTHER PUBLICATIONS

GenBank Single Nucleotide Polymorphism Database No. rs2566506 revised May 25, 2006, 2 pages.
GenBank Single Nucleotide Polymorphism Database No. rs2566507 revised May 25, 2006, 2 pages.
GenBank Single Nucleotide Polymorphism Database No. rs2566508 revised May 25, 2006, 2 pages.
GenBank Single Nucleotide Polymorphism Database No. rs2566509 revised May 25, 2006, 2 pages.
GenBank Single Nucleotide Polymorphism Database No. rs2566510 revised May 25, 2006, 2 pages.
GenBank Single Nucleotide Polymorphism Database No. rs2566511 revised May 25, 2006, 2 pages.
GenBank Single Nucleotide Polymorphism Database No. rs2566512 revised May 25, 2006, 2 pages.
GenBank Single Nucleotide Polymorphism Database No. rs2566513 revised May 25, 2006, 2 pages.
GenBank Single Nucleotide Polymorphism Database No. rs2566515 revised May 25, 2006, 2 pages.
GenBank Single Nucleotide Polymorphism Database No. rs2566516 revised May 25, 2006, 2 pages.
GenBank Single Nucleotide Polymorphism Database No. rs2566517 revised May 25, 2006, 2 pages.
GenBank Single Nucleotide Polymorphism Database No. rs2566518 revised May 25, 2006, 2 pages.
GenBank Single Nucleotide Polymorphism Database No. rs2566519 revised May 25, 2006, 2 pages.
GenBank Single Nucleotide Polymorphism Database No. rs2853791 revised May 25, 2006, 2 pages.
GenBank Single Nucleotide Polymorphism Database No. rs2853792 revised May 25, 2006, 2 pages.
GenBank Single Nucleotide Polymorphism Database No. rs2853793 revised May 25, 2006, 2 pages.
GenBank Single Nucleotide Polymorphism Database No. rs2853794 revised May 25, 2006, 2 pages.
GenBank Single Nucleotide Polymorphism Database No. rs2853795 revised May 25, 2006, 2 pages.
GenBank Single Nucleotide Polymorphism Database No. rs2853796 revised May 25, 2006, 2 pages.
GenBank Single Nucleotide Polymorphism Database No. rs2853797 revised May 25, 2006, 2 pages.
GenBank Single Nucleotide Polymorphism Database No. rs2853798 revised May 25, 2006, 2 pages.
GenBank Single Nucleotide Polymorphism Database No. rs285380 revised May 25, 2006, 2 pages.
GenBank Single Nucleotide Polymorphism Database No. rs3134740 revised May 25, 2006, 2 pages.
GenBank Single Nucleotide Polymorphism Database No. rs3729625 revised May 25, 2006, 2 pages.
GenBank Single Nucleotide Polymorphism Database No. rs3730001 revised May 25, 2006, 2 pages.
GenBank Single Nucleotide Polymorphism Database No. rs3730002 revised May 25, 2006, 2 pages.
GenBank Single Nucleotide Polymorphism Database No. rs3730003 revised May 25, 2006, 2 pages.
GenBank Single Nucleotide Polymorphism Database No. rs3730006 revised May 25, 2006, 2 pages.
GenBank Single Nucleotide Polymorphism Database No. rs3730007 revised May 25, 2006, 2 pages.
GenBank Single Nucleotide Polymorphism Database No. rs3730009 revised May 25, 2006, 2 pages.
GenBank Single Nucleotide Polymorphism Database No. rs3730010 revised May 25, 2006, 2 pages.
GenBank Single Nucleotide Polymorphism Database No. rs3730012 revised May 25, 2006, 2 pages.
GenBank Single Nucleotide Polymorphism Database No. rs3730305 revised May 25, 2006, 2 pages.
GenBank Single Nucleotide Polymorphism Database No. rs3730306 revised May 25, 2005, 2 pages.
GenBank Single Nucleotide Polymorphism Database No. rs3793341 revised May 25, 2006, 2 pages.
GenBank Single Nucleotide Polymorphism Database No. rs3793342 revised May 25, 2006, 2 pages.
GenBank Single Nucleotide Polymorphism Database No. rs3828997 revised May 25, 2006, 2 pages.
GenBank Single Nucleotide Polymorphism Database No. rs3834873 revised May 25, 2006, 2 pages.
GenBank Single Nucleotide Polymorphism Database No. rs3918155 revised May 25, 2006, 2 pages.
GenBank Single Nucleotide Polymorphism Database No. rs3918156 revised May 25, 2006, 2 pages.
GenBank Single Nucleotide Polymorphism Database No. rs3918157 revised May 25, 2006, 2 pages.
GenBank Single Nucleotide Polymorphism Database No. rs3918158 revised May 25, 2006, 2 pages.
GenBank Single Nucleotide Polymorphism Database No. rs3918159 revised May 25, 2006, 2 pages.
GenBank Single Nucleotide Polymorphism Database No. rs3918160 revised May 25, 2006, 2 pages.
GenBank Single Nucleotide Polymorphism Database No. rs3918161 revised May 25, 2006, 2 pages.
GenBank Single Nucleotide Polymorphism Database No. rs3918162 revised May 25, 2006, 2 pages.
GenBank Single Nucleotide Polymorphism Database No. rs3918163 revised May 25, 2006, 2 pages.
GenBank Single Nucleotide Polymorphism Database No. rs3918164 revised May 25, 2006, 2 pages.
GenBank Single Nucleotide Polymorphism Database No. rs3918165 revised May 25, 2006, 2 pages.
GenBank Single Nucleotide Polymorphism Database No. rs3918166 revised May 25, 2006, 2 pages.
GenBank Single Nucleotide Polymorphism Database No. rs3918167 revised May 25, 2006, 2 pages.
GenBank Single Nucleotide Polymorphism Database No. rs3918168 revised May 25, 2006, 2 pages.
GenBank Single Nucleotide Polymorphism Database No. rs3918169 revised May 25, 2006, 2 pages.
GenBank Single Nucleotide Polymorphism Database No. rs3918170 revised May 25, 2006, 2 pages.
GenBank Single Nucleotide Polymorphism Database No. rs3918173 revised May 25, 2006, 2 pages.
GenBank Single Nucleotide Polymorphism Database No. rs3918174 revised May 25, 2006, 2 pages.
GenBank Single Nucleotide Polymorphism Database No. rs3918175 revised May 25, 2006, 2 pages.
GenBank Single Nucleotide Polymorphism Database No. rs3918176 revised May 25, 2006, 2 pages.
GenBank Single Nucleotide Polymorphism Database No. rs3918177 revised May 25, 2006, 2 pages.
GenBank Single Nucleotide Polymorphism Database No. rs3918178 revised May 25, 2006, 2 pages.
GenBank Single Nucleotide Polymorphism Database No. rs3918179 revised May 25, 2006, 2 pages.
GenBank Single Nucleotide Polymorphism Database No. rs3918180 revised May 25, 2006, 2 pages.
GenBank Single Nucleotide Polymorphism Database No. rs3918181 revised May 25, 2006, 2 pages.
GenBank Single Nucleotide Polymorphism Database No. rs3918182 revised May 25, 2006, 2 pages.
GenBank Single Nucleotide Polymorphism Database No. rs3918183 revised May 25, 2006, 2 pages.
GenBank Single Nucleotide Polymorphism Database No. rs3918184 revised May 25, 2006, 2 pages.
GenBank Single Nucleotide Polymorphism Database No. rs3918185 revised May 25, 2006, 2 pages.
GenBank Single Nucleotide Polymorphism Database No. rs3918187 revised May 25, 2006, 2 pages.
GenBank Single Nucleotide Polymorphism Database No. rs3918188 revised May 25, 2006, 3 pages.
GenBank Single Nucleotide Polymorphism Database No. rs3918189 revised May 25, 2006, 2 pages.
GenBank Single Nucleotide Polymorphism Database No. rs3918190 revised May 25, 2006, 2 pages.
GenBank Single Nucleotide Polymorphism Database No. rs3918191 revised May 25, 2006, 2 pages.

GenBank Single Nucleotide Polymorphism Database No. rs3918192 revised May 25, 2006, 2 pages.
GenBank Single Nucleotide Polymorphism Database No. rs3918193 revised May 25, 2006, 2 pages.
GenBank Single Nucleotide Polymorphism Database No. rs3918194 revised May 25, 2006, 2 pages.
GenBank Single Nucleotide Polymorphism Database No. rs3918195 revised May 25, 2006, 2 pages.
GenBank Single Nucleotide Polymorphism Database No. rs3918196 revised May 25, 2006, 2 pages.
GenBank Single Nucleotide Polymorphism Database No. rs3918197 revised May 25, 2006, 2 pages.
GenBank Single Nucleotide Polymorphism Database No. rs3918198 revised May 25, 2006, 2 pages.
GenBank Single Nucleotide Polymorphism Database No. rs3918199 revised May 25, 2006, 2 pages.
GenBank Single Nucleotide Polymorphism Database No. rs3918200 revised May 25, 2006, 2 pages.
GenBank Single Nucleotide Polymorphism Database No. rs3918202 revised May 25, 2006, 2 pages.
GenBank Single Nucleotide Polymorphism Database No. rs3918203 revised May 25, 2006, 2 pages.
GenBank Single Nucleotide Polymorphism Database No. rs3918204 revised May 25, 2006, 2 pages.
GenBank Single Nucleotide Polymorphism Database No. rs3918205 revised May 25, 2006, 2 pages.
GenBank Single Nucleotide Polymorphism Database No. rs3918207 revised May 25, 2006, 2 pages.
GenBank Single Nucleotide Polymorphism Database No. rs3918208 revised May 25, 2006, 2 pages.
GenBank Single Nucleotide Polymorphism Database No. rs3918209 revised May 25, 2006, 2 pages.
GenBank Single Nucleotide Polymorphism Database No. rs3918210 revised May 25, 2006, 2 pages.
GenBank Single Nucleotide Polymorphism Database No. rs3918225 revised May 25, 2006, 2 pages.
GenBank Single Nucleotide Polymorphism Database No. rs3918226 revised May 25, 2006, 2 pages.
GenBank Single Nucleotide Polymorphism Database No. rs3918227 revised May 25, 2006, 2 pages.
GenBank Single Nucleotide Polymorphism Database No. rs3918228 revised May 25, 2006, 2 pages.
GenBank Single Nucleotide Polymorphism Database No. rs3918229 revised May 25, 2006, 2 pages.
GenBank Single Nucleotide Polymorphism Database No. rs3918230 revised May 25, 2006, 2 pages.
GenBank Single Nucleotide Polymorphism Database No. rs3918231 revised May 25, 2006, 2 pages.
GenBank Single Nucleotide Polymorphism Database No. rs3918232 revised May 25, 2006, 2 pages.
GenBank Single Nucleotide Polymorphism Database No. rs3918235 revised May 25, 2006, 2 pages.
GenBank Single Nucleotide Polymorphism Database No. rs3918236 revised May 25, 2006, 2 pages.
GenBank Single Nucleotide Polymorphism Database No. rs3918237 revised May 25, 2006, 2 pages.
GenBank Single Nucleotide Polymorphism Database No. rs4725985 revised May 25, 2006, 2 pages.
GenBank Single Nucleotide Polymorphism Database No. rs6947833 revised May 25, 2006, 2 pages.
GenBank Single Nucleotide Polymorphism Database No. rs6969597 revised May 25, 2006, 2 pages.
GenBank Single Nucleotide Polymorphism Database No. rs743506 revised May 25, 2006, 2 pages.
GenBank Single Nucleotide Polymorphism Database No. rs743507 revised May 25, 2006, 3 pages.
GenBank Single Nucleotide Polymorphism Database No. rs753482 revised May 25, 2006, 2 pages.
GenBank Single Nucleotide Polymorphism Database No. rs7776461 revised May 25, 2006, 2 pages.
GenBank Single Nucleotide Polymorphism Database No. rs7792133 revised May 25, 2006, 2 pages.
GenBank Single Nucleotide Polymorphism Database No. rs7830 revised May 25, 2006, 3 pages.
GenBank Single Nucleotide Polymorphism Database No. rs867225 revised May 25, 2006, 2 pages.
GenBank Single Nucleotide Polymorphism Database No. rs891511 revised May 25, 2006, 2 pages.
GenBank Single Nucleotide Polymorphism Database No. rs891512 revised May 25, 2006, 3 pages.
GenBank Single Nucleotide Polymorphism Database No. rs933163 revised May 25, 2006, 2 pages.
Abecasis and Cookson, "GOLD—Graphical Overview of Linkage Disequilibrium," 2000, 16(2):182-183 *Bioinformatics*, 2000, 16(2):182-183
Ardlie et al., "Patterns of linkage disequilibrium in the human genome," 3:299-309 *Nat. Rev. Genet.*, 2002, 3:299-309
Inagawa and Hirano, "Autopsy Study of Unruptured Incidental Intracranial Aneurysms," *Surg. Neurol.*, 1990, 34:361-365.
Khurana et al., "Update on genetic evidence for rupture-prone compared with rupture-resistant intracranial saccural aneurysms," *Neurosurg. Focus*, 2004, 17(5):E7-E22.
Khurana et al., "Endothelial Nitric Oxide Synthase T-786C Single Nucleotide Polymorphism. A Putative Genetic Marker Differentiating Small Versus Large Ruptured Intracranial Aneurysms," *Stroke*, 2003, 34:2555-2559.
Khurana et al., "Endothelial nitric oxide synthase gene polymorphisms predict susceptabilty to aneurysmal subarachnoid hemorrhage and cerebral vasospasm," *J. Cerebral Blood Flow Metabol.*, 2004, 24:291-297.
Khurana et al., "The presence of tandem *endothelial nitric oxide synthase* gene polymorphisms identifying brain aneurysms more prone to rupture," *J. Neurosurg.*, 2005, 102:526-531.
Lake et al., "Estimation and Tests of Haplotype-Environment Interaction when Linkage Phase Is Ambiguous," *Hum. Hered.*, 2003, 55:56-65.
Myakishev et al., "High-Throughput SNP Genotyping by Allele-Specific PCR with Universal Energy-Transfer-Labeled Primers," *Genome Res.*, 2001, 11:163-169.
Nakayama et al., "T-$^{786}$→C Mutation in the 5'-Flanking Region of the Endothelial Nitric Oxide Synthase Gene Is Associated With Coronary Spasm," *Circulation*, 1999, 99:2864-2870.
Prince et al., "Robust and Accurate Single Nucleotide Polymorphism Genotyping by Dynamic Allele-Specific Hybridization (DASH): Design Criteria and Assay Validation," *Genome Res.*, 2001, 11:152-162.
Schafer and Hawkins, "DNA variation and the future of human genetics," *Nat. Biotechnol.*, 1998, 16:33-39.
Schaid et al., "Score Tests for Association between Traits and Haplotypes when Linkage Phase Is Ambiguous," *Am. J. Hum. Genet.*, 2002, 70:425-434.
Schievink, "Intracranial Aneurysms," N. Engl. J. Med., 1997, 336:28-40.
Sohni et al., "Microfluidic chip-based method for genotyping microsatellites, VNTRs and insertion/deletion polymorphisms," *Clin. Biochem.*, 2003, 36:35-39.
Sohni et al., "Active Electronic Arrays for Genotyping of *NAT2* Polymorphisms," *Clin. Chem.*, 2001, 47(10):1922-1924.
Song et al., "Genotype-specific Influence on Nitric Oxide Synthase Gene Expression, Protein Concentrations, and Enzyme Activity in Cultured Human Endothelial Cells" 2003, 49:847-852.
Stoneking et al., "Population Variation of Human mtDNA Control Region Sequences Detected by Enzymatic Amplification and Sequence-specific Oligonucleotide Probes," *Am. J. Hum. Genet.*, 1991, 48:370-382.
Underhill et al., "Detection of Numerous Y Chromosome Biallelic Polymorphisms by Denaturing High-Performance Liquid Chromatography," *Genome Res.*, 1997, 7:996-1005.
Wattanapitayakul et al., "Therapeutic implications of human endothelial nitric oxide synthase gene polymorphism," *Trends Pharmacol. Sci.*, 2001, 22(7):361-368.

* cited by examiner

Figure 2

1 gtggtgggta cctgtaatct cagctactca ggaggctggg tcaggagaat cgcttgaacc
61 caggaggcgg aggttacagt gagctgagat agcaccattg cattccagcc tggacaacaa
121 aagcgagact ctgtctcaaa aaaaaaaaaa aattagccag gcgtggtggt gggtgcctgt
181 cgtcctcggg aggctgaggc atgagaatca ctccgggagg cagaggttgc aatgaaccaa
241 gatcacacca ctgcactcca gcctgggtga cagagcaaga ctctgtctaa aaaaaaaaaa
301 aagacagaag gatgtcagca tctgatgctg cctgtcacct tgaccctgag gatgccagtc
361 acagctccat taactgggac ctaggaaaat gagtcatcct tggtcatgca catttcaaat
421 ggtggcttaa tatggaagcc agacttgggt tctgttgtct cctccagcat ggtagaagat
481 gcctgaaaag taggggctgg atcccatccc ctgcctcact gggaaggcga ggtggtgggg
541 tggggtgggg cctcaggctt ggggtcatgg gacaaagccc aggctgaatg ccgcccttcc
601 atctccctcc tcctgagaca ggggcagcag ggcacactag tgtccaggag cagcttatga
661 ggccccttca ccctccatcc tccaaaactg gcagacccca ccttcttggt gtgaccccag
721 agctctgagc acagcccgtt ccttccgcct gccggccccc cacccaggcc caccccaacc
781 ttatcctcca ctgcttttca gaggagtctg gccaacacaa atcctcttgt ttgtttgtct
841 gtctgtctgc tgctcctagt ctctgcctct cccagtctct cagcttccgt ttctttctta
901 aactttctct cagtctctga ggtctcgaaa tcacgaggct tcgacccctg tggaccagat
961 gcccagctag tggcctttct ccagcccctc agatgacaca gaactacaaa ccccagcatg
1021 cactctggcc tgaagtgcct ggagagtgct ggtgtacccc acctgcattc tgggaactgt
1081 agtttcccta gtcccccatg ctcccaccag ggcatcaagc tcttccctgg ctggctgacc
1141 ctgcctcagc cctagtctct ctgctgacct gcggccccgg gaagcgtgcg tcactgaatg
1201 acagggtggg ggtggaggca ctggaaggca gcttcctgct cttttgtgtc ccccacttga
1261 gtcatggggg tgtgggggtt ccaggaaatt ggggctggga ggggaaggga taccctaatg
1321 tcagactcaa ggacaaaaag tcactacatc cttgctgggc ctctatcccc aagaacccaa
1381 aaggactcaa gggtggggat ccaggagttc ttgtatgtat gggggaggt gaaggagaga
1441 acctgcatga ccctagaggt ccctgtggtc actgagagtg tgggctgcca tcccctgcta
1501 cagaaacggt gctcaccttc tgcccaaccc tccagggaaa ggcacacagg ggtgaggccg
1561 aaggcccttc cgtctggtgc cacatcacag aaggaccttt atgacccccct ggtggctcta
1621 ccctgccact ccccaatgcc ccagccccca tgctgcagcc ccagggctct gctggacacc
1681 tgggctccca cttatcagcc tcagtcctca cagcggaacc caggcgtccg gccccccacc
1741 cttcaggcca gcgggcgtgg agctgaggct ttagagcctc ccagccgggc ttgttcctgt
1801 cccattgtgt atgggatagg ggcggggcga gggccagcac tggagagccc cctcccactg
1861 ccccctcctc tcggtcccct ccctcttcct aaggaaaagg ccagggctct gctggagcag
1921 gcagcagagt ggacgcacag taacatgggc aacttgaaga gcgtggccca ggagcctggg
1981 ccaccctgcg gcctggggct ggggctgggc cttgggctgt gcggcaagca gggcccagcc
2041 accccggccc ctgagcccag ccgggcccca gcatccctac tcccaccagc gccagaacac
2101 aggtaagggc caggcagcta ggagcaggtg ggcaacaagg gtggtgtcaa ggcctgaagc
2161 ctggggctgg gaaggtctgg aacttgtagc tgagtcggga gggccaggtc acaaatgcaa
2221 aagggctatt aatgtgcata gaacaggaca gtctgggagg ctcagaaagg agaccaggat
2281 cagagtcggc aggtgaaagc tgggagtaag ggtgccagct atagaatctg gccagggttt
2341 gaatgctgct ctgccgccag gagctgtttg actttgagca agttacttaa tctctctgaa
2401 cctccattta tataaaacga gatatggcaa tacttactcc atggggaagt aagtttctag
2461 ctcacagcaa gccttcaaca gcagcgatga ttatttagct ggagaagaaa ggagctgaca
2521 gcagtggtta caggagtgag aaagtggggt ctcccagaag agggagagag ttgggcagga
2581 aactcgggcc cttggggtaa gcaggctgag aagacagagc caccaggctt ttttcccctg
2641 ctccagcccc ctctcctcgt ggctgtcacc cgaaaactgg accatgcagt tcccacaaga
2701 gtcctcccgg gggtagaggt cccaggaggg aggaaagacc cggaggcctg gtggggtgcc
2761 aggccggggg caggctgggg ctgcaggcag ctatgcaggg aaggctgagg gccgggggccc
2821 tgctgctcag gcgcaccctt ggcctgagtc cctcccttcc tccctgccgc tggtggctct
2881 gggaggaagt gataaggcct gcgaggcttc ccttcacaca tggggctgct gtcaggaggg
2941 gttgtgagtg cggagggaaa tcagagctga ggaatccctg cagggcttcc ctccactcaa
3001 gcaccaggct ctgtccccct cagggtaggg cttatagcag ctttgcgggg ggtggacacc
3061 ccatctccag aagaggtgag gtgggcgctg caggtgggat gcgaacttag cctcgggtca
3121 ggggctcagg agctcagcac cagcagcccc tgcagcccag gaccctggtc tataaacgga
3181 ggcacagctc gcctctagct cctaaggcat ggggaacgcc agaaggcatg cggcaggtgg
3241 gctgtgagat cgccagtgct gtaacagggg cctccgggtg acatctggga aggctgaaag
3301 gaaacaaacc cttcctgatg accctatccc tggctcccaa cagcccccccg agctccccgc
3361 taacccagcc cccagagggg cccaagttcc ctcgtgtgaa gaactgggag gtggggagca
3421 tcacctatga caccctcagc gcccaggcgc agcaggtaag gccggcatgc cctgtcccca

Figure 2 (continued)

```
3481 tcgtctccag ggaaagggtg ggtaaggcct ggcctcagat ggggccggag agggaagctc
3541 aacccttctt tgaattggtc ccttgtttcc aaaaagagga gaggactggg aagaaccaga
3601 ggagttgagg gacatgcacg ggacttgggt gaccctcagc ctccagcctt acccccaacc
3661 ctggctcaaa ctctccccca tcccacccct gcaccccttt ccccccctccc acccctgcac
3721 ccttcctccc tctcccccccg tcccctgcct gcattcctcc tccctctccc catctcaccc
3781 ctgcacccct cttccctctc ccacccctgc acccctcctc cctctccccg tcccacccctg
3841 cactcccgcc ctctccagcg tcccacccct acacccctcc tccctctgcc ccattccacc
3901 cctgcacccc ctcctccctc tgccccgacc cacccctgca cccctcctcc ctctcccccg
3961 tcccacccct gcatccctcc tccctctgcc ccgtcccacc cctacacccc tcctccctct
4021 cccccatccc accccctaaac ccctcctccc tctcccctgt cccatccctg caccccttcct
4081 ccctctcccc gtcccatccc tgcaccccttc ctccctctcc ccgtcccatc cctgcacccc
4141 tcctccctct gctcccatcc caccccctgca cccctcctcc ctctgcccct accccacctc
4201 tgcacccctc ctccttctcc ccatcccacc cctgcacccc tcctccctct gcccctaccc
4261 caccccctgca cccctcctcc ttctccccat cccacctctg caccccctcct ccctctcccc
4321 tctcccaccc ctgtacccctt cctccttctc cccgtcccac ccctgcactt ctcctccctc
4381 tcacccatcc caccccctgca cccttcttcc ctctccccca tcccaccact gcacccctcc
4441 tccctctccc cctgttccac ccctgcaccc ctcctccctg cccccaactc ccatcccacc
4501 cctgcacccct ggcctgtcct gacctttgca ctccctcgac ccaggatggg ccctgcaccc
4561 caagacgctg cctgggctcc ctggtatttc cacggaaact acagggccgg ccctcccccg
4621 gcccccccggc ccctgagcag ctgctgagtc aggcccggga cttcatcaac cagtactaca
4681 gctccattaa gaggtgacag cttcccggac gccacagcct cccttgtccc actgaggccc
4741 cagaaacccc gtgacgacct tcccatgacc ccctcccttc ccagatccta acaccacgtg
4801 ggcccctccc gccctccccc agcacttgca caaagcctgg aggagggcct ccctgtccca
4861 cacaacttcc tgcttgtccc cttcccaccc ctctcctccc caggagcggc tcccaggccc
4921 acgaacagcg gcttcaagag gtggaagccg aggtggcagc cacaggcacc taccagctta
4981 gggagagcga gctggtgttc ggggctaagc aggcctggcg caacgctccc cgctgcgtgg
5041 gccggatcca gtgggggaag ctgcaggtgc ggctggccag cgactgagag acccgggcgc
5101 taccaaaagg ggagcggggt ggcggggcag ttcctaaggc ttcccggggg ctgggaggtc
5161 ccaaactgtg ggggagatcc ttgccttttc ccttagagac tggaaaggta gggggactgc
5221 cccaccctca gcacccaggg gaacctcagc ccagtagtga agacctggtt atcaggccct
5281 atggtagtgc cttggctgga ggagggggaaa gaagtctaga cctgctgcag gggtgaggaa
5341 gtctagacct gctgcagggg tgaggaagtc tagacctgct gcaggggtga ggaagtctag
5401 acctgctgcg gggtgagga agtctagacc tgctgcgggg gtgaggacag ctgagcggag
5461 cttccctggg cggtgctgtc agtagcagga gcagcctcct ggaaaagccc tggctgctgc
5521 ttctccccca agagagaagg cttctcccgc caggccagtc cagtgcagcc cctcacccac
5581 acccactgct accccagttc ccctgcttcg gcccgcaccc tccctcacac cccagcccac
5641 agactcgggg ctggccttag ttactggaac gcctgtgacc acagcactaa gagaagcaag
5701 ctgccccatg gggacttgg tcccatggcc ttggcctcct tcaccatcac tggccgccaa
5761 agagtttgaa ataaagccac gtgcccagtg aatcccaaag gaacctcaac taaaataaaa
5821 acaatcctat ctgacacttg cctgaccctc taagtcattc aaagctttag ctcaacttcg
5881 atccatctga gctgccatag tggaccccac tcagagctgc gtccctccct tgaccccagg
5941 ttggtccctg ccactcccct gcccctgtca ctgacacatg tttcctcctc cctcaggcag
6001 gagtgggacc tcccagcctc ctcctggggc ctccactcag aatgtcagga tgagcagggt
6061 cctaggaggc ctctggtgca gccttccctt cccaccatcc atgtgctcaa agagaatcac
6121 ccgtcctttc ttgaatgcca tggatcatgg gggatttgct gcccacactc ctaggcggcc
6181 tcttagacat ccgttggtgc ctaacccaag catcagtttg gcagaggccg agtccctcct
6241 ctgtactgga taccaagtca gcttccatag ggatggggag acacctggcc cagggaggag
6301 atgagaagca gcccggatgg tgctacatat gtcagagagc agggcaggaa gggatcagtg
6361 tggctgccaa tggtcaggag ggcgccatgg agtgaaccat ggcccctgcc tcctcaccag
6421 cagctcctct ggagctgata ctcaagaccc cccgtctctc tcctcaccct cctctcccgc
6481 tgcctcggct ggctcaggtg ttcgatgccc gggactgcag gtctgcacag gaaatgttca
6541 cctacatctg caaccacatc aagtatgcca ccaaccgggg caaccttcgg tgagtgcccc
6601 ccaccatgcc aggccccagc cttcttcccc aaggcaggga aggcggggct ctgaccagct
6661 ctttccccat gcgtgccagc tcggccatca cagtgttccc gcagcgctgc cctggccgag
6721 gagacttccg aatctggaac agccagctgg tgcgctacgc gggctaccgg cagcaggacg
6781 gctctgtgcg gggggaccca gccaacgtgg agatcaccga ggtgggcacc gagggccacc
6841 catgagggtg tccccaaggt ggagaatgag gaaaccagtg ggagaaggct cgggggatcc
6901 aggcaggaag aggggagcct cggtgagata aaggatgaaa aacaccaaag gaggggtgcc
6961 tgggtggtca cggagaccca gccaatgagg gaccctggag atgaaggcag gagacagtgg
7021 atggaggggt ccctgaggag ggcatgaggc tcagccccag aaccccctct ggcccactcc
7081 ccacagctct gcattcagca cggctggacc ccaggaaacg gtcgcttcga cgtgctgccc
```

Figure 2 (Continued)

```
 7141 ctgctgctgc aggccccaga tgagccccca gaactcttcc ttctgccccc cgagctggtc
 7201 cttgaggtgc ccctggagca ccccacgtga gcaccaaagg gattgactgg gtgggatgga
 7261 gggggccatc cctgagcctc tcaagaaggg cctgcaaggg ggtgctgatc ccacacccca
 7321 acacccccag gctggagtgg tttgcagccc tgggcctgcg ctggtacgcc ctcccggcag
 7381 tgtccaacat gctgctggaa attgggggcc tggagttccc cgcagccccc ttcagtggct
 7441 ggtacatgag cactgagatc ggcacgagga acctgtgtga ccctcaccgc tacaacatcc
 7501 tggaggtgag gtgcgggatg gggctcgggc accgaatgca cctgtccaag gcaggagtct
 7561 ggctctcact ccatccccaa aatgccagcc acggggacaa tcagagcagg tccagggttg
 7621 cctcctaaat gggaactgag gacaagctct agaaccactg aagcaaaggg gtaggggtg
 7681 gcaggggtgt gtgtggggt gtgagtgggt gagtgtgaga gtgtgggttt ctgggtgtg
 7741 cagtgggtga gagtgtgggc ttgtgggtg tgtagtgggt gtgagactgt gggtttgtag
 7801 gggtgggtga gtgtgggtgt gtgggggtag gtgggtgtgg gtttgtgggt gtgtataggc
 7861 agtgactgtg agactgtggg tttgtggggg taggtgactg tgggtttgtg gggtgtgtag
 7921 gggtgagtgt gtgtgggttt gtaggggtag gcgagtgtgg gtttgtgggg tgtgtagggg
 7981 tgagtgtgtg tgagtttgta ggggtaggcg agtgtgggtt tgtggggtgt gtaggggtga
 8041 gtgtgtgtga gtttgtaggg gtaggtgagt gtgggtttgt ggggtgtgta gggggtgtgt
 8101 gtgggcttgt aggggtaggc gagtgtgggt ttgtggggtg tgtaggggcg agtgtgagag
 8161 tgtaggtatg tgggtgtgag tgtggatgtg tgtaggcggt gagtgtgaaa ttgtgggttt
 8221 gtgggggtgg gtgggtgtga gtgtgtgggt ttgtgggtgg gtgtgggtgt gagtgggtgg
 8281 gtgagggggg catggggatg ggtgtgaaca tgtagttgtt ctttcaggca taggacccat
 8341 agctctagag ctttcatcag attctcaaag gggaccttga ctcggaaaag gttaagaccc
 8401 attttagaga tgagaaatta aagcctggag ctgaggagcg actggcccaa agtccctctc
 8461 tgctctgagg tgccttcgca ggcaaaaacc tgaaccagcc ccctaggcag ccaggcctcc
 8521 caatggacac cactcacctc actccttcca gccatgtacg ggaaacagag atagtctccc
 8581 caccccaccc ccgtgatcac ctctgtccct accgatgcca cacacccttc tgccccagga
 8641 tgtggctgtc tgcatggacc tggatacccg gaccacctcg tccctgtgga aagacaaggc
 8701 agcagtggaa atcaacgtgg ccgtgctgca cagttaccag gtgcagaggc ccagactggc
 8761 caggaaggca aagggtttgc atacgggggc agcaggggcg gggatggag gagaggcagc
 8821 catttagaaa ctagggcagg atttggacag gcagaagaag ttccgtagtc ccagtgccat
 8881 ggcgcacact ggcctgcggt tcggggacag ggcaggtact attccaggcg ctgtcatctg
 8941 gtggcttact gtgtgccagg gaccttgctg tttactgcat gcccagtcat gctgattctc
 9001 agggcatatt gggtattgca gtttgtggga cccgctggat cctggaaaca aataccagga
 9061 tcaagggcac accaggagtc gtagtttgag gaagccgggg cctgctgaga atttctgtgg
 9121 gctatttggt ttggggacca ggcatgcaga tgctggagat tagagctgct tgttgcatgt
 9181 tgaacctgca gcatgaccat gcatgatgtg gtttggggtg agggtgacat tgtggtttga
 9241 ggggacacag ggtgtgttag atatggggta atcgagggca catgtggttt ggggtgaccg
 9301 gagtggtgga ggaagaatgg gcgaggtctg tgggtctggt ttgagcctct ccccctctct
 9361 ctcccttcca gctagccaaa gtcaccatcg tggaccacca cgccgccacg gcctctttca
 9421 tgaagcacct ggagaatgag cagaaggcca ggggggctg ccctgcagac tgggcctgga
 9481 tcgtgccccc catctcgggc agcctcactc ctgttttcca tcaggagatg gtcaactatt
 9541 tcctgtcccc ggccttccgc taccaggtgc ccaccctaac tggctctgcc agcctgggcc
 9601 cagctctaat tctaagcagc ccctggggac ctctaacctt tccttttctt tacctcccct
 9661 cccaacccca tcatctctct gcagccagac ccctggaagg ggagtgccgc caagggcacc
 9721 ggcatcacca ggaagaagac ctttaaagaa gtggccaagt gggtcccctg ggagccccgc
 9781 tctcccacac acaccctggg ggccccactc tcccccacac accctggggg accctgcccc
 9841 agcagtgttc tgggcctacc actcagtatc ccaaaaccct gttgtgaggg ggttggaccc
 9901 ttgcctgggg aggccctgcc tctgtgcacc cgggacaccc tcacaccttc ctctcccgca
 9961 gcgccgtgaa gatctccgcc tcgctcatgg gcacggtgat ggcgaagcga gtgaaggcga
10021 caatcctgta tggctccgag accggccggg cccagagcta cgcacagcag ctggggagac
10081 tcttccggaa ggcttttgat ccccgggtag ggctgagccc aggggagcag ggagctagaa
10141 agaggggct ctatcagcat cttcaggggt gccctggagg acaggaagtg ttacaagtca
10201 ggactcatga ggaacccgga accacaggtg ttcagagatc aagttggggc ctgaatcttg
10261 cactgccagg gaggccagag tgaggagggc agggcctccg ggggccacag cacccaggac
10321 atctgtcttc ccacccacag gtcctgtgta tggatgagta tgacgtggtg tccctcgaac
10381 acgagacgct ggtgctggtg gtaaccagca catttgggaa tggggatccc ccggagaatg
10441 gagaggtgag aacttccagg aaagggctg ctgggaatga ggagagactc agaattggag
10501 tgactgggca ggaacctctg cccaacacac acacacacac acacacacac acacacacac
10561 acacacacac acacacacac acacacacac acacgccagg atggaaaggg agatgctaag
10621 agaccctgg agcctgaaac cccacacaag ctacgctccc agcccaccca tgtggctgcc
10681 tccctgcaag cacatttgct taactgcgcg tccccaagtc atttccatta tcagtgcaag
10741 tttttaatac aaggaaggca catcctggct gaccaagagg ttagactgtg ctcgggcact
```

Figure 2 (Continued)

```
10801 gacaagaaaa acagggatac gtcactgagg gcggcttcta ggatgcgggt aatgtttctt
10861 aatgggatac tggttacaca ggtgtgttca gtttgtaaaa atccacagag ctgtacattt
10921 acaacatgta caacactatt ccagcatttt attttatttg ttttatttat tttgagaacc
10981 tatttacgtt gcccaggctg gccttgaact cctagcctca agagatcctc ctgccgcagg
11041 ctcctttttc aaaagaagaa attgagcgct gtttagatgc caacatagat taaataactt
11101 cacttttaa aaagaaacac aaagctagag taccatcatt gaattccttc tcttgcaagc
11161 ttaggtatct ctgaggtgcc ccaggctagg ctcatttctg agtcttacct gctccagctt
11221 ctaggtgtta aaggccttat tagcactaag tacttcctca gtactctttt ttcttttttc
11281 ctttgagaca gggtctcact ttgtggccca ggctggagtg cagtagtaca atcacggctc
11341 actgcagcct caacctccta gactcaagca atcctcccac ttcaacctcc caagtagttg
11401 ggactacagg cgcatgccat gatgcctagc taatttttgt atttttata gagatggggt
11461 ttcgccatgt tgcccaggct ggtctctaac tcctgggttc aagcaatcca cctgcctcgg
11521 cctcccaaag tgctgcgatt atagacgtga gccactgcac ctggccctca gtatcttaag
11581 caagttggaa tctcgtgaaa cccttttgc tgccttagtg tccgtttcag ccctcattct
11641 gacctacctt ttcaagaaaa atagcaccag caattgactt tttttagca taaaggtgta
11701 tagacaccca tataacctac agccttcaca aggcatagca cattttcacc accctggaaa
11761 gttccctcat cagttcctca cgtgaatccc ttcccagtct gtctccctgc cagaagtgtc
11821 tgtcaccaca gaatagtttc gcctgctcta gaacggcacc tagatggaag cacgcagtgt
11881 tgcggcgtct cctgctgagg ctgtttttga ggcgcactcg tgttgctgcg tgactcagta
11941 tttcactcat tctgctgctg agtgccgttc attgtgtgaa tatccccagt ttgtttaccc
12001 attctcttgt tggtgacact tgggctgttt ccaggtcggg gctattatga ataaacctgt
12061 tatgaacatt cttgtacccg gcttttgtgg gcttatgttt ttatttctct tgggtaaata
12121 cctaggagta gaattggtag gtcatagggt agatgcatgt ttaatctttc actttttaa
12181 aaaataaaac tgccaggcca ggcgcggtgg ctcacgcctg tgatcccagc actttgggag
12241 gcccaggtgg gtggatcact tgaggtcaga agctcaagac cagcctggcc aacatggcaa
12301 aaccctgtct ctactaaaaa tacaaaaatt agctgggcat ggtggcgcac gcctatagtc
12361 ctagctactc aggaggctag gcgggagaat tgcttgaacc tgggaggtgg aggttgcagt
12421 gagccgagat cacgccactg cactccagcc tgggtgacag agcaagaatt ctacttaaaa
12481 taaaatacaa ataaataaaa taaaactgtc aaacagcaaa gcaaattaaa ctgcccttta
12541 acatctgtgc agttcaatgt atgttaattt tatcccaaat ttttaacaaa tctaggaata
12601 cagctcacag aaaatggggt atattcacta aaaataagga atatttatag caaatttgtt
12661 tgtaataccc cacactggaa acaattcaaa tgaccatcga caaatactga taaattgtgg
12721 tatattcaag tgccatatcg cactaagtgt gaacgaaaca caaccacaca caacagtgca
12781 ggtgaatctc aaaaaatgtg aagagaagaa aaagccagac caaagaatac atactgtact
12841 acagggttca ctttatataa agttcagaaa caggcagaac taatccacgg agttagaaat
12901 taggagagga gttagtcact gggatggggg tggcagtgac aggaagaagg cacgaagttg
12961 gcttctagga tgcgggtaat gtttgtttgt ttgtttgttt gtttgttttt gtttttgagc
13021 tggagtctca ctctgttgcc caggctggag tgcaatggcg tgatctcggc tcactgcaac
13081 ctccgcctcc ccggttcaag cgattctcct gcctcagcct cccgagtagc tgggattaca
13141 ggtgcccgcc accatggcca gctaattttt gtgtttttag tagagacgcg gtttcaccat
13201 gttggccagg ctggtcttga atccctgacc tcagcctccc aaagtgctgg gattacaggc
13261 gtgagccacc acgcccagcc acgggtaatg tttctcgatg ggatgctggt tgcacaggtg
13321 tgttcagttt gtgaaaactt acagagttgt acatttacaa catgtgtgca cctctggact
13381 tgtgttgcac gttgacaaaa cattcaaaaa tgaaattcaa atcgttcttg ctaactctgg
13441 cgcacttggg aaccagcacc cagaggcatc tgcagttgag caccagatgc agttccttcc
13501 agcttccttc cccctgggag gtccgcttga tgccacttct tcatggcagc acaaacaagg
13561 ccatggtctt ctgaggaggg caacctgcac aatgtctgct agtgaccagg acactgctga
13621 aggaactgag agtttgtcca cccatgaaat ccactaaaac aggaaagatt ttgctctagc
13681 cgttgttagc caggagtgag gaaagagctg tgccctcccc tgcagctgcg aggacgatct
13741 gcctgcccca acaagtgggg attcagcaac tccacttcta aggattaccc agctgaagca
13801 tttaaaagtg ggagcaaggc acacgtacaa gggcgtttga gagagcacct gttcccagac
13861 caccgagctg cccttcagtc tcagtgaagt acaatgtagc cactaaaaag actgaggtca
13921 tgttttggaa agtccaggcc ggaggatcgc ttgagcccag gagttcaagg ccagactgaa
13981 caacacagcg agactccatc tcttcagaaa atttaaaaat taaccaagag tggtggcacg
14041 cacctataga tctagctact aggaaggcag aaaaatccct taagcccagg agtctgaggt
14101 tacagtgaat gatgatggag ccactgcacc ccaacctggg cgacagagca agacccatat
14161 ctaaaaacaa tactactact tacgtcaata ttgttgtatt gacctggagg gatgtctgca
14221 ataaattatt gattaaaacc aaggaagtac agtatggtac cacttttact taaaaaaaaa
14281 actataaata tgcacatgca cgtaagttca aggaaaaagg gctggaaggt taacacctgt
14341 caatggcgca tatgcccgga gggaagatgg ggtggtcttt gtcttatcac tttacacatt
14401 tctgtaatgt catttttcaa aaacatcaga tcgcttttga aattttcaaa acaaataaaa
```

Figure 2 (Continued)

```
14461 attaagttac aaatcaataa taatgaggat cagctggtac agttttaaac ttctatgtag
14521 tttgaaatga aacaaaacta accctgatgc aaacactccc ctcgccagag ctttgcagct
14581 gccctgatgg agatgtccgg cccctacaac agctcccctc ggccggaaca gcacaagtga
14641 gttgggtgag agtttggggg agctgggga gctgatgcat ttggagacac aaacagaaag
14701 ggggtctgaa aagctctccc tctgtgcctc aagtcgtttt cccaccaaaa gccagggctc
14761 caggatgccc tccattccag gctgcaatgg cagtcctaga cctgcctgct tctgagagcc
14821 gggacagtcc tgaggtcttc agagatgggg gtgtggtgtg tcagggcccc aggctcggaa
14881 ccccagggat gctggccctc agcccctccc aagggcaggg cctttcctgt cccagaggca
14941 gagaccctga agccgtccct ggggctgggg ctgggcctag cctgtatccc cagggccctg
15001 tgacaacctt gtctttgtcc tctcttgcca ggagttataa gatccgcttc aacagcatct
15061 cctgctcaga cccactggtg tcctcttggc ggcggaagag gaaggagtcc agtaacacag
15121 acagtgcagg ggccctgggc accctcaggt cagggcctca ccaagagggg tgcaacgggt
15181 gggcaagctg cctgggcaaa cgtggcctgc aaagggagct ccactgacga cccctgcacc
15241 ccaggttctg tgtgttcggg ctcggctccc gggcataccc ccacttctgc gcctttgctc
15301 gtgccgtgga cacacggctg gaggaactgg gcggggagcg gctgctgcag ctgggccagg
15361 gcgacgagct gtgcggccag gaggaggcct tccgaggctg ggcccaggct gccttccagg
15421 tgagcccagc ccagcccctg ctctgactcc tgccccctgg gatgcctcct cctgcctcac
15481 tctgccctga ttctgtttgg ttctttggtc ccttcctgtt ccttccaaaa tccaccctca
15541 tctctccatg gcatagccag ctcttctggg tcaggggcag aggatgacat ggccctgccg
15601 accacagggg tgcctagccc aggcagaagt gcagccgaaa gagagcaggc agggccctgg
15661 caggagggag cttcagccag gcacaggctg ggcctcacaa gtgggcgcac aaagggaggg
15721 ggtgcagggc agggcagggg accccaccca ggatgggcag gatggaggga gaaggaaggg
15781 acagagagaa ggtcagacag aggcaagggc tgaagctgag gccagcacag aagccacagg
15841 aagccagagg ccagacagcc tggggcggtg cctgcaccgc agaactggtc ccgggccggg
15901 caagcaagca cagggagagg tggatccctg gggctgtgg cttttaagc ctgggcttcc
15961 tcaggggcag tgctgcctgt ctggggatca tgtctgcagt tgacaagggc tcggtctccc
16021 cagtgccaca ctgttcaggg cagtgctgct gtcccgggc ccaggctgga gctcagcaga
16081 tttgccttga ttggaggagg agggcatcct aggaggagag ggagtggggg ctacctcagg
16141 gacggggagg tcaggctgca gaaacacata ggccctgatt gggaagaagg gaacggaaaa
16201 taagacttaa agaatttaaa caaaaagagc cattgcagcg ggatgagacc acatcatcag
16261 gttttgggaa taggacttta gaggcgtagg atccattaca gcatcaccga accagaagca
16321 ggaaggctga gctaagcaga gcagcagcag tggagatagg aaggaaggga gggaggggcc
16381 gaggaaggaa ggaagagata taagacttca cacgcaccac aaaagaaaga ttaacgggac
16441 ttggtgatat gaggctcagc caatcacggg tgagccctgc atttcaagcc tgggactggc
16501 ccagcagttt tccagctgtg tgcctgacca ggagtagacg ggatccacac cctcccaggg
16561 atctgccccg tggggtcccc tctgccgccc gaattgtgcg tcccttccca ggagcactta
16621 ctatctgcac gcactttgtg gaaagctaag ggctttacat aaagtatctc atttaatctt
16681 caccagaaca caatgaggtg taaagatggg gaaactgagg catgtcactg taagtacggg
16741 attcggaatt tgaatgcagg tctgaacaca cagacgcctt cacagagcta ccgtgtgcca
16801 agcactatgc ttctcggatc acgggattaa cacgcaccag ataaggaacg atgcaccaat
16861 caggacgtgc agagaaagag ccagccgggt ccctgggccc agcggccaat ccatgaaatg
16921 ggctggcgga aaaggtgctg tccttggcgc cggcctcagc cactggggct gccaaccccc
16981 caggagcaag acgcagtgaa gccgcccagg cgcctcacta gggcgacccc tggtggcggg
17041 gaggtcctca gccctcaccg gcctgtcccg caggccgcct gtgagacctt ctgtgtggga
17101 gaggatgcca aggccgccgc ccgagacatc ttcagcccca aacggagctg gaagcgccag
17161 aggtaccggc tgagcgccca ggccgagggc ctgcagttgc tgccaggtgg gccctgccct
17221 caccctaacc cggctggttc tctgaggccc ccacaccccg ggactaaagc actctggggc
17281 caggccctgc tccctagctc aggctgcctc atttgcccct ccccgccccc aggtctgatc
17341 cacgtgcaca ggcggaagat gttccaggct acaatccgct cagtggaaaa cctgcaaagc
17401 agcaagtcca cgtgaggacg acggctttac cgccccccaa cccctgtcct gaacaccctg
17461 accctggacc ctcctcctcc cacattctcc cgccccccacc cctctctgac tccccataag
17521 tgcccctctc cccaccccca ggagggccac catcctggtg cgcctggaca ccggaggcca
17581 ggagggctg cagtaccagc cgggggacca cataggtgtc tgcccgccca accggcccgg
17641 ccttgtggag gcgctgctga gccgcgtgga ggacccgccg gcgcccactg agcccgtggc
17701 agtagagcag ctggagaagg gcagccctgg tgaggggcag cctgggaagc aacagggcac
17761 accagcccca tgcccagccc caccccggc cccaggcctc caggagctca ggacccgacc
17821 caggggtgg ccacctcctc cacagctcag caggcaggct cagagctggc tgtgctgccc
17881 actgccgggc tggccttgtt gctggaccat ccccacaccc tcaaatgcac ccccaccaaa
17941 aggctgtccc ctccctctgg gctcctctcc aaggctcccc tagcaatcta gcttgctctg
18001 gagctggcac tggggctatt tgctgccaca tcaatgcctg ggctttattt aaaataaggg
18061 ggtggagtca gaggcagagg agcccagacc aacccagtcc ggccaggggc ccccgaacaa
```

Figure 2 (Continued)

```
18121 tacactgagg ctacctagac aggccgaccc cgctgctcaa gggcaggctc tctaacagtc
18181 accaaaacac aaacatcagc ccaggtactg cagtcctgct gggccctgtc ctcagagctc
18241 cctgtgcact atccccaggt ggccctcccc ccggctgggt gcgggacccc cggctgcccc
18301 cgtgcacgct gcgccaggct ctcaccttct tcctggacat cacctcccca cccagccctc
18361 agctcttgcg gctgctcagc accttggcag aagagcccag ggaacagcag gagctggagg
18421 ccctcagcca ggttgggggc caccccaatg aggcacaggg gctagagaga cgggatgagc
18481 tgggggggacc ccagtggcag gaaacccccca tgcaaagtcc cccctggact ttcttctcct
18541 ggctgacatg cactggtgct ttaagaccca gctcctcagg gaggaattca tggctggatt
18601 ctccaggtct tagagaaaac tctattggcc tgaactgagc agggagaaac cctaaagagg
18661 ctcagtgggg gaggggtcaa gaagggaggt tactaggaag ggctatgggg cctccaaccc
18721 actgcatcct gccccgccag gatccccgac gctacgagga gtggaagtgg ttccgctgcc
18781 ccacgctgct ggaggtgctg gagcagttcc cgtcggtggc gctgcctgcc ccactgctcc
18841 tcacccagct gcctctgctc cagccccggt actactcagt cagctcggca cccagcaccc
18901 acccaggaga gatccacctc actgtagctg tgctggcata caggactcag ggtgaggcaa
18961 caagcaggag caggcctggc cacagcaggg ttgggaccgg cccctctctg gcccctcacc
19021 ggcctctcct tcccaccccc agatgggctg ggccccctgc actatggagt ctgctccacg
19081 tggctaagcc agctcaagcc cggagaccct gtgccctgct tcatccgggg gtaagtgaga
19141 tggaggactt ggtggggagc tgcccagggt cagggtggca gctttggtga ggagtgtcac
19201 tggtgagggg tgtcactgga aacaggaagg agctctgtaa catgtcaagg gtgtggtgtc
19261 attaggtcac ttcagaactc tggctaagct ttggctctct cattcattta gactcagagt
19321 tctgccctga aactatagct cccagagcca gagctggtat caaaccggct ggccctgtgg
19381 ctttctgaaa gcttctgtgt tcctctctat gtccctgggc tgtctgatgt tgggcagcat
19441 ggcacctggg aactacagtc actaaatcct cactcaatcc agggagaact actagttagg
19501 gttaagacca ccctttggcc ttggtgtcac caaggactca aagaaggtga aggttttggt
19561 ttttttttcc cccagagatg gagtcttgct ctgtcgccca ggctggagtg cagtggtacg
19621 atctcggctt actgcaacct ccgcctcccg ggttcaagag attctcctat ggcgtgaacc
19681 tgggaggtgg agcttgcagt gagccaagat tgtgccactg cactccagcc tgggcgacag
19741 agccagactc tgtctcaaaa aaaaaaaaaa aaatattctc ctgtctcagc ctcctgagta
19801 gctgggatta caggcaccca ccaccacgcc cagctaattt ttgtattttt agtagagacg
19861 gtgtttcact atgttggcca ggctggtctc gagctcctga cctcacaatc ctcccacctc
19921 cgcctcccaa agtcttggga ttacaggtgt gagccaccgc gcccggaccg agggtgaagg
19981 attttaagag acccttcctt catgctgtgt ccagaagtct tgcccgctct cgcagccagg
20041 aaccaaaagt cctggtagga ctgagaacag ttcctaggct gccatcagct gggcctggtg
20101 attcaaatcc acccaggtgg ctaaactaca aataaaccgt acccatctac tgaacataaa
20161 ctaaatacca ctattaagga tacttaaaat aaacacactt agtgaaccca ttatgaactg
20221 aaagtgtctt tcacccttcc cacgttttct aaatcccctg agtcatctaa gtattcttca
20281 atccaaaatg aactatattt cctttggtgc aatctccaga aaccacagat ccaaggagtt
20341 tcagcaagta gagttgtttt ttgtttttttg tttttttttt aattttttttt tgagatggga
20401 agaacttggg tcctccttgc tccacccacc ctgcatggtg agaatggtgg agcaggaaag
20461 gcaaagggga cctgatggag tgtctctcct gccaggctcc cctccttccg gctgccaccc
20521 gatcccagct tgccctgcat cctggtgggt ccaggcactg gcattgcccc cttccgggga
20581 ttctggcagg agcggctgca tgacattgag agcaaaggtg aggctgggga ctaaaggact
20641 gcctgaaggg agtcacacaa tctagggaca gaggggtggg gctggaaggc aggaaatagg
20701 aaagagaggg caggaaacaa agtccacaaa gctgaaaaga cgctcatgag accaagggga
20761 gggcaggtac caaaggcaag ggctgggccc tgagcttctg gcttcctggt gcctggtaca
20821 tagtaggtgt tgactggatt gaggacaaag gaaaatagaa ttttcaaagg gattagggct
20881 aagactcaaa gaagaactgc ccaaggtgga ttcttgactg tgccagagct gaccgaggtc
20941 tgtccaagac ctaaggatgc tacaaggtgt tcatattgag catggggtgc ccagggtggt
21001 ctgtcaatca aaagaagagg gctgtgactg ggaggagagt tataagtatg ggagaatatg
21061 aagtgggagc ggggaagggg actgcgatgt cacacaatgc aaagggcatg gaattctgag
21121 tccgaagccg cgcattctag cgcagctcca ccagggggcca ccacctcacc cgcgcttccc
21181 ttccctctgt aaatcagggc tgtgcagggt ctctgtgaaa gcattctaca ctctcttaga
21241 gatgaaacag ccaaagtaat ggtggtttca gcccaaaacg ctgggctgcc aggctgggcg
21301 acggtggcct gtggggaggc cccactagca ctgtgccccg gagaagagcc ttcccaagcg
21361 cggggttgct tgcagggctg cagcccactc ccatgacttt ggtgttcggc tgccgatgct
21421 cccaacttga ccatctctac cgcgacgagg tgcagaacgc ccagcagcgc ggggtgtttg
21481 gccgagtcct caccgccttc tcccgggaac ctgacaaccc caaggtgtga gaccctgagg
21541 gcgcaatggt aacctgaaga tagggagaga ggggaggact cgcgctctcc agcggggcac
21601 accaaccacg gccctcccgt ggcctcccac gaccactcag ccacccctgc acactctggc
21661 ccacccttgt gccccggccc ctctaggccc gcctcctccc gcccctgccc cgcccctttg
21721 gctctgcccc tgttgacacc gccccagggc acgcaggccc caccaggccc gctccggaga
```

Figure 2 (Continued)

```
21781 ctttcacgtc cagggccagc cagcagcccc gggctgcgcc cccgcgccca cccccaccag
21841 ggcccgccct aaccccgccg ccccgcagac ctacgtgcag gacatcctga ggacggagct
21901 ggctgcggag gtgcaccgcg tgctgtgcct cgagcggggc cacatgtttg tctgcggcga
21961 tgttaccatg gcaaccaacg tcctgcagac cgtgcagcgc atcctggcga cggagggcga
22021 catggagctg gacgaggccg gcgacgtcat cggcgtgctg cgggtgcgga ggggcgggcc
22081 gggcctgagc gtgcggggtt cctgctaagg tctccgagtc gggttctgat ccactgtgct
22141 cttttccgac aggatcagca acgctaccac gaagacattt tcgggctcac gctgcgcacc
22201 caggaggtga caagccgcat acgcacccag agcttttcct tgcaggagcg tcagttgcgg
22261 ggcgcagtgc cctgggcgtt cgaccctccc ggctcagaca ccaacagccc ctgagagccg
22321 cctggctttc ccttccagtt ccgggagagc ggctgcccga ctcaggtccg cccgaccagg
22381 atcagccccg ctcctcccct cttgaggtgg tgccttctca catctgtcca gaggctgcaa
22441 ggattcagca ttattcctcc aggaaggagc aaaacgcctc ttttccctct ctaggcctgt
22501 tgcctcgggc ctgggtccgc cttaatctgg aaggcccctc ccagcagcgg taccccaggg
22561 cctactgcca cccgcttcct gtttcttagt cgaatgttag attcctcttg cctctctcag
22621 gagtatctta cctgtaaagt ctaatctcta aatcaagtat ttattattga agatttacca
22681 taagggactg tgccagatgt taggagaact actaaagtgc ctaccccagc tcatgtggat
22741 tacagttttt ttttttgtt ttttttttt tgaaacggag tctccctctg ccgcccgggc
22801 tggagtgcag tggcgtgatc tcagctcact gcaacctcca ccccacaagt tcaagtgatt
22861 ctcctgcctc agcctcccaa gtagttggga ttacaggtgc ctgccaccgc gcccggctag
22921 gttttgtatt tttagtaaag acggggtttc accatcttgg ccaggctggt cttgaactcc
22981 tgacctcgtg atccaaccgc ctcagcctcc caaagtgctg ggattacagg tgtgagctac
23041 tgcacccggc gtggattaca attataaaat gacaagattt ctgttttaac ctgtgcagtt
23101 gtgggtatgt ggtggggaaa ggggtcattc ttttgacaga gtcctacacg ccacttgacc
23161 ctgcactctg aaaacatggt ttccagccag tctgggctgc tcccccgtgc agttctcagg
23221 ctcgtgatcg agaaggcagg tgcagcactc agctgccagg agtggggcct gccagaaaca
23281 agagtcacag agatgtgcaa cagccatgag caagctttac tgcttatttc atacaggatg
23341 gggagccaca cccacttcct gggacatcac acccgtactg aagtccaaaa acatcatccc
23401 tcccgtcttt ccactgacaa gtccccatcc cctacaagcc ccaaggaacc tgaaagtgct
23461 gctggcagcc gccagcatga cgaatccaca gccttaaagc ccacctgcct cactgtcgcc
23521 cttccattta gctcggcctc atccttgacc tctgtccccc accttgagga aactcgagga
23581 cttcttccca ggcagctgct ccaggacaca ttccagttgg ggatgtctcc ccttattccc
23641 tctgggtgca gaccatctct aagacttgtt tccagatgcc atcagcatct cctctccttg
23701 cctacctttt ctctgttctc ggggcgagtt cctcactgac tcccaggtcc tgcccaacta
23761 aagcacctgg gcctgtcatc tatggggcct ctaacaatga ctccttgtgt ttttctactc
23821 caccctccaa tctcctgtgg ctgccgaagc cagggtacct gtgggaggag acggctcttg
23881 gcaagcagtc caggggtcta gattccagag atgaccacct cccatcaccc caaattccca
23941 ccactgctcc catcgcttca agtcggactc caaaccaact acctatgccg tcctttctcc
24001 ctcccctcac aggaggcaat actgaccctg aggagtcgtc tcagtcagtg caagaggccc
24061 ggtcaggctc cttctgggtg tctgtggtca cctgaaaccc tccggggaac agattccggg
24121 ccttctgggt tccccactgt tgtctggggc tagaggcagg actggagcct ggtgaaaaag
24181 gccatcagct gggcagttcc atgatgccca gtgtccacca ggctctgtcc cctgcaggcc
24241 ccaccctcct caccgtcact tgaccaggat ggcttctcct catcaggcga gggtggctgt
24301 gaggggctgg agcagggcct ggacaggatg gaggctgcag cctcacccca cggctcctgc
24361 tgctgctgct gctggtgaag ctgcatggaa aggaggagga atgagggctg caccccaagg
24421 agggcagggc caagcacctg ggctagaggc agagggcttt tcagcctcct cctgccactc
24481 tgctagaccc ttccgtagac tccaccccac ctcagtctcc atgttgttca cctgccttct
24541 ctccacattt ctcctttggg cacccctcta ctcacctggt gcaggtagat gacatggaga
24601 ctcatctcgg cagaagcaag ttctgggagc tgggccagct tctggccccc agtgcctcct
24661 ggggacacag agctggaaca taacatgaag caggtcaaaa gtcatgccct cctcccgcca
24721 caccccagag gactcccctt ctgaatcccc cctcagcgcc ccagctcccc actcctacag
24781 gatcagccca cccccctcca catgcccctg catctcagcc tccactcctc acctggggtc
24841 ctgggcaatt cgggaaatgg aggcaaggag gctggctgtg gccgcagctg gacagggggc
24901 tgtcgggctc agatctctcg gaggcaggag agggtgcacg aagaggttgg ccaggaaggc
24961 ctcaggctgg gtgcaagagg agagggaaag ccaaagaggg agtcagaaga gaggacagaa
25021 acggagtagg gaggaagcag aggcctaaag aaggcaggag agcaggctgg gggcgggggc
25081 tggtgaggca ggttactacc taaggt  (SEQ ID NO:1)
```

Figure 3

MGNLKSVAQEPGPPCGLGLGLGLGLCGKQGPATPAPEPSRAPASLLPPAPEHSPPSSPLTQPPEG
PKFPRVKNWEVGSITYDTLSAQAQQDGPCTPRRCLGSLVFPRKLQGRPSPGPPAPEQLLSQARDF
INQYYSSIKRSGSQAHEQRLQEVEAEVAATGTYQLRESELVFGAKQAWRNAPRCVGRIQWGKLQV
FDARDCRSAQEMFTYICNHIKYATNRGNLRSAITVFPQRCPGRGDFRIWNSQLVRYAGYRQQDGS
VRGDPANVEITELCIQHGWTPGNGRFDVLPLLLQAPDEPPELFLLPPELVLEVPLEHPTLEWFAA
LGLRWYALPAVSNMLLEIGGLEFPAAPFSGWYMSTEIGTRNLCDPHRYNILEDVAVCMDLDTRTT
SSLWKDKAAVEINVAVLHSYQLAKVTIVDHHAATASFMKHLENEQKARGGCPADWAWIVPPISGS
LTPVFHQEMVNYFLSPAFRYQPDPWKGSAAKGTGITRKKTFKEVANAVKISASLMGTVMAKRVKA
TILYGSETGRAQSYAQQLGRLFRKAFDPRVLCMDEYDVVSLEHETLVLVVTSTFGNGDPPENGES
FAAALMEMSGPYNSSPRPEQHKSYKIRFNSISCSDPLVSSWRRKRKESSNTDSAGALGTLRFCVF
GLGSRAYPHFCAFARAVDTRLEELGGERLLQLGQGDELCGQEEAFRGWAQAAFQAACETFCVGED
AKAAARDIFSPKRSWKRQRYRLSAQAEGLQLLPGLIHVHRRKMFQATIRSVENLQSSKSTRATIL
VRLDTGGQEGLQYQPGDHIGVCPPNRPGLVEALLSRVEDPPAPTEPVAVEQLEKGSPGGPPPGWV
RDPRLPPCTLRQALTFFLDITSPPSPQLLRLLSTLAEEPREQQELEALSQDPRRYEEWKWFRCPT
LLEVLEQFPSVALPAPLLLTQLPLLQPRYYSVSSAPSTHPGEIHLTVAVLAYRTQDGLGPLHYGV
CSTWLSQLKPGDPVPCFIRGAPSFRLPPDPSLPCILVGPGTGIAPFRGFWQERLHDIESKGLQPT
PMTLVFGCRCSQLDHLYRDEVQNAQQRGVFGRVLTAFSREPDNPKTYVQDILRTELAAEVHRVLC
LERGHMFVCGDVTMATNVLQTVQRILATEGDMELDEAGDVIGVLRDQRYHEDIFGLTLRTQEVTS
RIRTQSFSLQERQLRGAVPWAFDPPGSDTNSP (SEQ ID NO:2)

Figure 4

```
GTGGTGGGTA CCTGTAATCT CAGCTACTCA GGAGGCTGGG TCAGGAGAAT 50
CGCTTGAACC CAGGAGGCGG AGGTTACAGT GAGCTGAGAT AGCACCATTG 100
CATTCCAGCC TGGACAACAA AAGCGAGACT CTGTCTCAAA AAAAAAAAAA 150
AATTAGCCAG GCGTGGTGGT GGGTGCCTGT CGTCCTCGGG AGGCTGAGGC 200
ATGAGAATCA CTCCGGGAGG CAGAGGTTGC AATGAACCAA GATCACACCA 250
CTGCACTCCA GCCTGGGTGA CAGAGCAAGA CTCTGTCTAA AAAAAAAAAA 300
AAGACAGAAG GATGTCAGCA TCTGATGCTG CCTGTCACCT TGACCCTGAG 350
GATGCCAGTC ACAGCTCCAT TAACTGGGAC CTAGGAAAAT GAGTCATCCT 400
TGGTCATGCA CATTTCAAAT GGTGGCTTAA TATGGAAGCC AGACTTGGGT 450 | T450A
TCTGTTGTCT CCTCCAGCAT GGTAGAAGAT GCCTGAAAAG TAGGGGCTGG 500 | A479T
ATCCCATCCC CTGCCTCACT GGGAAGGCGA GGTGGTGGGG TGGGGTGGGG 550 | G543T
CCTCAGGCTT GGGGTCATGG GACAAAGCCC AGGCTGAATG CCGCCCTTCC 600
ATCTCCCTCC TCCTGAGACA GGGGCAGCAG GGCACACTAG TGTCCAGGAG 650
CAGCTTATGA GGCCCCTTCA CCCTCCATCC TCCAAAACTG GCAGACCCCA 700
CCTTCTTGGT GTGACCCCAG AGCTCTGAGC ACAGCCCGTT CCTTCCGCCT 750
GCCGGCCCCC CACCCAGGCC CACCCCAACC TTATCCTCCA CTGCTTTTCA 800 | C789T
GAGGAGTCTG GCCAACACAA ATCCTCTTGT TTGTTTGTCT GTCTGTCTGC 850 | C823T; T835C
TGCTCCTAGT CTCTGCCTCT CCCAGTCTCT CAGCTTCCGT TTCTTTCTTA 900
AACTTTCTCT CAGTCTCTGA GGTCTCGAAA TCACGAGGCT TCGACCCCTG 950 | G943A
TGGACCAGAT GCCCAGCTAG TGGCCTTTCT CCAGCCCCTC AGATGACACA 1000 | C985G; A996G
GAACTACAAA CCCCAGCATG CACTCTGGCC TGAAGTGCCT GGAGAGTGCT 1050 | C1023T
GGTGTACCCC ACCTGCATTC TGGGAACTGT AGTTTCCCTA GTCCCCCATG 1100 | C1062T
CTCCCACCAG GGCATCAAGC TCTTCCCTGG CTGGCTGACC CTGCCTCAGC 1150 | T1132C
CCTAGTCTCT CTGCTGACCT GCGGCCCCGG GAAGCGTGCG TCACTGAATG 1200
ACAGGGTGCG GGTGGAGGCA CTGGAAGGCA GCTTCCTGCT CTTTTGTGTC 1250 | C1229T
CCCCACTTGA GTCATGGGGG TGTGGGGGTT CCAGGAAATT GGGGCTGGGA 1300
GGGGAAGGGA TACCCTAATG TCAGACTCAA GGACAAAAAG TCACTACATC 1350 | A1339G; T1345A
CTTGCTGGGC CTCTATCCCC AAGAACCCAA AAGGACTCAA GGGTGGGGAT 1400
CCAGGAGTTC TTGTATGTAT GGGGGGAGGT GAAGGAGAGA ACCTGCATGA 1450
CCCTAGAGGT CCCTGTGGTC ACTGAGAGTG TGGGCTGCCA TCCCCTGCTA 1500
CAGAAACGGT GCTCACCTTC TGCCCAACCC TCCAGGGAAA GGCACACAGG 1550
GGTGAGGCCG AAGGCCCTTC CGTCTGGTGC CACATCACAG AAGGACCTTT 1600
ATGACCCCCT GGTGGCTCTA CCCTGCCACT CCCCAATGCC CCAGCCCCCA 1650
TGCTGCAGCC CCAGGGCTCT GCTGGACACC TGGGCTCCCA CTTATCAGCC 1700
TCAGTCCTCA CAGCGGAACC CAGGCGTCCG GCCCCCCACC CTTCAGGCCA 1750
GCGGGCGTGG AGCTGAGGCT TTAGAGCCTC CCAGCCGGGC TTGTTCCTGT 1800
CCCATTGTGT ATGGGATAGG GGCGGGGCGA GGGCCAGCAC TGGAGAGCCC 1850
CCTCCCACTG CCCCCTCCTC TCGGTCCCCT CCCTCTTCCT AAGGAAAAGG 1900
CCAGGGCTCT GCTGGAGCAG GCAGCAGAGT GGACGCACAG TAACATGGGC 1950 | UTR; Exon 1
                                              M  G  2
AACTTGAAGA GCGTGGCCCA GGAGCCTGGG CCACCCTGCG GCCTGGGGCT 2000
N  L  K  S  V  A  Q  E  P  G  P  P  C  G  L  G  L 19
GGGGCTGGGC CTTGGGCTGT GCGGCAAGCA GGGCCCAGCC ACCCCGGCCC 2050
 G  L  G  L  G  L  C  G  K  Q  G  P  A  T  P  A  35
CTGAGCCCAG CCGGGCCCCA GCATCCCTAC TCCCACCAGC GCCAGAACAC 2100
P  E  P  S  R  A  P  A  S  L  L  P  P  A  P  E  H 52
AGGTAAGGGC CAGGCAGCTA GGAGCAGCTG GGCAACAAGG GTGGTCTCAA 2150
 S                                                53
GGCCTGAAGC CTGGGGCTGG GAAGGTCTGG AACTTGTAGC TGAGTCGGGA 2200
GGGCCAGGTC ACAAATGCAA AAGGGCTATT AATGTGCATA GAACAGGACA 2250 | C2226T
GTCTGGGAGG CTCAGAAAGG AGACCAGGAT CAGAGTCGGC AGGTGAAAGC 2300
TGGGAGTAAG GGTGCCAGCT ATAGAATCTG GCCAGGGTTT GAATGCTGCT 2350CTGCCGCCAG
GAGCTGTTTG ACTTTGAGCA AGTTACTTAA TCTCTCTGAA 2400
CCTCCATTTA TATAAAACGA GATATGGCAA TACTTACTCC ATGGGGAAGT 2450
AAGTTTCTAG CTCACAGCAA GCCTTCAACA GCAGCGATGA TTATTTAGCT 2500 | A2493G
GGAGAAGAAA GGAGCTGACA GCAGTGGTTA CAGGAGTGAG AAAGTGGGGT 2550
CTCCCAGAAG AGGGAGAGAG TTGGGCAGGA AACTCGGGCC CTTGGGGTAA 2600
GCAGGCTGAG AAGACAGAGC CACCAGGCTT TTTTCCCCTG CTCCAGCCCC 2650
CTCTCCTCGT GGCTGTCACC CGAAAACTGG ACCATGCAGT TCCCACAAGA 2700
```

Figure 4 (Continued)

```
GTCCTCCCGG GGGTAGAGGT CCCAGGAGGG AGGAAAGACC CGGAGGCCTG 2750
GTGGGGTGCC AGGCCGGGGG CAGGCTGGGG CTGCAGGCAG CTATGCAGGG 2800
AAGGCTGAGG GCCGGGGCCC TGCTGCTCAG GCGCACCCTT GGCCTGAGTC 2850
CCTCCCTTCC TCCCTGCCGC TGGTGGCTCT GGGAGGAAGT GATAAGGCCT 2900
GCGAGGCTTC CCTTCACACA TGGGGCTGCT GTCAGGAGGG GTTGTGAGTG 2950
CGGAGGGAAA TCAGAGCTGA GGAATCCCTG CAGGGCTTCC CTCCACTCAA 3000
GCACCAGGCT CTGTCCCCCT CAGGGTAGGG CTTATAGCAG CTTTGCGGGG 3050
GGTGGACACC CCATCTCCAG AAGAGGTGAG GTGGGCGCTG CAGGTGGGAT 3100
GCGAACTTAG CCTCGGGTCA GGGGCTCAGC AGCTCAGCAC CAGCAGCCCC 3150
TGCAGCCCAG GACCCTGGTC TATAAACGGA GGCACAGCTC GCCTCTAGCT 3200
CCTAAGGCAT GGGGAACGCC AGAAGGCATG CGGCAGGTGG GCTGTGAGAT 3250
CGCCAGTGCT GTAACAGGGG CCTCCGGGTG ACATCTGGGA AGGCTGAAAG 3300
GAAACAAACC CTTCCTGATG ACCCTATCCC TGGCTCCCAA CAGCCCCCCG 3350 | Exon 2
                                                 P  P 55
AGCTCCCCGC TAACCCAGCC CCCAGAGGGG CCCAAGTTCC CTCGTGTGAA 3400
 S  S  P   L  T  Q  P   P  E  G   P  K  F   P  R  V  K 72
GAACTGGGAG GTGGGGAGCA TCACCTATGA CACCCTCAGC GCCCAGGCGC 3450
  N  W  E   V  G  S   I  T  Y  D   T  L  S   A  Q  A 88
AGCAGGTAAG GCCGGCATGC CCTGTCCCCA TCGTCTCCAG GGAAAGGGTG 3500 | G3497A
Q  Q                                                    90
GGTAAGGCCT GGCCTCAGAT GGGGCCGGAG AGGGAAGCTC AACCCTTCTT 3550
TGAATTGGTC CCTTGTTTCC AAAAAGAGGA GAGGACTGGG AAGAACCAGA 3600
GGAGTTGAGG GACATGCACG GGACTTGGGT GACCCTCAGC CTCCAGCCTT 3650
ACCCCCAACC CTGGCTCAAA CTCTCCCCCA TCCCACCCCT CCACCCCTTT 3700
CCCCCCTCCC ACCCCTGCAC CCTTCCTCCC TCTCCCCCCG TCCCCTGCCT 3750
GCATTCCTCC TCCCTCTCCC CATCTCACCC CTGCACCCCT CTTCCCTCTC 3800
CCACCCCTGC ACCCCTCCTC CCTCTCCCCG TCCCACCCTG CACTCCCGCC 3850
CTCTCCAGCG TCCCACCCCT ACACCCCTCC TCCCTCTGCC CCATTCCACC 3900
CCTGCACCCC CTCCTCCCTC TGCCCCGACC CACCCCTGCA CCCCTCCTCC 3950
CTCTCCCCCG TCCCACCCCT GCATCCCTCC TCCCTCTGCC CCGTCCCACC 4000
CCTACACCCC TCCTCCCTCT CCCCCATCCC ACCCCTAAAC CCCTCCTCCC 4050
TCTCCCCTGT CCCATCCCTG CACCCTTCCT CCCTCTCCCC GTCCCATCCC 4100
TGCACCCTTC CTCCCTCTCC CCGTCCCATC CCTGCACCCC TCCTCCCTCT 4150
GCTCCCATCC CACCCCTGCA CCCCTCCTCC CTCTGCCCCT ACCCCACCTC 4200
TGCACCCCTC CTCCTTCTCC CCATCCCACC CCTGCACCCC TCCTCCCTCT 4250
GCCCCTACCC CACCCCTGCA CCCCTCCTCC TTCTCCCCAT CCCACCTCTG 4300
CACCCCTCCT CCCTCTCCCC TCTCCCACCC CTGTACCCTT CCTCCTTCTC 4350
CCCGTCCCAC CCCTGCACTT CTCCTCCCTC TCACCCATCC CACCCCTGCA 4400
CCCTTCTTCC CTCTCCCCCA TCCCACCACT GCACCCCTCC TCCCTCTCCC 4450
CCTGTTCCAC CCCTGCACCC CTCCTCCCTG CCCCCAACTC CCATCCCACC 4500
CCTGCACCCT GGCCTGTCCT GACCTTTGCA CTCCCTCGAC CCAGGATGGG 4550 | Exon 3
                                                 D  G 92
CCCTGCACCC CAAGACGCTG CCTGGGCTCC CTGGTATTTC CACGGAAACT 4600
 P  C  T   P  R  R  C   L  G  S   L  V  F   P  R  K  L 109
ACAGGGCCGG CCCTCCCCCG GCCCCCCGGC CCCTGAGCAG CTGCTGAGTC 4650 | G4609A
  Q  G  R   P  S  P   G  P  P  A   P  E  Q   L  L  S 125
AGGCCCGGGA CTTCATCAAC CAGTACTACA GCTCCATTAA GAGGTGACAG 4700
Q  A  R  D   F  I  N   Q  Y  Y   S  S  I  K   R        140
CTTCCCGGAC GCCACAGCCT CCCTTGTCCC ACTGAGGCCC CAGAAACCCC 4750
GTGACGACCT TCCCATGACC CCCTCCCTTC CCAGATCCTA ACACCACGTG 4800
GGCCCCTCCC GCCCTCCCCC AGCACTTGCA CAAAGCCTGG AGGAGGGCCT 4850
CCCTGTCCCA CACAACTTCC TGCTTGTCCC CTTCCCACCC CTCTCCTCCC 4900 | A4887G
CAGGAGCGGC TCCCAGGCCC ACGAACAGCG GCTTCAAGAG GTGGAAGCCG 4950 | Exon 4
     S  G   S  Q  A   H  E  Q  R   L  Q  E   V  E  A 155
AGGTGGCAGC CACAGGCACC TACCAGCTTA GGGAGAGCGA GCTGGTGTTC 5000
E  V  A  A   T  G  T   Y  Q  L   R  E  S  E   L  V  F 172
GGGGCTAAGC AGGCCTGGCG CAACGCTCCC CGCTGCGTGG GCCGGATCCA 5050
 G  A  K   Q  A  W  R   N  A  P   R  C  V   G  R  I  Q 189
GTGGGGGAAG CTGCAGGTGC GGCTGGCCAG CGACTGAGAG ACCCGGGCGC 5100
  W  G  K   L  Q                                       194
TACCAAAAGG GGAGCGGGGT GGCGGGGCAG TTCCTAAGGC TTCCCGGGGG 5150
```

Figure 4 (Continued)

```
CTGGGAGGTC CCAAACTGTG GGGGAGATCC TTGCCTTTTC CCTTAGAGAC 5200
TGGAAAGGTA GGGGGACTGC CCCACCCTCA GCACCCAGGG GAACCTCAGC 5250
CCAGTAGTGA AGACCTGGTT ATCAGGCCCT ATGGTAGTGC CTTGGCTGGA 5300
GGAGGGGAAA GAAGTCTAGA CCTGCTGCAG GGGTGAGGAA GTCTAGACCT 5350
GCTGCAGGGG TGAGGAAGTC TAGACCTGCT GCAGGGGTGA GGAAGTCTAG 5400 | A5383G
ACCTGCTGCG GGGGTGAGGA AGTCTAGACC TGCTGCGGGG GTGAGGACAG 5450 | G5410A
CTGAGCGGAG CTTCCCTGGG CGGTGCTGTC AGTAGCAGGA GCAGCCTCCT 5500
GGAAAAGCCC TGGCTGCTGC TTCTCCCCCA AGAGAGAAGG CTTCTCCCGC 5550
CAGGCCAGTC CAGTGCACCC CCTCACCCAC ACCCACTGCT ACCCCAGTTC 5600
CCCTGCTTCG GCCCGCACCC TCCCTCACAC CCCAGCCCAC AGACTCGGGG 5650
CTGGCCTTAG TTACTGGAAC GCCTGTGACC ACAGCACTAA GAGAAGCAAG 5700 | A5659G
CTGCCCCATG GGGGACTTGG TCCCATGGCC TTGGCCTCCT TCACCATCAC 5750
TGGCCGCCAA AGAGTTTGAA ATAAAGCCAC GTGCCCAGTG AATCCCAAAG 5800
GAACCTCAAC TAAAATAAAA ACAATCCTAT CTGACACTTG CCTGACCCTC 5850
TAAGTCATTC AAAGCTTTAG CTCAACTTCG ATCCATCTGA GCTGCCATAG 5900
TGGACCCCAC TCAGAGCTGC GTCCCTCCCT TGACCCCAGG TTGGTCCCTG 5950
CCACTCCCCT GCCCCTGTCA CTGACACATG TTTCCTCCTC CCTCAGGCAG 6000
GAGTGGGACC TCCCAGCCTC CTCCTGGGGC CTCCACTCAG AATGTCAGGA 6050
TGAGCAGGGT CCTAGGAGGC CTCTGGTGCA GCCTTCCCTT CCCACCATCC 6100
ATGTGCTCAA AGAGAATCAC CCGTCCTTTC TTGAATGCCA TGGATCATGG 6150
GGGATTTGCT GCCCACACTC CTAGGCGGCC TCTTAGACAT CCGTTGGTGC 6200
CTAACCCAAG CATCAGTTTG GCAGAGGCCG AGTCCCTCCT CTGTACTGGA 6250 | T6237C; G6248A
TACCAAGTCA GCTTCCATAG GGATGGGGAG ACACCTGGCC CAGGGAGGAG 6300 | A6267G
ATGAGAAGCA GCCCGGATGG TGCTACATAT GTCAGAGAGC AGGGCAGGAA 6350
GGGATCAGTG TGGCTGCCAA TGGTCAGGAG GGCGCCATGG AGTGAACCAT 6400
GGCCCCTGCC TCCTCACCAG CAGCTCCTCT GGAGCTGATA CTCAAGACCC 6450
CCCGTCTCTC TCCTCACCCT CCTCTCCCGC TGCCTCGGCT GGCTCAGGTG 6500 | Exon 5
                                                  V   195
TTCGATGCCC GGGACTGCAG GTCTGCACAG GAAATGTTCA CCTACATCTG 6550
 F  D  A   R  D  C  R   S  A  Q   E  M  F   T  Y  I  C 212
CAACCACATC AAGTATGCCA CCAACCGGGG CAACCTTCGG TGAGTGCCCC 6600
 N  H  I   K  Y  A   T  N  R  G   N  L  R              225
CCACCATGCC AGGCCCCAGC CTTCTTCCCC AAGGCAGGGA AGGCGGGGCT 6650
CTGACCAGCT CTTTCCCCAT GCGTGCCAGC TCGGCCATCA CAGTGTTCCC 6700 | Exon 6
                                 S  A  I   T  V  F  P 232
GCAGCGCTGC CCTGGCCGAG GAGACTTCCG AATCTGGAAC AGCCAGCTGG 6750
 Q  R  C   P  G  R   G  D  F  R   I  W  N   S  Q  L   248
TGCGCTACGC GGGCTACCGG CAGCAGGACG GCTCTGTGCG GGGGGACCCA 6800 | C6779T
V  R  Y  A   G  Y  R   Q  Q  D   G  S  V  R   G  D  P 265
GCCAACGTGG AGATCACCGA GGTGGGCACC GAGGGCCACC CATGAGGGTG 6850
 A  N  V   E  I  T  E                                272
TCCCCAAGGT GGAGAATGAG GAAACCAGTG GGAGAAGGCT CGGGGGATCC 6900
AGGCAGGAAG AGGGGAGCCT CGGTGAGATA AAGGATGAAA AACACCAAAG 6950
GAGGGGTGCC TGGGTGGTCA CGGAGACCCA GCCAATGAGG GACCCTGGAG 7000
ATGAAGGCAG GAGACAGTGG ATGGACCGGT CCCTGAGGAG CGCATGAGGC 7050
TCAGCCCCAG AACCCCCTCT GGCCCACTCC CCACAGCTCT GCATTCAGCA 7100 | Exon 7
                                      L   C  I  Q  H 277
CGGCTGGACC CCAGGAAACG GTCGCTTCGA CGTGCTGCCC CTGCTGCTGC 7150
 G  W  T   P  G  N   G  R  F  D   V  L  P   L  L  L   293
AGGCCCCAGA TGAGCCCCCA GAACTCTTCC TTCTGCCCCC CGAGCTGGTC 7200 | G7164T
Q  A  P  D   E  P  P   E  L  F   L  L  P  P   E  L  V 310
CTTGAGGTGC CCCTGGAGCA CCCCACCTGA GCACCAAAGG GATTGACTGG 7250
 L  E  V   P  L  E  H   P  T                         319
GTGGGATGGA GGGGGCCATC CCTGAGCCTC TCAAGAAGGG CCTGCAAGGG 7300
GGTGCTGATC CCACACCCCA ACACCCCCAG GCTGGAGTGG TTTGCAGCCC 7350 | Exon 8
                                 L  E  W   F  A  A    325
TGGGCCTGCG CTGGTACGCC CTCCCGGCAG TGTCCAACAT GCTGCTGGAA 7400
L  G  L  R   W  Y  A   L  P  A   V  S  N  M   L  L  E 342
ATTGGGGGCC TGGAGTTCCC CGCAGCCCCC TTCAGTGGCT GGTACATGAG 7450
 I  G  G   L  E  F  P   A  A  P   F  S  G   W  Y  M  S 359
CACTGAGATC GGCACGAGGA ACCTGTGTGA CCCTCACCGC TACAACATCC 7500
```

Figure 4 (Continued)

```
 T  E  I   G  T  R   N  L  C  D   P  H  R   Y  N  I   375
TGGAGGTGAG GTGCGGGATG GGGCTCGGGC ACCGAATGCA CCTGTCCAAG 7550
L  E                                                  377
GCAGGAGTCT GGCTCTCACT CCATCCCCAA AATGCCAGCC ACGGGGACAA 7600
TCAGAGCAGG TCCAGGGTTG CCTCCTAAAT GGGAACTGAG GACAAGCTCT 7650
AGAACCACTG AAGCAAAGGG GTAGGGGGTG GCAGGGGTGT GTGTGGGGGT 7700
GTGAGTGGGT GAGTGTGAGA GTGTGGGTTT CTGGGGTGTG CAGTGGGTGA 7750
GAGTGTGGGC TTGTGGGGTG TGTAGTGGGT GTGAGACTGT GGGTTTGTAG 7800
GGGTGGGTGA GTGTGGGTGT GTGGGGGTAG GTGGGTGTGG GTTTGTGGGT 7850
GTGTATAGGC AGTGACTGTG AGACTGTGGG TTTGTGGGGG TAGGTGACTG 7900
TGGGTTTGTG GGGTGTGTAG GGGTGAGTGT GTGTGGGTTT GTAGGGGTAG 7950
GCGAGTGTGG GTTTGTGGGG TGTGTAGGGG TGAGTGTGTG TGAGTTTGTA 8000
GGGGTAGGCG AGTGTGGGTT TGTGGGGTGT GTAGGGGTGA GTGTGTGTGA 8050
GTTTGTAGGG GTAGGTGAGT GTGGGTTTGT GGGGTGTGTA GGGGGTGTGT 8100
GTGGGCTTGT AGGGGTAGGC GAGTGTGGGT TTGTGGGGTG TGTAGGGGCG 8150 | G8148A; C8149T
AGTGTGAGAG TGTAGGTATG TGGGTGTGAG TGTGGATGTG TGTAGGCGGT 8200
GAGTGTGAAA TTGTGGGTTT GTGGGGGTGG GTGGGTGTGA GTGTGTGGGT 8250
TTGTGGGTGG GTGTGGGTGT GAGTGGGTGG GTGAGGGGGG CATGGGGATG 8300 | G8275T
GGTGTGAACA TGTAGTTGTT CTTTCAGGCA TAGGACCCAT AGCTCTAGAG 8350 | A8347G
CTTTCATCAG ATTCTCAAAG GGGACCTTGA CTCGGAAAAG GTTAAGACCC 8400 | A8386C
ATTTTAGAGA TGAGAAATTA AAGCCTGGAG CTGAGGAGCG ACTGGCCCAA 8450
AGTCCCTCTC TGCTCTGAGG TGCCTTCGCA GGCAAAAACC TGAACCAGCC 8500
CCCTAGGCAG CCAGGCCTCC CAATGGACAC CACTCACCTC ACTCCTTCCA 8550
GCCATGTACG GGAAACAGAG ATAGTCTCCC CACCCCACCC CCGTGATCAC 8600
CTCTGTCCCT ACCGATGCCA CACACCCTTC TGCCCCAGGA TGTGGCTGTC 8650 | Exon 9
                                        D   V  A  V   381
TGCATGGACC TGGATACCCG GACCACCTCG TCCCTGTGGA AAGACAAGGC 8700
 C  M  D   L  D  T  R   T  T  S   S  L  W   K  D  K  A 398
AGCAGTGGAA ATCAACGTGG CCGTGCTGCA CAGTTACCAG GTGCAGAGGC 8750
  A  V  E   I  N  V   A  V  L  H   S  Y  Q             411
CCAGACTGGC CAGGAAGGCA AAGGGTTTGC ATACGGGGGC AGCAGGGGCG 8800 | G8785A
GGGGATGGAG GAGAGGCAGC CATTTAGAAA CTAGGGCAGG ATTTGGACAG 8850
GCAGAAGAAG TTCCGTAGTC CCAGTGCCAT GGCGCACACT GGCCTGCGGT 8900 | G8860T
TCGGGGACAG GGCAGGTACT ATTCCAGGCG CTGTCATCTG GTGGCTTACT 8950
GTGTGCCAGG GACCTTGCTG TTTACTGCAT GCCCAGTCAT GCTGATTCTC 9000
AGGGCATATT GGGTATTGCA GTTTGTGGGA CCCGCTGGAT CCTGGAAACA 9050
AATACCAGGA TCAAGGGCAC ACCAGGAGTC GTAGTTTGAG GAAGCCGGGG 9100
CCTGCTGAGA ATTTCTGTGG GCTATTTGGT TTGGGGACCA GGCATGCAGA 9150
TGCTGGAGAT TAGAGCTGCT TGTTGCATGT TGAACCTGCA GCATGACCAT 9200
GCATGATGTG GTTTGGGGTG AGGGTGACAT TGTGGTTTGA GGGGACACAG 9250
GGTGTGTTAG ATATGGGGTA ATCGAGGGCA CATGTGGTTT GGGGTGACCG 9300
GAGTGGTGGA GGAAGAATGG GCGAGGTCTG TGGGTCTGGT TTGAGCCTCT 9350
CCCCCTCTCT CTCCCTTCCA GCTAGCCAAA GTCACCATCG TGGACCACCA 9400 | Exon 10
                        L  A  K   V  T  I   V  D  H  H 421
CGCCGCCACG GCCTCTTTCA TGAAGCACCT GGAGAATGAG CAGAAGGCCA 9450
  A  A  T   A  S  F   M  K  H  L   E  N  E   Q  K  A   437
GGGGGGGCTG CCCTGCAGAC TGGGCCTGGA TCGTGCCCCC CATCTCGGGC 9500
R  G  G  C   P  A  D   W  A  W   I  V  P  P   I  S  G 454
AGCCTCACTC CTGTTTTCCA TCAGGAGATG GTCAACTATT TCCTGTCCCC 9550
 S  L  T   P  V  F  H   Q  E  M   V  N  Y   F  L  S  P 471
GGCCTTCCGC TACCAGGTGC CCACCCTAAC TGGCTCTGCC AGCCTGGGCC 9600
  A  F  R   Y  Q                                      476
CAGCTCTAAT TCTAAGCAGC CCCTGGGGAC CTCTAACCTT TCCTTTTCTT 9650
TACCTCCCCT CCCAACCCCA TCATCTCTCT GCAGCCAGAC CCCTGGAAGG 9700 | Exon 11
                                      P  D   P  W  K   481
GGAGTGCCGC CAAGGGCACC GGCATCACCA GGAAGAAGAC CTTTAAAGAA 9750
G  S  A  A   K  G  T   G  I  T   R  K  K  T   F  K  E  498
GTGGCCAAGT GGGTCCCCTG GGAGCCCCGC TCTCCCACAC ACACCCTGGG 9800
 V  A  N                                              501
GGCCCCACTC TCCCCCACAC ACCCTGGGGG ACCCTGCCCC AGCAGTGTTC 9850
TGGGCCTACC ACTCAGTATC CCAAAACCCT GTTGTGAGGG GGTTGGACCC 9900
```

Figure 4 (Continued)

TTGCCTGGGG AGGCCCTGCC TCTGTGCACC CGGGACACCC TCACACCTTC 9950 | G9932A
CTCTCCCGCA GCGCCGTGAA GATCTCCGCC TCGCTCATGG GCACGGTGAT 10000 | Exon 12
A V K I S A S L M G T V M 514GGCGAAGCGA
GTGAAGGCGA CAATCCTGTA TGGCTCCGAG ACCGGCCGGG 10050
A K R V K A T I L Y G S E T G R 530
CCCAGAGCTA CGCACAGCAG CTGGGGAGAC TCTTCCGGAA GGCTTTTGAT 10100
A Q S Y A Q Q L G R L F R K A F D 547
CCCCGGGTAG GGCTGAGCCC AGGGGAGCAG GGAGCTAGAA AGAGGGGGCT 10150
P R 549
CTATCAGCAT CTTCAGGGGT GCCCTGGAGG ACAGGAAGTG TTACAAGTCA 10200
GGACTCATGA GGAACCCGGA ACCACAGGTG TTCAGAGATC AAGTTGGGGC 10250 | A10213C
CTGAATCTTG CACTGCCAGG GAGGCCAGAG TGAGGAGGGC AGGGCCTCCG 10300
GGGGCCACAG CACCCAGGAC ATCTGTCTTC CCACCCACAG GTCCTGTGTA 10350 G10303T; Exon 13
V L C 552
TGGATGAGTA TGACGTGGTG TCCCTCGAAC ACGAGACGCT GGTGCTGGTG 10400
M D E Y D V V S L E H E T L V L V 569
GTAACCAGCA CATTTGGGAA TGGGGATCCC CCGGAGAATG GAGAGGTGAG 10450
V T S T F G N G D P P E N G E 584
AACTTCCAGG AAAGGGGCTG CTGGGAATGA GGAGAGACTC AGAATTGGAG 10500
TGACTGGGCA GGAACCTCTG CCCAACACAC ACACACACAC ACACACACAC 10550
ACACACACAC ACACACACAC ACACACACAC ACACACACAC ACACGCCAGG 10600
ATGGAAAGGG AGATGCTAAG AGACCCCTGG AGCCTGAAAC CCCACACAAG 10650
CTACGCTCCC AGCCCACCCA TGTGGCTGCC TCCCTGCAAG CACATTTGCT 10700
TAACTGCGCG TCCCCAAGTC ATTTCCATTA TCAGTGCAAG TTTTTAATAC 10750
AAGGAAGGCA CATCCTGGCT GACCAAGAGG TTAGACTGTG CTCGGGCACT 10800
GACAAGAAAA ACAGGGATAC GTCACTGAGG GCGGCTTCTA GGATGCGGGT 10850
AATGTTTCTT AATGGGATAC TGGTTACACA GGTGTGTTCA GTTTGTAAAA 10900
ATCCACAGAG CTGTACATTT ACAACATGTA CAACACTATT CCAGCATTTT 10950 | A10930G
ATTTTATTTG TTTTATTTAT TTTGAGAACC TATTTACGTT GCCCAGGCTG 11000 | C10987T
GCCTTGAACT CCTAGCCTCA AGAGATCCTC CTGCCGCAGG CTCCTTTTTC 11050 | C11034T
AAAAGAAGAA ATTGAGCGCT GTTTAGATGC CAACATAGAT TAAATAACTT 11100
CACTTTTTAA AAAGAAACAC AAAGCTAGAG TACCATCATT GAATTCCTTC 11150TCTTGCAAGC
TTAGGTATCT CTGAGGTGCC CCAGGCTAGG CTCATTTCTG 11200
AGTCTTACCT GCTCCAGCTT CTAGGTGTTA AAGGCCTTAT TAGCACTAAG 11250
TACTTCCTCA GTACTCTTTT TTCTTTTTTC CTTTGAGACA GGGTCTCACT 11300
TTGTGGCCCA GGCTGGAGTG CAGTAGTACA ATCACGGCTC ACTGCAGCCT 11350
CAACCTCCTA GACTCAAGCA ATCCTCCCAC TTCAACCTCC CAAGTAGTTG 11400
GGACTACAGG CGCATGCCAT GATGCCTAGC TAATTTTTGT ATTTTTTATA 11450
GAGATGGGGT TTCGCCATGT TGCCCAGGCT GGTCTCTAAC TCCTGGGTTC 11500
AAGCAATCCA CCTGCCTCGG CCTCCCAAAG TGCTGCGATT ATAGACGTGA 11550
GCCACTGCAC CTGGCCCTCA GTATCTTAAG CAAGTTGGAA TCTCGTGAAA 11600
CCCTTTTTGC TGCCTTAGTG TCCGTTTCAG CCCTCATTCT GACCTACCTT 11650
TTCAAGAAAA ATAGCACCAG CAATTGACTT TTTTTTACCA TAAAGCTGTA 11700
TAGACACCCA TATAACCTAC AGCCTTCACA AGGCATAGCA CATTTTCACC 11750
ACCCTGGAAA GTTCCCTCAT CAGTTCCTCA CGTGAATCCC TTCCCAGTCT 11800
GTCTCCCTGC CAGAAGTGTC TGTCACCACA GAATAGTTTC GCCTGCTCTA 11850
GAACGGCACC TAGATGGAAG CACGCAGTGT TGCGGCGTCT CCTGCTGAGG 11900
CTGTTTTTGA GGCGCACTCG TGTTGCTGCG TGACTCAGTA TTTCACTCAT 11950
TCTGCTGCTG AGTGCCGTTC ATTGTGTGAA TATCCCCAGT TTGTTTACCC 12000 | C11999A
ATTCTCTTGT TGGTGACACT TGGGCTGTTT CCAGGTCGGG GCTATTATGA 12050
ATAAACCTGT TATGAACATT CTTGTACCCG GCTTTTGTGG GCTTATGTTT 12100
TTATTTCTCT TGGGTAAATA CCTAGGAGTA GAATTGGTAG GTCATAGGGT 12150
AGATGCATGT TTAATCTTTC ACTTTTTTAA AAAATAAAAC TGCCAGGCCA 12200
GGCGCGGTGG CTCACGCCTG TGATCCCAGC ACTTTGGGAG GCCCAGGTGG 12250
GTGGATCACT TGAGGTCAGA AGCTCAAGAC CAGCCTGGCC AACATGGCAA 12300
AACCCTGTCT CTACTAAAAA TACAAAAATT AGCTGGGCAT GGTGGCGCAC 12350 | G12332A
GCCTATAGTC CTAGCTACTC AGGAGGCTAG GCGGGAGAAT TGCTTGAACC 12400 | G12351A
TGGGAGGTGG AGGTTGCAGT GAGCCGAGAT CACGCCACTG CACTCCAGCC 12450
TGGGTGACAG AGCAAGAATT CTACTTAAAA TAAAATACAA ATAAATAAAA 12500
TAAAACTGTC AAACAGCAAA GCAAATTAAA CTGCCCTTTA ACATCTGTGC 12550
AGTTCAATGT ATGTTAATTT TATCCCAAAT TTTTAACAAA TCTAGGAATA 12600

Figure 4 (Continued)

```
CAGCTCACAG AAAATGGGGT ATATTCACTA AAAATAAGGA ATATTTATAG 12650
CAAATTTGTT TGTAATACCC CACACTGGAA ACAATTCAAA TGACCATCGA 12700
CAAATACTGA TAAATTGTGG TATATTCAAG TGCCATATCG CACTAAGTGT 12750
GAACGAAACA CAACCACACA CAACAGTGCA GGTGAATCTC AAAAAATGTG 12800
AAGAGAAGAA AAAGCCAGAC CAAAGAATAC ATACTGTACT ACAGGGTTCA 12850 G12808A; G12836A
CTTTATATAA AGTTCAGAAA CAGGCAGAAC TAATCCACGG AGTTAGAAAT 12900
TAGGAGAGGA GTTAGTCACT GGGATGGGGG TGGCAGTGAC AGGAAGAAGG 12950 | G12911A
CACGAAGTTG GCTTCTAGGA TGCGGGTAAT GTTTGTTTGT TTGTTTGTTT 13000
GTTTGTTTTT GTTTTTGAGC TGGAGTCTCA CTCTGTTGCC CAGGCTGGAG 13050
TGCAATGGCG TGATCTCGGC TCACTGCAAC CTCCGCCTCC CCGGTTCAAG 13100
CGATTCTCCT GCCTCAGCCT CCCGAGTAGC TGGGATTACA GGTGCCCGCC 13150 | G13124A
ACCATGGCCA GCTAATTTTT GTGTTTTTAG TAGAGACGCG GTTTCACCAT 13200
GTTGGCCAGG CTGGTCTTGA ATCCCTGACC TCAGCCTCCC AAAGTGCTGG 13250 | G13244A
GATTACAGGC GTGAGCCACC ACGCCCAGCC ACGGGTAATG TTTCTCGATG 13300 | C13272T
GGATGCTGGT TGCACAGGTG TGTTCAGTTT GTGAAAACTT ACAGAGTTGT 13350
ACATTTACAA CATGTGTGCA CCTCTGGACT TGTGTTGCAC GTTGACAAAA 13400 | G13384A
CATTCAAAAA TGAAATTCAA ATCGTTCTTG CTAACTCTGG CGCACTTGGG 13450
AACCAGCACC CAGAGGCATC TGCAGTTGAG CACCAGATGC AGTTCCTTCC 13500 | A13485T
AGCTTCCTTC CCCCTGGGAG GTCCGCTTGA TGCCACTTCT TCATGGCAGC 13550
ACAAACAAGG CCATGGTCTT CTGAGGAGGG CAACCTGCAC AATGTCTGCT 13600
AGTGACCAGG ACACTGCTGA AGGAACTGAG AGTTTGTCCA CCCATGAAAT 13650 | A13644G
CCACTAAAAC AGGAAAGATT TGCTCTAGCC CGTTGTTAGC CAGGAGTGAG 13700
CAAAGAGCTG TGCCCTCCCC TGCAGCTGCG AGGACGATCT CCCTGCCCCA 13750
ACAAGTGGGG ATTCAGCAAC TCCACTTCTA AGGATTACCC AGCTGAAGCA 13800
TTTAAAAGTG GGAGCAAGGC ACACGTACAA GGGCGTTTGA GAGAGCACCT 13850 | C13834A
GTTCCCAGAC CACCGAGCTG CCCTTCAGTC TCAGTGAAGT ACAATGTAGC 13900
CACTAAAAAG ACTGAGGTCA TGTTTTGGAA AGTCCAGGCC GGAGGATCGC 13950
TTGAGCCCAG GAGTTCAAGG CCAGACTGAA CAACACAGCG AGACTCCATC 14000
TCTTCAGAAA ATTTAAAAAT TAACCAAGAG TGGTGGCACG CACCTATAGA 14050
TCTAGCTACT AGGAAGGCAG AAAAATCCCT TAAGCCCAGG AGTCTCACCT 14100 | C14094T
TACAGTGAAT GATGATGGAG CCACTGCACC CCAACCTGGG CGACAGAGCA 14150
AGACCCATAT CTAAAAACAA TACTACTACT TACGTCAATA TTGTTGTATT 14200 C14183T; G14184A
GACCTGGAGG GATGTCTGCA ATAAATTATT GATTAAAACC AAGGAAGTAC 14250
AGTATGGTAC CACTTTTACT TAAAAAAAAA ACTATAAATA TGCACATGCA 14300 A14281; A14296G
CGTAAGTTCA AGGAAAAAGG GCTGGAAGGT TAACACCTGT CAATGGCGCA 14350
TATGCCCGGA GGGAAGATGG GGTGGTCTTT GTCTTATCAC TTTACACATT 14400
TCTGTAATGT CATTTTTCAA AAACATCAGA TCGCTTTTGA AATTTTCAAA 14450
ACAAATAAAA ATTAAGTTAC AAATCAATAA TAATGAGGAT CAGCTGGTAC 14500
AGTTTTAAAC TTCTATGTAG TTTGAAATGA AACAAAACTA ACCCTGATGC 14550
AAACACTCCC CTCGCCAGAG CTTTGCAGCT GCCCTGATGG AGATGTCCGG 14600 | Exon 14
                    S   F  A  A   A  L  M   E  M  S  G 595
CCCCTACAAC AGCTCCCCTC GGCCGGAACA GCACAAGTGA GTTGGGTGAG 14650
 P  Y  N   S  S  P   R  P  E  Q   H  K                607
AGTTTGGGGG AGCTGGGGGA GCTGATGCAT TTGGAGACAC AAACAGAAAG 14700
GGGGTCTGAA AAGCTCTCCC TCTGTGCCTC AAGTCGTTTT CCCACCAAAA 14750
GCCAGGGCTC CAGGATGCCC TCCATTCCAG GCTGCAATGG CAGTCCTAGA 14800 | T14797
CCTGCCTGCT TCTGAGAGCC GGGACAGTCC TGAGGTCTTC AGAGATGGGG 14850
GTGTGGTGTG TCAGGGCCCC AGGCTCGGAA CCCCAGGGAT GCTGGCCCTC 14900 | G14877T
AGCCCCTCCC AAGGGCAGGG CCTTTCCTGT CCCAGAGGCA GAGACCCTGA 14950
AGCCGTCCCT GGGGCTGGGG CTGGGCCTAG CCTGTATCCC CAGGGCCCTG 15000 G14970T;
T14983ATGACAACCTT GTCTTTGTCC TCTCTTGCCA GGAGTTATAA GATCCGCTTC 15050 | Exon 15
                                       S  Y  K   I  R  F 613
AACAGCATCT CCTGCTCAGA CCCACTGGTG TCCTCTTGGC GGCGGAAGAG 15100
 N  S  I   S  C  S  D   P  L  V   S  S  W   R  R  K  R 630
GAAGGAGTCC AGTAACACAG ACAGTGCAGG GGCCCTGGGC ACCCTCAGGT 15150
 K  E  S   S  N  T   D  S  A  G   A  L  G   T  L  R   646
CAGGGCCTCA CCAAGAGGGG TGCAACGGGT GGGCAAGCTG CCTGGGCAAA 15200
CGTGGCCTGC AAAGGGAGCT CCACTGACGA CCCCTGCACC CCAGGTTCTG 15250 | Exon 16
                                                F  C 648
TGTGTTCGGG CTCGGCTCCC GGGCATACCC CCACTTCTGC GCCTTTGCTC 15300
 V  F  G   L  G  S   R  A  Y  P   H  F  C   A  F  A   664
```

Figure 4 (Continued)

```
GTGCCGTGGA CACACGGCTG GAGGAACTGG GCGGGGAGCG GCTGCTGCAG 15350
R  A  V  D   T  R  L   E  E  L   G  G  E  R   L  L  Q  681
CTGGGCCAGG GCGACGAGCT GTGCGGCCAG GAGGAGGCCT TCCGAGGCTG 15400
 L  G  Q   G  D  E  L   C  G  Q   E  E  A   F  R  G  W 698
GGCCCAGGCT GCCTTCCAGG TGAGCCCAGC CCAGCCCCTG CTCTGACTCC 15450
 A  Q  A   A  F  Q                                     704
TGCCCCCTGG GATGCCTCCT CCTGCCTCAC TCTGCCCTGA TTCTGTTTGG 15500 | C15455A
TTCTTTGGTC CCTTCCTGTT CCTTCCAAAA TCCACCCTCA TCTCTCCATG 15550 | A15534G
GCATAGCCAG CTCTTCTGGG TCAGGGGCAG AGGATGACAT GGCCCTGCCG 15600
ACCACAGGGG TGCCTAGCCC AGGCAGAAGT GCAGCCGAAA GAGAGCAGGC 15650
AGGGCCCTGG CAGGAGGGAG CTTCAGCCAG GCACAGGCTG GGCCTCACAA 15700
GTGGGCGCAC AAAGGGAGGG GGTGCAGGGC AGGGCAGGGG ACCCCACCCA 15750
GGATGGGCAG GATGGAGGGA GAAGGAAGGG ACAGAGAGAA GGTCAGACAG 15800
AGGCAAGGGC TGAAGCTGAG GCCAGCACAG AAGCCACAGG AAGCCAGAGG 15850
CCAGACAGCC TGGGGCGGTG CCTGCACCGC AGAACTGGTC CCGGGCCGGG 15900 | G15898A
CAAGCAAGCA CAGGGAGAGG TGGATCCCTG GGGGCTGTGG CTTTTTAAGC 15950
CTGGGCTTCC TCAGGGGCAG TGCTGCCTGT CTGGGGATCA TGTCTGCAGT 16000
TGACAAGGGC TCGGTCTCCC CAGTGCCACA CTCTTCAGGG CACTGCTGCT 16050
GTCCCGGGGC CCAGGCTGGA GCTCAGCAGA TTTGCCTTGA TTGGAGGAGG 16100
AGGGCATCCT AGGAGGAGAG GGAGTGGGGG CTACCTCAGG GACGGGGAGG 16150
TCAGGCTGCA GAAACACATA GGCCCTGATT GGGAAGAAGG GAACGGAAAA 16200
TAAGACTTAA AGAATTTAAA CAAAAAGAGC CATTGCAGCG GGATGAGACC 16250
ACATCATCAG GTTTTGGGAA TAGGACTTTA GAGGCGTAGG ATCCATTACA 16300 | C16255
GCATCACCGA ACCAGAAGCA GGAAGGCTGA GCTAAGCAGA GCAGCAGCAG 16350
TGGAGATAGG AAGGAAGGGA GGGAGGGGCC GAGGAAGGAA GGAAGAGATA 16400
TAAGACTTCA CACGCACCAC AAAAGAAAGA TTAACGGGAC TTGGTGATAT 16450
GAGGCTCAGC CAATCACGGG TGAGCCCTGC ATTTCAAGCC TGGGACTGGC 16500 G16468C; G16499T
CCAGCAGTTT TCCAGCTGTG TGCCTGACCA GGAGTAGACG GGATCCACAC 16550
CCTCCCAGGG ATCTGCCCCG TGGGGTCCCC TCTGCCGCCC GAATTGTGCG 16600
TCCCTTCCCA GGAGCACTTA CTATCTGCAC GCACTTTGTG GAAAGCTAAG 16650
GGCTTTACAT AAAGTATCTC ATTTAATCTT CACCAGAACA CAATGAGGTG 16700 | T16665C
TAAAGATGGG GAAACTGAGG CATGTCACTG TAAGTACGGG ATTCGGAATT 16750
TGAATGCAGG TCTGAACACA CAGACGCCTT CACAGAGCTA CCGTGTGCCA 16800
AGCACTATGC TTCTCGGATC ACGGGATTAA CACGCACCAG ATAAGGAACG 16850
ATGCACCAAT CAGGACGTGC AGAGAAAGAG CCAGCCGGGT CCCTGGGCCC 16900 | G16897A
AGCGGCCAAT CCATGAAATG GGCTGGCGGA AAAGGTCCTG TCCTTGGCGC 16950
CGGCCTCAGC CACTGGGGCT GCCAACCCCC CAGGAGCAAG ACGCAGTGAA 17000 | C16981A
GCCGCCCAGG CGCCTCACTA GGGCGACCCC TGGTGGCGGG GAGGTCCTCA 17050 | G17041
GCCCTCACCG GCCTGTCCCG CAGGCCGCCT GTGAGACCTT CTGTGTGGGA 17100 | Exon 17
                         A  A   C  E  T  F   C  V  G  713
GAGGATGCCA AGGCCGCCGC CCGAGACATC TTCAGCCCCA AACGGAGCTG 17150
 E  D  A   K  A  A  A   R  D  I   F  S  P   K  R  S  W 730
GAAGCGCCAG AGGTACCGGC TGAGCGCCCA GGCCGAGGGC CTGCAGTTGC 17200
  K  R  Q   R  Y  R   L  S  A  Q   A  E  G   L  Q  L  746
TGCCAGGTGG GCCCTGCCCT CACCCTAACC CGGCTGGTTC TCTGAGGCCC 17250
L  P                                                   748
CCACACCCCG GGACTAAAGC ACTCTGGGGC CAGGCCCTGC TCCCTAGCTC 17300
AGGCTGCCTC ATTTGCCCCT CCCCGCCCCC AGGTCTGATC CACGTGCACA 17350 | Exon 18
                                  G  L  I   H  V  H  754
GGCGGAAGAT GTTCCAGGCT ACAATCCGCT CAGTGGAAAA CCTGCAAAGC 17400
R  R  K  M   F  Q  A   T  I  R   S  V  E  N   L  Q  S  771
AGCAAGTCCA CGTGAGGACG ACGGCTTTAC CGCCCCCCAA CCCCTGTCCT 17450 C17433A; A17439C
 S  K  S   T                                           775
GAACACCCTG ACCCTGGACC CTCCTCCTCC CACATTCTCC CGCCCCCACC 17500
CCTCTCTGAC TCCCCATAAG TGCCCCTCTC CCCACCCCCA GGAGGGCCAC 17550 | Exon 19
                                              R  A  T  778
CATCCTGGTG CGCCTGGACA CCGGAGGCCA GGAGGGGCTG CAGTACCAGC 17600
 I  L  V   R  L  D   T  G  G  Q   E  G  L   Q  Y  Q  794
CGGGGGACCA CATAGGTGTC TGCCCGCCCA ACCGGCCCGG CCTTGTGGAG 17650
P  G  D  H   I  G  V   C  P  P   N  R  P  G   L  V  E  811
GCGCTGCTGA GCCGCGTGGA GGACCCGCCG GCGCCCACTG AGCCCGTGGC 17700 | G17696A
```

Figure 4 (Continued)

```
A  L  L   S  R  V  E   D  P  P   A  P  T   E  P  V  A  828
AGTAGAGCAG CTGGAGAAGG GCAGCCCTGG TGAGGGGCAG CCTGGGAAGC 17750 | G17749A
 V  E  Q   L  E  K   G  S  P                          837
AACAGGGCAC ACCAGCCCCA TGCCCAGCCC CACCCCCGGC CCCAGGCCTC 17800 | C17797A
CAGGAGCTCA GGACCCGACC CAGGGGGTGG CCACCTCCTC CACAGCTCAG 17850
CAGGCAGGCT CAGAGCTGGC TGTGCTGCCC ACTGCCGGGC TGGCCTTGTT 17900
GCTGGACCAT CCCCACACCC TCAAATGCAC CCCCACCAAA AGGCTGTCCC 17950
CTCCCTCTGG GCTCCTCTCC AAGGCTCCCC TAGCAATCTA GCTTGCTCTG 18000 | A17971G
GAGCTGGCAC TGGGGCTATT TGCTGCCACA TCAATGCCTG GGCTTTATTT 18050
AAAATAAGGG GGTGGAGTCA GAGGCAGAGG AGCCCAGACC AACCCAGTCC 18100
GGCCAGGGGC CCCCGAACAA TACACTGAGG CTACCTAGAC AGGCCGACCC 18150
CGCTGCTCAA GGGCAGGCTC TCTAACAGTC ACCAAAACAC AAACATCAGC 18200 | T18173C
CCAGGTACTG CAGTCCTGCT GGGCCCTGTC CTCAGAGCTC CCTGTGCACT 18250
ATCCCCAGGT GGCCCTCCCC CCGGCTGGGT GCGGGACCCC CGGCTGCCCC 18300 | Exon 20
           G   G  P  P   P  G  W  V   R  D  P   R  L  P  851
CGTGCACGCT GCGCCAGGCT CTCACCTTCT TCCTGGACAT CACCTCCCCA 18350
P  C  T  L   R  Q  A   L  T  F   F  L  D  I   T  S  P  868
CCCAGCCCTC AGCTCTTGCG GCTGCTCAGC ACCTTGGCAG AAGAGCCCAG 18400 | G18400T
 P  S  P   Q  L  L  R   L  L  S   T  L  A   E  E  P  R 885
GGAACAGCAG GAGCTGGAGG CCCTCAGCCA GGTTGGGGGC CACCCCAATG 18450
 E  Q  Q   E  L  E   A  L  S  Q                      895
AGGCACAGGG GCTAGAGAGA CGGGATGAGC TGGGGGGACC CCAGTGGCAG 18500
GAAACCCCCA TGCAAAGTCC CCCCTGGACT TTCTTCTCCT GGCTGACATG 18550 | T18544C
CACTGGTGCT TTAAGACCCA GCTCCTCAGG GAGGAATTCA TGGCTGGATT 18600 | G18581T
CTCCAGGTCT TAGAGAAAAC TCTATTGGCC TGAACTGAGC AGGGAGAAAC 18650
CCTAAAGAGG CTCAGTGGGG GAGGGGTCAA GAAGGGAGGT TACTAGGAAG 18700
GCCTATCGGG CCTCCAACCC ACTGCATCCT GCCCCGCCAG GATCCCCGAC 18750 | Exon 21
                                             D  P  R   898
GCTACGAGGA GTGGAAGTGG TTCCGCTGCC CCACGCTGCT GGAGGTGCTG 18800
R  Y  E  E   W  K  W   F  R  C   P  T  L  L   E  V  L  915
GACCACTTCC CGTCGGTGGC GCTGCCTGCC CCACTGCTCC TCACCCAGCT 18850
E  Q  F   P  S  V  A   L  P  A   P  L  L   L  T  Q  L 932
GCCTCTGCTC CAGCCCCGGT ACTACTCAGT CAGCTCGGCA CCCAGCACCC 18900 | C18893T
 P  L  L   Q  P  R   Y  Y  S  V   S  S  A   P  S  T   948
ACCCAGGAGA GATCCACCTC ACTGTAGCTG TGCTGGCATA CAGGACTCAG 18950
H  P  G  E   I  H  L   T  V  A   V  L  A  Y   R  T  Q  965
GGTGAGGCAA CAAGCAGGAG CAGGCCTGGC CACAGCAGGG TTGGGACCGG 19000 | G18999A
CCCCTCTCTG GCCCCTCACC GGCCTCTCCT TCCCACCCCC AGATGGCGTG 19050 | Exon 22
                                             D  G  L   968
GGCCCCCTGC ACTATGGAGT CTGCTCCACG TGGCTAAGCC AGCTCAAGCC 19100 | A19091T
G  P  L   H  Y  G  V   C  S  T   W  L  S   Q  L  K  P  985
CCCACACCCT GTGCCCTGCT TCATCCGGGG GTAAGTGAGA TGGAGGACTT 19150 | G19145A
 G  D  P   V  P  C   F  I  R  G                       995
GGTGGGGAGC TGCCCAGGGT CAGGGTGGCA GCTTTGGTGA GGAGTGTCAC 19200
TGGTGAGGGG TGTCACTGGA AACAGGAAGG AGCTCTGTAA CATGTCAAGG 19250
GTGTGGTGTC ATTAGGTCAC TTCAGAACTC TGGCTAAGCT TTGGCTCTCT 19300 | G19258A
CATTCATTTA GACTCAGAGT TCTGCCCTGA AACTATAGCT CCCAGAGCCA 19350
GAGCTGGTAT CAAACCGGCT GGCCCTGTGG CTTTCTGAAA GCTTCTGTGT 19400 | T19358G
TCCTCTCTAT GTCCCTGGGC TGTCTGATGT TGGGCAGCAT GGCACCTGGG 19450
AACTACAGTC ACTAAATCCT CACTCAATCC AGGGAGAACT ACTAGTTAGG 19500
GTTAAGACCA CCCTTTGGCC TTGGTGTCAC CAAGGACTCA AAGAAGGTGA 19550 | T19516
AGGTTTTGGT TTTTTTTTCC CCCAGAGATG GAGTCTTGCT CTGTCGCCCA 19600
GGCTGGAGTG CAGTGGTACG ATCTCGGCTT ACTGCAACCT CCGCCTCCCG 19650
GGTTCAAGAG ATTCTCCTAT GGCGTGAACC TGGGAGGTGG AGCTTGCAGT 19700
GAGCCAAGAT TGTGCCACTG CACTCCAGCC TGGGCGACAG AGCCAGACTC 19750
TCTCTCAAAA AAAAAAAAAA AAATATTCTC CTGTCTCAGC CTCCTGAGTA 19800 A19772T; A19773G
GCTGGGATTA CAGGCACCCA CCACCACGCC CAGCTAATTT TTGTATTTTT 19850
AGTAGAGACG GTGTTTCACT ATGTTGGCCA GGCTGGTCTC GAGCTCCTGA 19900
CCTCACAATC CTCCCACCTC CGCCTCCCAA AGTCTTGGGA TTACAGGTGT 19950 | A19907G
GAGCCACCGC GCCCGGACCG AGGGTGAAGG ATTTTAAGAG ACCCTTCCTT 20000 |
G19980ACATGCTGTGT CCAGAAGTCT TGCCCGCTCT CGCAGCCAGG AACCAAAAGT 20050
```

Figure 4 (Continued)

```
CCTGGTAGGA CTGAGAACAG TTCCTAGGCT GCCATCAGCT GGGCCTGGTG 20100
ATTCAAATCC ACCCAGGTGG CTAAACTACA AATAAACCGT ACCCATCTAC 20150
TGAACATAAA CTAAATACCA CTATTAAGGA TACTTAAAAT AAACACACTT 20200
AGTGAACCCA TTATGAACTG AAAGTGTCTT TCACCCTTCC CACGTTTTCT 20250
AAATCCCCTG AGTCATCTAA GTATTCTTCA ATCCAAAATG AACTATATTT 20300
CCTTTGGTGC AATCTCCAGA AACCACAGAT CCAAGGAGTT TCAGCAAGTA 20350 | G20348A
GAGTTGTTTT TTGTTTTTTG TTTTTTTTTT AATTTTTTTT TGAGATGGGA 20400 | A20352C
AGAACTTGGG TCCTCCTTGC TCCACCCACC CTGCATGGTG AGAATGGTGG 20450
AGCAGGAAAG GCAAAGGGGA CCTGATGGAG TGTCTCTCCT GCCAGGGCTC 20500 | Exon 23
                                                 A   996
CCTCCTTCCG GCTGCCACCC GATCCCAGCT TGCCCTGCAT CCTGGTGGGT 20550
P  S  F  R   L  P  P   D  P  S   L  P  C  I   L  V  G  1013
CCAGGCACTG GCATTGCCCC CTTCCGGGGA TTCTGGCAGG AGCGGCTGCA 20600
 P  G  T   G  I  A  P   F  R  G   F  W  Q   E  R  L  H 1030
TGACATTGAG AGCAAAGGTG AGGCTGGGGA CTAAAGGACT GCCTGAAGGG 20650 | G20628T
  D  I  E   S  K                                     1035
AGTCACACAA TCTAGGGACA GAGGGGTGGG GCTGGAAGGC AGGAAATAGG 20700
AAAGAGAGGG CAGGAAACAA AGTCCACAAA GCTGAAAAGA CGCTCATGAG 20750
ACCAAGGGGA GGGCAGGTAC CAAAGGCAAG GGCTGGGCCC TGAGCTTCTG 20800
GCTTCCTGGT GCCTGGTACA TAGTAGGTGT TGACTGGATT GAGGACAAAG 20850 | C20819T
GAAAATAGAA TTTTCAAAGG GATTAGGGCT AAGACTCAAA GAAGAACTGC 20900
CCAAGGTGGA TTCTTGACTG TGCCAGAGCT GACCGAGGTC TGTCCAAGAC 20950
CTAAGGATGC TACAAGGTGT TCATATTGAG CATGGGGTGC CCAGGGTGGT 21000 | T20961C
CTGTCAATCA AAAGAAGAGG GCTGTGACTG GGAGGAGAGT TATAAGTATG 21050
GGAGAATATG AAGTGGGAGC GGGGAAGGGG ACTGCGATGT CACACAATGC 21100
AAAGGGCATG GAATTCTGAG TCCGAAGCCG CGCATTCTAG CGCAGCTCCA 21150
CCAGGGGCCA CCACCTCACC CGCGCTTCCC TTCCCTCTGT AAATCAGGGC 21200
TGTGCAGGGT CTCTGTGAAA GCATTCTACA CTCTCTTAGA GATGAAACAG 21250
CCAAAGTAAT GGTGGTTTCA GCCCAAAACG CTGGGCTGCC AGGCTGGGCG 21300
ACGGTGGCCT GTGGGGAGGC CCCACTAGCA CTGTGCCCCG GAGAAGAGCC 21350
TTCCCAAGCG CGGGGTTGCT TGCAGGGCTG CAGCCCACTC CCATGACTTT 21400 | Exon 24
                          G  L   Q  P  T   P  M  T  L 1044
GGTGTTCGGC TGCCGATGCT CCCAACTTGA CCATCTCTAC CGCGACGAGG 21450 | G21449A
 V  F  G   C  R  C   S  Q  L  D   H  L  Y   R  D  E   1060
TGCAGAACGC CCAGCAGCGC GGGGTGTTTG GCCGAGTCCT CACCGCCTTC 21500
V  Q  N  A   Q  Q  R   G  V  F   G  R  V  L   T  A  F 1077
TCCCGGGAAC CTGACAACCC CAAGGTGTGA GACCCTGAGG GCGCAATGGT 21550
 S  R  E   P  D  N  P   K                             1085
AACCTGAAGA TAGGGAGAGA GGGGAGGACT CGCGCTCTCC AGCGGGGCAC 21600
ACCAACCACG GCCCTCCCGT GGCCTCCCAC GACCACTCAG CCACCCCTGC 21650
ACACTCTGGC CCACCCTTGT GCCCCGGCCC CTCTAGGCCC GCCTCCTCCC 21700
GCCCCTGCCC CGCCCCTTTG GCTCTGCCCC TGTTGACACC GCCCCAGGGC 21750 G21741A; C21742A
ACGCAGGCCC CACCAGGCCC GCTCCGGAGA CTTTCACGTC CAGGGCCAGC 21800
CAGCAGCCCC GGGCTGCGCC CCCGCGCCCA CCCCCACCAG GGCCCGCCCT 21850
AACCCCGCCG CCCCGCAGAC CTACGTGCAG GACATCCTGA GGACGGAGCT 21900 | Exon 25
                   T   Y  V  Q   D  I  L   R  T  E  L 1096
GGCTGCGGAG GTGCACCGCG TGCTGTGCCT CGAGCGGGGC CACATGTTTG 21950
 A  A  E   V  H  R   V  L  C  L   E  R  G   H  M  F   1112
TCTGCGGCGA TGTTACCATG GCAACCAACG TCCTGCAGAC CGTGCAGCGC 22000 | T21964C
V  C  G  D   V  T  M   A  T  N   V  L  Q  T   V  Q  R 1129
ATCCTGGCGA CGGAGGGCGA CATGGAGCTG GACGAGGCCG GCGACGTCAT 22050
I  L  A   T  E  G  D   M  E  L   D  E  A   G  D  V  I 1146
CGGCGTGCTG CGGGTGCGGA GGGGCGGGCC GGGCCTGAGC GTGCGGGGTT 22100
 G  V  L   R                                         1150
CCTGCTAAGG TCTCCGAGTC GGGTTCTGAT CCACTGTGCT CTTTTCCGAC 22150
AGGATCAGCA ACGCTACCAC GAAGACATTT TCGGGCTCAC GCTGCGCACC 22200 | Exon 26
   D  Q  Q   R  Y  H   E  D  I   F  G  L  T   L  R  T 1166
CAGGAGGTGA CAAGCCGCAT ACGCACCCAG AGCTTTTCCT TGCAGGAGCG 22250
Q  E  V   T  S  R  I   R  T  Q   S  F  S   L  Q  E  R 1183
TCAGTTGCGG GGCGCAGTGC CCTGGGCGTT CGACCCTCCC GGCTCAGACA 22300
 Q  L  R   G  A  V   P  W  A  F   D  P  P   G  S  D   1199
```

Figure 4 (Continued)

```
CCAACAGCCC CTGAGAGCCG CCTGGCTTTC CCTTCCAGTT CCGGGAGAGC 22350 | UTR
T  N  S  P                                             1203
GGCTGCCCGA CTCAGGTCCG CCCGACCAGG ATCAGCCCCG CTCCTCCCCT 22400
CTTGAGGTGG TGCCTTCTCA CATCTGTCCA GAGGCTGCAA GGATTCAGCA 22450
TTATTCCTCC AGGAAGGAGC AAAACGCCTC TTTTCCCTCT CTAGGCCTGT 22500
TGCCTCGGGC CTGGGTCCGC CTTAATCTGG AAGGCCCCTC CCAGCAGCGG 22550
TACCCCAGGG CCTACTGCCA CCCGCTTCCT GTTTCTTAGT CGAATGTTAG 22600
ATTCCTCTTG CCTCTCTCAG GAGTATCTTA CCTGTAAAGT CTAATCTCTA 22650
AATCAAGTAT TTATTATTGA AGATTTACCA TAAGGGACTG TGCCAGATGT 22700
TAGGAGAACT ACTAAAGTGC CTACCCCAGC TCATGTGGAT TACAGTTTTT 22750
TTTTTTTGTT TTTTTTTTTT TGAAACGGAG TCTCCCTCTG CCGCCCGGGC 22800
TGGAGTGCAG TGGCGTGATC TCAGCTCACT GCAACCTCCA CCCCACAAGT 22850
TCAAGTGATT CTCCTGCCTC AGCCTCCCAA GTAGTTGGGA TTACAGGTGC 22900
CTGCCACCGC GCCCGGCTAG GTTTTGTATT TTTAGTAAAG ACGGGGTTTC 22950
ACCATCTTGG CCAGGCTGGT CTTGAACTCC TGACCTCGTG ATCCAACCGC 23000
CTCAGCCTCC CAAAGTGCTG GGATTACAGG TGTGAGCTAC TGCACCCGGC 23050
GTGGATTACA ATTATAAAAT GACAAGATTT CTGTTTTAAC CTGTGCAGTT 23100
GTGGGTATGT GGTGGGGAAA GGGGTCATTC TTTTGACAGA GTCCTACACG 23150
CCACTTGACC CTGCACTCTG AAAACATGGT TTCCAGCCAG TCTGGGCTGC 23200
TCCCCCGTGC AGTTCTCAGG CTCGTGATCG AGAAGGCAGG TGCAGCACTC 23250
AGCTGCCAGG AGTGGGGCCT GCCAGAAACA AGAGTCACAG AGATGTGCAA 23300 | C23288G
CAGCCATGAG CAAGCTTTAC TGCTTATTTC ATACAGGATG GGGAGCCACA 23350
CCCACTTCCT GGGACATCAC ACCCGTACTG AAGTCCAAAA ACATCATCCC 23400 | G23375C
TCCCGTCTTT CCACTGACAA GTCCCCATCC CCTACAAGCC CCAAGGAACC 23450
TGAAAGTGCT GCTGGCAGCC GCCAGCATGA CGAATCCACA GCCTTAAAGC 23500
CCACCTGCCT CACTGTCGCC CTTCCATTTA GCTCGGCCTC ATCCTTGACC 23550 | C23534T
TCTGTCCCCC ACCTTGAGGA AACTCGAGGA CTTCTTCCCA GGCAGCTGCT 23600
CCAGGACACA TTCCAGTTGG GGATGTCTCC CCTTATTCCC TCTGGGTGCA 23650
GACCATCTCT AAGACTTGTT TCCAGATGCC ATCAGCATCT CCTCTCCTTG 23700 | A23684G
CCTACCTTTT CTCTGTTCTC GGGGCGAGTT CCTCACTGAC TCCCAGGTCC 23750 | G23721A
TGCCCAACTA AAGCACCTGG GCCTGTCATC TATGGGGCCT CTAACAATGA 23800 | C23791G
CTCCTTGTGT TTTTCTACTC CACCCTCCAA TCTCCTGTGG CTGCCGAAGC 23850
CAGGGTACCT GTGGGAGGAG ACGGCTCTTG GCAAGCAGTC CAGGGGTCTA 23900
GATTCCAGAG ATGACCACCT CCCATCACCC CAAATTCCCA CCACTGCTCC 23950
CATCGCTTCA AGTCGGACTC CAAACCAACT ACCTATGCCG TCCTTTCTCC 24000
CTCCCCTCAC AGGAGGCAAT ACTGACCCTG AGGAGTCGTC TCAGTCAGTG 24050 T24023C; G24038A
CAAGAGGCCC GGTCAGGCTC CTTCTGGGTG TCTGTGGTCA CCTGAAACCC 24100
TCCGGGGAAC AGATTCCGGG CCTTCTGGGT TCCCCACTGT TGTCTGGGGC 24150
TAGAGGCAGG ACTGGAGCCT GGTGAAAAAG GCCATCAGCT GGGCAGTTCC 24200
ATGATGCCCA GTGTCCACCA GGCTCTGTCC CCTGCAGGCC CCACCCTCCT 24250
CACCGTCACT TGACCAGGAT GGCTTCTCCT CATCAGGCGA GGGTGGCTGT 24300 | C24288T
GAGGGGCTGG AGCAGGGCCT GGACAGGATG GAGGCTGCAG CCTCACCCCA 24350 | G24327C
CGGCTCCTGC TGCTGCTGCT GCTGGTGAAG CTGCATGCAA AGGAGGAGGA 24400
ATGAGGGCTG CACCCCAAGG AGGGCAGGGC CAAGCACCTG GGCTAGAGGC 24450
AGAGGGCTTT TCAGCCTCCT CCTGCCACTC TGCTAGACCC TTCCGTAGAC 24500
TCCACCCCAC CTCAGTCTCC ATGTTGTTCA CCTGCCTTCT CTCCACATTT 24550 | C24513G
CTCCTTTGGG CACCCCTCTA CTCACCTGGT GCAGGTAGAT GACATGGAGA 24600
CTCATCTCGG CAGAAGCAAG TTCTGGGAGC TGGGCCAGCT TCTGGCCCCC 24650
AGTGCCTCCT GGGGACACAG AGCTGGAACA TAACATGAAG CAGGTCAAAA 24700 A24667G; G24693C
GTCATGCCCT CCTCCCGCCA CACCCCAGAG GACTCCCCTT CTGAATCCCC 24750 | G24717A
CCTCAGCGCC CCAGCTCCCC ACTCCTACAG GATCAGCCCA CCCCCCTCCA 24800
CATGCCCCTG CATCTCAGCC TCCACTCCTC ACCTGGGGTC CTGGGCAATT 24850 C24828G; G24845A
CGGGAAATGG AGGCAAGGAG GCTGGCTGTG GCCGCAGCTG GACAGGGGGC 24900
TGTCGGGCTC AGATCTCTCG GAGGCAGGAG AGGGTGCACG AAGAGGTTGG 24950
CCAGGAAGGC CTCAGGCTGG GTGCAAGAGG AGAGGGAAAG CCAAAGAGGG 25000
AGTCAGAAGA GAGGACAGAA ACGGAGTAGG GAGGAAGCAG AGGCCTAAAG 25050
AAGGCAGGAG AGCAGGCTGG GGGCGGGGGC TGGTGAGGCA GGTTACTACC 25100
TAAGGT
```

ASSESSING BRAIN ANEURYSMS

CROSS-REFERENCE TO RELATED APPLICATIONS

This application is a continuation of U.S. patent application Ser. No. 11/912,540, having a filing date of May 27, 2008; which is a National Stage application under 35 U.S.C. §371 and claims benefit under 35 U.S.C. §119(a) of International Application No. PCT/US2005/014868 having an International Filing Date of Apr. 29, 2005. The disclosures of the prior applications are considered part of (and are incorporated by reference in) the disclosure of this application.

BACKGROUND

1. Technical Field

This document relates to methods and materials involved in assessing brain conditions. For example, this document relates to methods and materials involved in determining whether or not a brain aneurysm will rupture.

2. Background Information

About 10 to 15 million Americans are thought to suffer from a brain aneurysm with about 30,000 of these experiencing a brain aneurysm rupture (subarachnoid hemorrhage; SAH) annually. Unfortunately, about half of the SAH cases result in death or marked disability from the original hemorrhage or a major complication such as rebleeding or vasospasm. When confronting a patient with a brain aneurysm, a clinician recommends either treatment or continued monitoring. Treatment typically involves surgical clipping, endovascular coiling, or a variation thereof.

SUMMARY

This document involves methods and materials related to assessing brain conditions within mammals. For example, this document provides methods and materials that can be used to determine whether or not a mammal (e.g., a human) with a brain aneurysm is likely to experience rupture of the brain aneurysm. The discrepancy between the prevalence of brain aneurysms (as high as 5 percent or 10 to 15 million in the United States population alone) and the incidence of aneurysmal rupture (about 30,000 cases annually in the United States) suggests that some brain aneurysms are more prone to rupture than others (Schievink, *N. Engl. J. Med.,* 336:28-40 (1997) and Inagawa et al., *Surg. Neurol.,* 34:361-365 (1990)). Despite diagnostic and therapeutic advances, it is currently estimated that one-half of those afflicted with aneurysmal rupture will die or be markedly disabled from the original hemorrhage or a major complication such as rebleeding or vasospasm.

Typically, a mammal with a brain aneurysm can be assessed by determining whether or not the mammal contains a polymorphism in an eNOS gene. eNOS (endothelial nitric oxide synthase) polypeptides can be constitutively expressed and can catalyze the conversion of L-arginine into L-citrulline, thereby producing a rapidly diffusing signaling molecule, NO, as the major byproduct. The presence of a polymorphism in an eNOS gene can indicate that the mammal has high likelihood of experiencing brain aneurysm rupture. Determining whether or not a mammal has a high likelihood of experiencing brain aneurysm rupture by assessing the mammal's eNOS genotype as described herein can help clinicians determine the best course of treatment for that mammal. For example, a human brain aneurysm patient who normally might not receive surgical or endovascular treatment may be advised to undergo surgery or endovascular treatment if it is determined that that patient has an allele having at least one polymorphism in an eNOS gene.

In general, this document features a method for assessing a human having a brain aneurysm. The method includes determining whether or not the human contains two or more polymorphisms in SEQ ID NO:1, wherein the presence of the two or more polymorphisms indicates that the brain aneurysm is prone to rupture. The brain aneurysm can be between 2 and 10 mm in diameter. The brain aneurysm can be present in an anterior or posterior communicating artery of the human. The human can be heterozygous for the two or more polymorphisms. The human can be homozygous for the two or more polymorphisms. The method can include determining whether or not the human contains three or more polymorphisms in SEQ ID NO:1. The polymorphisms can be selected from the group consisting of 27 VNTR, T-786C SNP, and G894T SNP.

In another embodiment, this document features a method for determining whether or not to treat a brain aneurysm in a human. The method includes determining whether or not the human contains two or more polymorphisms in SEQ ID NO:1, wherein the presence of the two or more polymorphisms indicates that the brain aneurysm should be treated. The brain aneurysm can be between 2 and 10 mm in diameter. The brain aneurysm can be present in an anterior or posterior communicating artery of the human. The human can be heterozygous for the two or more polymorphisms. The human can be homozygous for the two or more polymorphisms. The method can include determining whether or not the human contains three or more polymorphisms in SEQ ID NO:1. The polymorphisms can be selected from the group consisting of 27 VNTR, T-786C SNP, and G894T SNP. The method can include determining the size of the brain aneurysm. The method can include determining the location of the brain aneurysm.

In another embodiment, this document features a method for determining whether or not to treat a brain aneurysm in a human. The method includes (a) determining whether or not the human contains two or more polymorphisms in SEQ ID NO:1, and (b) determining whether or not the brain aneurysm has a size between 2 and 10 mm in diameter or determining whether or not the brain aneurysm has a location in an anterior or posterior communicating artery of the human, wherein the presence of the two or more polymorphisms in the human and the presence of the size or the location indicates that the brain aneurysm should be treated. The method can include determining whether or not the human is homozygous for the two or more polymorphisms. The human can be heterozygous for the two or more polymorphisms. The human can be homozygous for the two or more polymorphisms. The method can include determining whether or not the human contains three or more polymorphisms in SEQ ID NO:1. The polymorphisms can be selected from the group consisting of 27 VNTR, T-786C SNP, and G894T SNP. The method can include determining whether or not the brain aneurysm has a size between 2 and 10 mm in diameter and determining whether or not the brain aneurysm has a location in an anterior or posterior communicating artery of the human, wherein the presence of the two or more polymorphisms in the human and the presence of the size and the location indicates that the brain aneurysm should be treated.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting. Other features and advantages of the invention will be apparent from the following detailed description, and from the claims.

DESCRIPTION OF DRAWINGS

FIG. 2 is a nucleic acid sequence listing of a human eNOS gene (SEQ ID NO:1).

FIG. 3 is an amino acid sequence listing of a human eNOS polypeptide (SEQ ID NO:2).

FIG. 4 is a listing of the human eNOS gene set forth in FIG. 1 labeling exons, untranslated regions (UTR), and polymorphisms. The nucleic acid sequence is as set forth in SEQ ID NO:1, while the amino acid sequence is as set forth in SEQ ID NO:2.

DETAILED DESCRIPTION

Figure 1:
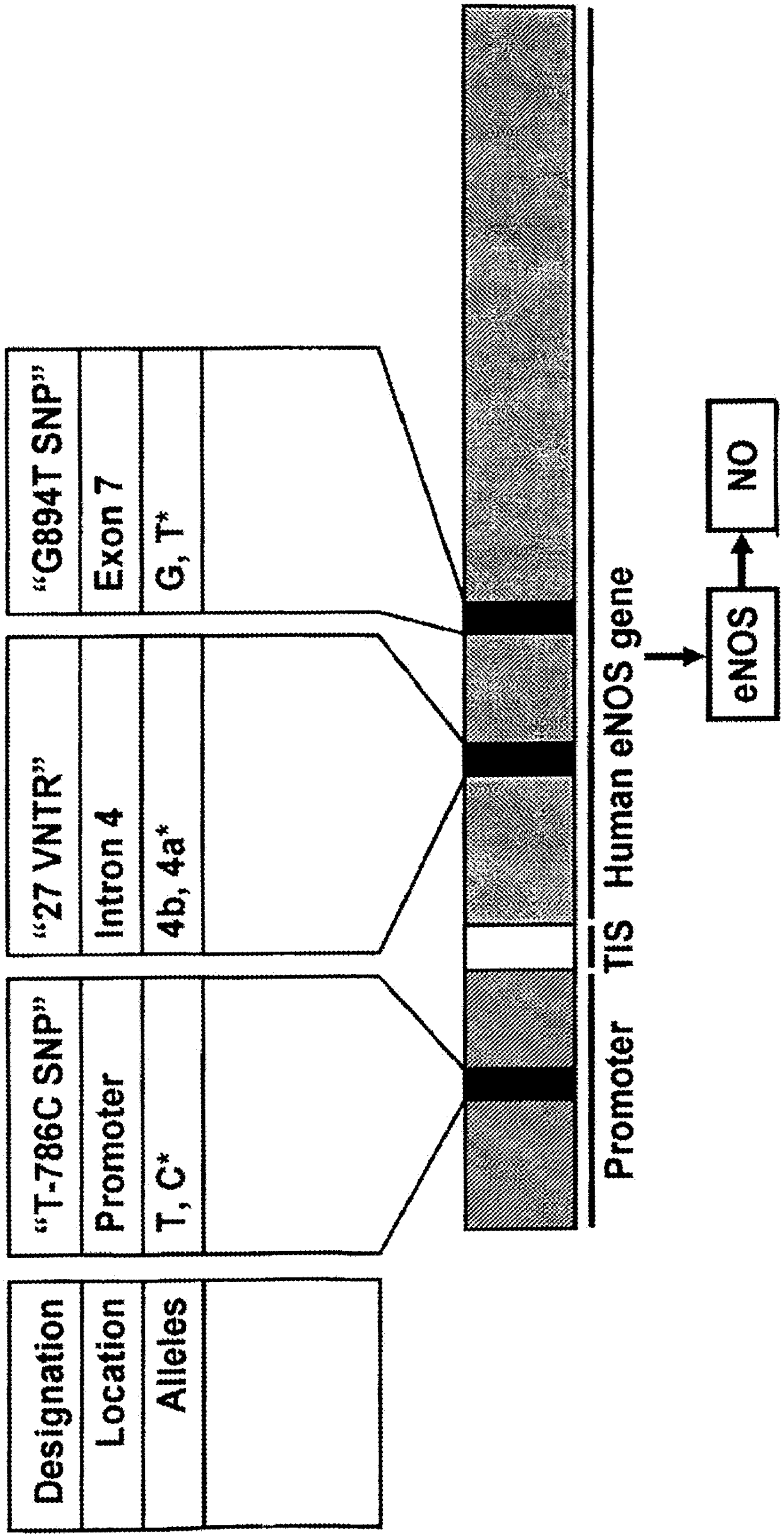
FIG. 1 is a diagram depicting three eNOS gene polymorphisms along with their respective locations in the eNOS gene. For each polymorphism, the putative abnormal allele is indicated by an asterisk. Abbreviations: 4a=four 27-base pair tandem repeats; 4b=five 27-base pair tandem repeats; C=cytosine; G=guanine; kbp=kilobase-pairs; NO=nitric oxide; SNP=single nucleotide polymorphism; T=thymine; TIS=transcription initiation sequence; VNTR=variable number tandem repeat.

This document provides methods and materials related to assessing brain conditions within mammals. For example, this document provides methods and materials that can be used to determine whether or not a mammal (e.g., a human) with a brain aneurysm is likely to experience brain aneurysm rupture. As described herein, a mammal having a polymorphism in an eNOS gene can have a higher likelihood of experiencing brain aneurysm rupture than a mammal not having a polymorphism in an eNOS gene. The term “eNOS gene” as used herein includes the exons that encode an eNOS polypeptide, any introns located between such exons, the promoter region, the sequences up to 3 kilobases (e.g., 0.5, 1, 1.5, 2, 2.5, or 3 kilobases) 5' of the transcriptional start site, and the sequences up to 3 kilobases (e.g., 0.5, 1, 1.5, 2, 2.5, or 3 kilobases) 3' of the stop codon. For example, the sequence set forth in SEQ ID NO:1 (FIG. 2) can be an eNOS gene in the case of a human. See, also, GenBank® Accession No. AF519768.

Any mammal having a brain aneurysm can be assessed to determine whether or not the mammal has a high likelihood of experiencing brain aneurysm rupture. For example, dogs, cats, horses, pigs, cows, sheep, monkeys, and humans can be assessed for the presence or absence of a polymorphism in an eNOS gene. The nucleic acid sequence for a particular mammalian species can be found in GenBank® or can be determined using common molecular biology techniques. In some cases, several eNOS genes can be sequenced from multiple members of the same species to determine a common wild-type sequence to which polymorphic sequences can be compared. In the case of humans, the sequence set forth in SEQ ID NO:1 can be used as a wild-type sequence to which polymorphic sequences are compared. For example, any sequence deviation from the sequence set forth in SEQ ID NO:1 found in a human can be considered a polymorphism. In some cases, the first or consensus nucleic acid sequence deposited in GenBank® for a particular mammalian species can be used as a wild-type sequence to which polymorphic sequences are compared for that species.

A mammal can be assessed to determine whether or not that mammal contains any type of polymorphism in an eNOS gene including, without limitation, insertions, deletions, substitutions, repeats, inverted repeats, and combinations thereof. In some embodiments, a human can be assessed to determine whether or not the human contains the intron-4 27-base pair variable-number-tandem-repeat polymorphism, 27 VNTR; the promoter SNP, T-786C SNP; or the exon-7 SNP, G894T SNP (FIG. 1). Additional examples of polymorphisms that can be used in the case of humans include, without limitation, any of the polymorphisms provided in FIG. 3 or set forth in the Single Nucleotide Polymorphism database of GenBank® with any of the following reference SNP identification numbers: rs3918234; rs1799983; rs3918166; rs3918232; rs3918201; rs3918155; rs1800779; rs3918158; rs3918157; rs2243310; rs3918163; rs2070744; rs3918225; rs10952298; rs3918226; rs3918159; rs3918160; rs2243311; rs3918162; rs3918156; rs3918161; rs1800783; rs2853792; rs3918170; rs3918192; rs1008140; rs1800782; rs3918187; rs7830; rs2853795; rs3918205; rs3730002; rs3918202; rs3918178; rs753482; rs3918193; rs3918204; rs3918237; rs3918164; rs1800781; rs1800780; rs3918177; rs3918231; rs3918194; rs3730305; rs743507; rs3918184; rs3730009; rs867225; rs3918228; rs3918182; rs3918195; rs3918207; rs1007311; rs3918235; rs3918230; rs3918185; rs3918169; rs3730001; rs2853796; rs3834873; rs3918227; rs3918175; rs3918165; rs3793341; rs3918209; rs3918176; rs3918196; rs1541861; rs3730003; rs3918188; rs3793342; rs2566511; rs3918208; rs3918174; rs3918167; rs2256314; rs3918197; rs1065300; rs3918229; rs3918203; rs1808593; rs3918198; rs3918180; rs891511; rs3918236; rs891512; rs3918189; rs3729625; rs3918210; rs3918173; rs3918168; rs743506; rs3918181; rs3918190; rs3918199; rs3918200; rs3918191; rs3918186; rs7792133; rs6947833; rs2566516; rs2566519; rs11371169; rs3730306; rs2566508; rs3730007; rs13305985; rs3918179; rs2853791; rs13420; rs1799984; rs13310854; rs10539416; rs2566506; rs2566517; rs6969597; rs12937; rs2853797; rs2853794; rs2566510; rs10539415; rs13311313; rs13310763; rs2566507; rs10595051; rs2853793; rs3730012; rs2566513; rs11974098; rs3918183; rs13305984; rs2566512; rs13311166; rs13310774; rs3730006; rs1799985; rs7776461; rs2853798; rs2566518; rs13305982; rs3730010; rs2853800; rs2566515; rs2566509; rs10255980; rs4725985; rs3828997; rs933163; rs3134740; rs11771443; or rs10531586.

A mammal can be assessed to determine whether or not that mammal contains a single polymorphism or multiple polymorphisms in an eNOS gene. For example, a mammal can be assessed to determine whether or not that mammal contains one, two, three, four, five, six, seven, eight, nine, ten, or more polymorphisms in an eNOS gene. In some embodiments, a human can be assessed to determine whether or not the human contains any combination of the polymorphisms provided herein such as (1) 27 VNTR, T-786C SNP, and G894T SNP; (2) 27 VNTR and T-786C SNP; (3) 27 VNTR and G894T SNP; (4) T-786C SNP and G894T SNP; (5) 27 VNTR and any of the polymorphisms provided in FIG. 3; (6) T-786C SNP and any of the polymorphisms provided in FIG. 3; or (7) G894T SNP and any of the polymorphisms provided in FIG. 3. The polymorphisms in an eNOS gene can be present on the same allele or on different alleles. For example, a human having two polymorphisms in an eNOS gene such as the 27 VNTR and T-786C SNP can have one allele containing both the 27 VNTR and T-786C SNP, or can have one allele containing the 27 VNTR and the other allele containing the T-786C SNP. In addition, a mammal can be heterozygous or homozygous for a particular polymorphism. For example, one allele can contain the T-786C SNP, or both alleles can contain the T-786C SNP.

Since a mammal having one or more polymorphisms (e.g., one, two, three, four, five, six, seven eight, nine, ten, or more polymorphisms) in an eNOS gene can have a higher likelihood of experiencing brain aneurysm rupture than a mammal not having those polymorphisms in an eNOS gene, the methods and materials provided herein can be used to determine whether or not to treat a brain aneurysm in a mammal. In some cases, the size of a brain aneurysm, the location of a brain aneurysm, or both can be used in addition to assessing the mammal for the presence or absence of polymorphisms in an eNOS gene to determine whether or not to treat the brain aneurysm. Typically, a clinician can recommend treating a brain aneurysm surgically when any one, two, or three of the following are determined: (1) the brain aneurysm's size is between 1 and 35 mm (e.g., between 1 and 20 mm, between 1 and 15 mm, between 2 and 10 mm, between 2 and 8 mm, or between 3 and 6 mm) in diameter, (2) the brain aneurysm's location is in the human's intracranial circulation (e.g., in an anterior or posterior communicating artery), and (3) the mammal contains one or more polymorphisms in an eNOS gene.

Any common diagnostic technique can be used to identify a mammal having a brain aneurysm. For example, diagnostic techniques such as cerebral angiography, magnetic resonance angiography (MRA), or computerized tomographic angiography (CTA) can be used to identify the presence, size, and location of a brain aneurysm within a mammal (e.g., a human). In addition, any method can be used to determine whether or not a mammal contains a polymorphism in an eNOS gene. For example, polymorphisms in an eNOS gene can be detected by sequencing or by performing allele-specific hybridization, allele-specific restriction digests, mutation specific polymerase chain reactions (MSPCR), single-stranded conformational polymorphism (SSCP) detection (Schafer et al., *Nat. Biotechnol.,* 15:33-39 (1995)), denaturing high performance liquid chromatography (DHPLC, Underhill et al., *Genome Res.,* 7:996-1005 (1997)), infrared matrix-assisted laser desorption/ionization (IR-MALDI) mass spectrometry (WO 99/57318), or combinations of such methods.

Genomic DNA or mRNA can be used in the analysis of polymorphisms. Genomic DNA is typically extracted from a biological sample such as blood, but can be extracted from other biological samples including tissue samples. Routine methods can be used to extract genomic DNA from a blood or tissue sample, including, for example, phenol extraction. Alternatively, genomic DNA can be extracted with kits such as the QIAamp® Tissue Kit (Qiagen, Chatsworth, Calif.), Wizard® Genomic DNA purification kit (Promega), and the A.S.A.P.™ Genomic DNA isolation kit (Boehringer Mannheim, Indianapolis, Ind.). In some cases, an amplification step can be performed prior to detecting a polymorphism. For example, nucleic acid from an eNOS gene can be amplified and then directly sequenced. Dye primer sequencing can be used to increase the accuracy of detecting heterozygous samples.

Hybridization also can be used to detect polymorphisms. See, for example, Stoneking et al., *Am. J. Hum. Genet.,* 48:370-382 (1991) and Prince et al., *Genome Res.,* 11:152-162 (2001). In practice, samples of DNA or RNA from one or more individuals can be amplified using pairs of primers, and the resulting amplification products can be immobilized on a substrate (e.g., in discrete regions). Hybridization conditions can be selected such that an oligonucleotide binds to a sequence of interest, e.g., a polymorphic nucleic acid sequence. Such hybridizations typically are performed under high stringency as some polymorphic nucleic acid sequences include only a single nucleotide difference. High stringency conditions can include the use of low ionic strength solutions and high temperatures for washing. For example, nucleic acid molecules can be hybridized at 42° C. in 2×SSC (0.3M NaCl/0.03 M sodium citrate) with 0.1% sodium dodecyl sulfate (SDS) and washed in 0.1×SSC (0.015M NaCl/0.0015 M sodium citrate), 0.1% SDS at 65° C. Hybridization conditions can be adjusted to account for unique features of the nucleic acid molecule, including length and sequence composition. Probes can be labeled (e.g., fluorescently or with biotinylation) to facilitate detection.

For polymorphic nucleic acid sequences that introduce a restriction site, restriction digest(s) with the appropriate restriction enzyme(s) can differentiate wild-type and polymorphic sequences. For polymorphic sequences that do not alter a common restriction site, mutagenic primers can be designed that introduce a restriction site when the polymorphic sequence is present or when a wild-type sequence is present. A portion of an eNOS gene can be amplified using the mutagenic primer and a wild-type primer, followed by digest with the appropriate restriction endonuclease.

Certain polymorphic sequences, such as insertions or deletions of one or more nucleotides, can change the size of a DNA fragment encompassing a polymorphism. The insertion or deletion of nucleotides can be assessed by amplifying the region encompassing the polymorphic sequence and determining the size of the amplified products in comparison with size standards. For example, a region of an eNOS gene that encodes an eNOS polypeptide or regulates expression of an eNOS polypeptide can be amplified using a primer set from either side of a polymorphic sequence. One of the primers is typically labeled, for example, with a fluorescent moiety, to facilitate sizing. The amplified products can be electrophoresed through acrylamide gels with a set of size standards that are labeled with a fluorescent moiety that differs from the primer.

In some embodiments, PCR conditions and primers can be developed that amplify a product only when a particular polymorphic sequence is present or only when the polymorphic sequence is not present (MSPCR or allele-specific PCR). For example, patient DNA and a control can be amplified separately using either a wild-type primer or a primer specific for a polymorphic sequence. Each set of reactions can then be examined for the presence of amplification products using standard methods to visualize the DNA. For example, the reactions can be electrophoresed through an agarose gel, and the DNA visualized by staining with ethidium bromide or other DNA intercalating dye. In nucleic acid samples from heterozygous mammals, reaction products can be detected with each set of primers. Mammalian samples containing solely the wild-type allele would have amplification products only in the reaction using the wild-type primer. Similarly, mammalian samples containing solely the polymorphic allele can have amplification products only in the reaction using the primer containing the polymorphic sequence. Allele-specific PCR also can be performed using allele-specific primers that introduce priming sites for two universal energy-transfer-labeled primers (e.g., one primer labeled with a green dye such as fluoroscein and one primer labeled with a red dye such as sulforhodamine).

Amplification products can be analyzed for green and red fluorescence in a plate reader. See, Myakishev et al., *Genome,* 11(1):163-169 (2001).

Mismatch cleavage methods also can be used to detect differing sequences by PCR amplification, followed by hybridization with a wild-type sequence and cleavage at points of mismatch. Chemical reagents, such as carbodiimide or hydroxylamine and osmium tetroxide can be used to modify mismatched nucleotides to facilitate cleavage.

The invention will be further described in the following examples, which do not limit the scope of the invention described in the claims.

EXAMPLES

Example 1

The Presence of Tandem eNOS Gene Polymorphisms Identifies Brain Aneurysms Prone to Rupture The following experiments were performed to determine whether polymorphisms in eNOS can be used to identify brain aneurysms prone to rupture.

Study Participants

A prospective case-control study involved 107 human subjects each of whom gave informed consent for participation. The control group consisted of 49 people consecutively presenting to the Mayo Clinic with a diagnosis of unruptured intracranial saccular aneurysm. The case group was comprised of 58 people consecutively admitted to the Mayo Clinic diagnosed with aneurysmal subarachnoid hemorrhage (SAH) based on history and radiological findings, including both admission head computerized tomography scan and 4-vessel cerebral angiography.

Genetic Analysis

Three particular eNOS polymorphisms were analyzed (FIG. 1). A single 20 mL sample of peripheral venous blood was obtained from all participants for subsequent DNA extraction and genetic analysis. Genomic DNA was extracted from peripheral blood lymphocytes using QIAamp® DNA Blood Minikit (Qiagen, Germantown, Md.). SNPs were genotyped using Nanochip™ active electronic arrays (Nanogen, San Diego, Calif.) as described elsewhere (Sohni et al., *Clin. Chem.,* 47:1922-1924 (2002)). Oligo 6.61 software was used to design polymerase chain reaction (PCR) primers (IDT, Coralville, Iowa) based on GenBank sequences. PCR mixtures consisted of 25 μL AmpliTaq Gold Master Mix (Applied Biosystems, Foster City, Calif.), 1 μM primers, 20 ng DNA template and water to 50 μL. All oligonucleotides were synthesized by IDT. Primer sequences were 5'-biotin-GCATGCACTCTGGCCTGAAGT-3' (forward; SEQ ID NO:3) and 5'-CAGGAAGCTGCCTTCCAGTGC-3' (reverse; SEQ ID NO:4) for eNOS T-786C SNP, and 5'-biotin-CTGGAGATGAAGGCAGGAGAC-3' (forward; SEQ ID NO:5) and 5'-CTCCATCCCACCCAGTCAATC (reverse; SEQ ID NO:6) for eNOS G894T SNP. Thermal cycling conditions for each were 95° C. for 10 minutes, 30 cycles of 94° C. for 30 seconds, 58° C. for 30 seconds, and 72° C. for 45 seconds, and final extension at 72° C. for 7 minutes. For eNOS T-786C SNP, reporter probes were 5'-Cy3-AGGGT-CAGCCA-3' (SEQ ID NO:7) and 5'-Cy5-GGGTCAGCCG-3' (SEQ ID NO:8) with stabilizer oligonucleotide 5'-GC-CAGGGAAGAGCTTGATGCCCTGGTGGGAGC-3' (SEQ ID NO:9). For eNOS G894T SNP, reporter probes were 5'-Cy3-GTTCTGGGGGC-3' (SEQ ID NO:10) and 5'-Cy5-AGTTCTGGGGGA-3' (SEQ ID NO:11) with stabilizer oligonucleotide 5'-TCATCTGGGGCCTGCAGCAG-CAGGGGCAGCA-3' (SEQ ID NO:12). Known heterozygotes, verified by dye-terminator sequencing performed on ABI 377 DNA sequencers in both forward and reverse directions, were used as controls to normalize hybridization efficiency between dye-labeled reporters. PCR conditions and methods for analyzing the eNOS 27 VNTR polymorphism are detailed elsewhere (Sohni et al., *Clin. Biochem.,* 36:35-39 (2003)). PCR products were analyzed using DNA 500 LabChip® kit on Agilent 2100 Bioanalyzer (Agilent Technologies, Wilmington, Del.) following the manufacturer's instructions. DNA fragment sizes were determined for each sample from the calibration curve in conjunction with markers and sizing ladder. Genotypes were designated based on fragment sizes obtained at the end of the run. For each polymorphism, amplicons were randomly sequenced to determine concordance with microarray genotyping as described herein.

Data Analysis

In order to evaluate the association between the demographic and genetic markers of interest and aneurysmal disease, comparisons were made between cases and controls. Demographics are presented as mean±standard deviation (SD) for continuous variables and percentage of column totals for categorical variables. Univariate associations between demographic variables and disease were assessed using two-sample t-test for continuous variables and Pearson's chi-square or Fisher's exact test (when sample sizes were limited) for categorical variables. Before any statistical analysis of disease-marker associations, allele frequency distribution at each polymorphism locus was tested against Hardy-Weinberg equilibrium (HWE) under Mendelian biallelic expectation using the chi-square test. Univariate associations of allele (which treats each chromosome as a unit) and genotype (which treats a person as a unit) with disease were evaluated using contingency table methods in SAS-v8.2. Allele associations were assessed using Pearson's chi-square or Fisher's exact test (when sample sizes were limited) and genotype associations were assessed using the Cochran-Armitage trend test. The multiple polymorphism marker-disease association with haplotype was evaluated using Haplo.score which accounts for ambiguous linkage phase (Lake et al., *Hum. Hexed.,* 55:56-65 (2002) and Schaid et al., *Am. J. Hum. Genet.,* 70:425-434 (2002)). Haplotype odds ratios (OR) and 95% confidence intervals (CI) were calculated using Haplo.glm. The haplotype comprised of 3 wild-type alleles (4b-T-G) was used as the comparison to calculate the haplotype specific OR and CI. Linkage disequilibrium was assessed using the Graphical Overview of Linkage Disequilibrium (GOLD) software package (Abecasis and Cookson, *Bioinformatics,* 16:182-3 (2002) and Ardlie et al., *Nat. Rev. Genet.,* 3:299-309 (2002)). All tests were two-sided and P-values <0.05 were considered statistically significant.

Clinical Data

When comparing aneurysm cases and controls, there was no significant difference in mean age, gender or race, history of cardiovascular diseases or smoking, or family history of brain aneurysms or SAH (Table 1). Although multiplicity of aneurysms was similar between the two groups, cases presented with significantly smaller aneurysms compared with controls (7.5±4.7 mm vs. 9.6±5.8 mm; P=0.037). The distribution and treatment of aneurysms also differed significantly between the two groups (P<0.001; Table 1).

TABLE 1

Demographic and clinical data for people with unruptured (controls) compared with ruptured (subarachnoid hemorrhage; SAH; cases) brain aneurysms.

| Variable | Controls (n = 49) | Cases (n = 58) | P-value |
|---|---|---|---|
| Age | 57.1 ± 11.5 | 53.2 ± 12.7 | 0.10 |
| Female gender | 36 (73%) | 39 (67%) | 0.48 |
| Caucasian race | 49 (100%) | 58 (100%) | N/A |
| Cardiovascular comorbidities: | | | |
| Diabetes mellitus | 4 (8%) | 4 (7%) | 0.80 |
| Hypertension | 25 (51%) | 24 (41%) | 0.32 |
| Coronary artery disease | 4 (8%) | 7 (12%) | 0.51 |
| Ischemic stroke | 10 (20%) | 5 (9%) | 0.08 |
| History of smoking | 28 (57%) | 41 (71%) | 0.14 |
| Family history of brain aneurysm or SAH | 8 (16%) | 4 (7%) | 0.12 |
| Aneurysm size (mm) | 9.6 + 5.8 | 7.5 + 4.7 | 0.037 |
| Multiple aneurysms | 16 (33%) | 15 (26%) | 0.44 |
| Aneurysm location: | | | <0.001 |
| Anterior communicating artery | 3 (6%) | 16 (28%) | |
| Anterior cerebral artery | 2 (4%) | 5 (9%) | |
| Middle cerebral artery | 17 (35%) | 5 (9%) | |
| Internal carotid artery | 17 (34%) | 7 (12%) | |
| Posterior communicating artery | 1 (2%) | 13 (22%) | |
| Posterior cerebral artery | 1 (2%) | 2 (3%) | |
| Basilar artery | 6 (12%) | 7 (12%) | |
| Vertebral artery | 2 (4%) | 3 (5%) | |
| Aneurysm treatment: | | | <0.001 |
| Clip | 22 (45%) | 24 (41%) | |
| Coil | 10 (20%) | 30 (52%) | |
| Coil then clip | 0 | 1 (2%) | |
| None | 17 (35%) | 3 (5%) | |

Genetic Data

Hardy-Weinberg Equilibrium (HWE): Among controls, the genotype frequencies for eNOS 27 VNTR (P=1.0) and eNOS G894T SNP (P=0.06) were in agreement with those predicted by the HWE. The genotype frequencies for eNOS T-786C SNP (P=0.03) were not in agreement with those predicted by the HWE. Thus, the Cochran-Armitage trend test (which is unaffected by departure from HWE) was implemented and revealed consistent results. For the eNOS T-786C SNP, the departure from HWE was due to a homozygote favoring which was shown to have minimal effect on haplotype estimation (Lake et al., *Hum. Hered.,* 55:56-65 (2002)). Further, to exclude the possibility of genotyping error, thirty-seven T-786C SNP amplicons were randomly sequenced, and the results were found to be fully concordant with microarray genotyping.

Allele and Genotype Frequencies: For each of the three polymorphisms, significant differences in allele and genotype frequency were found between cases and controls with the variant alleles and their corresponding genotypes being present two-to-four times more often among cases (Table 2). Linkage disequilibrium analysis (Ardlie et al., *Nat. Rev. Genet.,* 3:299-309 (2002)) was carried out using both D' and R2 to detect pair-wise linkage disequilibrium among the three polymorphisms. No significant linkage disequilibrium was detected.

TABLE 2

Allele and genotype data for people with unruptured (controls) compared with ruptured (cases) brain aneurysms.

| Locus | Controls (n = 49) N (%) | Cases (n = 58) N (%) | P-value |
|---|---|---|---|
| Allele frequency: | | | |
| eNOS 27 VNTR | | | 0.003 |
| Allele 4a† | 10 (10) | 30 (26) | |
| Allele 4b | 88 (90) | 86 (74) | |
| eNOS T-786C SNP | | | 0.003 |
| Allele C† | 21 (21) | 47 (41) | |
| Allele T | 77 (79) | 69 (59) | |
| eNOS G894T SNP | | | <0.001 |
| Allele T† | 10 (10) | 38 (33) | |
| Allele G | 88 (90) | 78 (67) | |
| Genotype frequency: | | | |
| eNOS 27 VNTR | | | 0.006 |
| 4a/4a | 0 | 1 (2) | |
| 4a/4b | 10 (20) | 28 (48) | |
| 4b/4b | 39 (80) | 29 (50) | |
| eNOS T-786C SNP | | | <0.001 |
| C/C | 5 (10) | 6 (10) | |
| C/T | 11 (22) | 35 (60) | |
| T/T | 33 (67) | 17 (29) | |
| eNOS G894T SNP | | | <0.001 |
| T/T | 2 (4) | 6 (10) | |
| T/G | 6 (12) | 26 (45) | |
| G/G | 41 (84) | 26 (45) | |

†Variant allele

Haplotype Frequencies

A haplotype analysis consisting of 20,000 simulations was implemented to assess the multiple polymorphism marker-disease associations. The observed results were summarized using the simulated P-value, control and case haplotype frequencies, OR, and the 95% CI for each of the eight possible haplotypes (Table 3). Haplotype 4a-C-T, which includes the variant allele for all 3 polymorphisms, was found in 8.4% of cases and 2.3% of controls (simulated P=0.0038), and subjects having this haplotype had an 11.4-fold (1.7-75.9 95% CI) increased odds of being a case. The second identified risk haplotype 4a-C-G, which includes the variant allele for eNOS 27 VNTR and eNOS T-786C SNP, was found in 14.1% of cases and 3.1% of controls (simulated P=0.0196), and subjects having this haplotype had an 8.6-fold (1.8-41.3 95% CI) increased odds of being a case. The third risk haplotype 4b-C-T, which includes the variant allele for eNOS T-786C SNP and eNOS G894T SNP, was found in 13.2% of cases and 2.7% of controls (simulated P=0.0077), and subjects having this haplotype had a 9.3-fold (1.7-49.9 95% CI) increased odds of being a case.

TABLE 3

Haplotype data for people with unruptured (controls) compared with ruptured (cases) brain aneurysms.

| eNOS 27 VNTR | eNOS T-786C SNP | eNOS G894T SNP | Simulated P-value | Control Haplotype Frequency | Case Haplotype Frequency | Odds ratio (95% confidence interval) |
|---|---|---|---|---|---|---|
| 4a | C | T | 0.004 | 0.02 | 0.08 | 11.4 (1.7-75.9) |
| 4a | T | T | NA | 0.01 | <0.001 | NA |
| 4a | C | G | 0.02 | 0.03 | 0.14 | 8.6 (1.8-41.3) |
| 4a | T | G | 0.87 | 0.04 | 0.03 | 2.2 (0.4-13.1) |
| 4b | C | T | 0.008 | 0.03 | 0.13 | 9.3 (1.7-49.9) |
| 4b | T | T | 0.07 | 0.04 | 0.11 | 4.4 (0.9-22.4) |
| 4b | C | G | 0.1 | 0.13 | 0.05 | 0.5 (0.1-1.8) |
| 4b | T | G | <0.001 | 0.70 | 0.45 | 1.0 (NA) |

The results provided herein demonstrate that the presence of two or more variant eNOS alleles in a brain aneurysm patient is associated with an approximately 10-fold increased odds of presenting with aneurysmal rupture. The results also demonstrate that there are two distinct subpopulations of intracranial aneurysms, distinguishable by anatomical and genetic features, with one being more prone to rupture than the other.

The precise molecular effects of eNOS polymorphisms have not been elucidated, although there is biochemical evidence for decreased eNOS gene promoter activation associated with the T-786C SNP variant and reduced eNOS polypeptide expression and enzymatic activity associated both with eNOS 27 VNTR and T-786C polymorphism variants (Nakayama et al., *Circulation,* 99:2864-2870 (1999) and Song et al., *Clin. Chem.,* 49:847-852 (2003)). It is certainly conceivable that such variants may contribute towards aneurysm pathobiology and cerebral vasospasm through increased local oxidative stress leading to vessel wall damage, predilection towards development of atherogenic intimal hyperplasia and systemic hypertension, the presence of aberrant vascular smooth muscle proliferation, and increased platelet aggregation and pro-inflammatory monocyte adhesion, all of which are associated with NO signaling dysfunction. Such mechanisms may also account for the impaired vasorelaxation and heightened vascular wall inflammation characteristic of post-SAH vasospasm.

The results provided herein demonstrate the existence of rupture-prone versus rupture-resistant subpopulations of brain aneurysms. Despite the similarities of demographic and clinical characteristics between the two groups, the genetic differences between the two groups were striking Polymorphic variant alleles and their corresponding genotypes were found to be between two-to-four times more frequent among cases compared with controls, and the haplotype analysis indicated that the presence of two or more (e.g., three) variant alleles was associated with an 8.6 to 11.4 increased odds of being a case (i.e., presenting with a ruptured brain aneurysm). Taken together, the anatomical and genetic data suggest that there are distinct differences between ruptured compared with unruptured aneurysms: the former are smaller, have a greater predilection for the anterior and posterior communicating arteries, and have a tendency to occur more commonly in persons with two or more (e.g., three) variant eNOS polymorphic alleles.

Clinical Implication of these Results

Among the estimated 5-15% of aneurysm-harboring individuals with a relatively strong family history of brain aneurysms or with a heritable connective tissue disorder (such as Ehlers-Danlos, Marfan, or autosomal dominant polycystic kidney disease), noninvasive radiological screening for brain aneurysms is accepted as being worthwhile. For the remaining majority of people at this time referred to as having “sporadic” unruptured brain aneurysms; however, there is currently no adequate screening tool. To identify such individuals via population-wide serial radiological screening seems largely impractical, and there is no “aneurysm gene” yet identified. An important aspect of brain aneurysm management at this time can be how to counsel a patient with a newly diagnosed brain aneurysm (e.g., observation versus treatment). ISUIA has suggested certain aneurysms are more prone to rupture; however, counsel based on ISUIA data alone may not cover the gamut of rupture-prone aneurysms. As described herein, a person diagnosed incidentally or otherwise with an unruptured intracranial aneurysm (especially one located in a higher-risk cerebrovascular territory) and in whom two or more (e.g., three) variant eNOS polymorphic alleles are found, for example, by gene microarray technology, can be counseled towards earlier treatment rather than observation. In addition, a rapid and cost-effective eNOS polymorphism screening tool can be used by clinicians as a genetic aid to predicting rupture risks in patients presenting with unruptured intracranial aneurysms.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for assessing a human having a brain aneurysm, said method comprising:

(a) detecting the presence of two or more polymorphisms in SEQ ID NO:1 in said human, wherein at least two of said two or more polymorphisms are selected from the group consisting of 27 VNTR, T-786C SNP, and G894T SNP, and wherein the presence of said two or more polymorphisms indicates that said brain aneurysm is prone to rupture, and (b) classifying said human as having a brain aneurysm that is prone to rupture.

2. The method of claim 1, wherein said brain aneurysm is between 2 and 10 mm in diameter.

3. The method of claim 1, wherein said brain aneurysm is present in a location selected from the group consisting of an anterior communicating artery, an anterior cerebral artery, a middle cerebral artery, an internal carotid artery, a posterior communicating artery, a posterior cerebral artery, a basilar artery, and a vertebral artery.

4. The method of claim 1, wherein said human is heterozygous for said two or more polymorphisms.

5. The method of claim 1, wherein said human is homozygous for said two or more polymorphisms.

6. The method of claim 1, wherein said method comprises detecting three or more polymorphisms in SEQ ID NO:1 in said human.

7. A method for determining to treat a brain aneurysm in a human, said method comprising:

(a) detecting the presence of two or more polymorphisms in SEQ ID NO:1 in said human, wherein at least two of said two or more polymorphisms are selected from the group consisting of 27 VNTR, T-786C SNP, and G894T SNP, and wherein the presence of said two or more polymorphisms indicates that said brain aneurysm should be treated, and (b) classifying said human as having a brain aneurysm that should be treated.

8. The method of claim 7, wherein said brain aneurysm is between 2 and 10 mm in diameter.

9. The method of claim 7, wherein said brain aneurysm is present in a location selected from the group consisting of an anterior communicating artery, an anterior cerebral artery, a middle cerebral artery, an internal carotid artery, a posterior communicating artery, a posterior cerebral artery, a basilar artery, and a vertebral artery.

10. The method of claim 7, wherein said human is heterozygous for said two or more polymorphisms.

11. The method of claim 7, wherein said human is homozygous for said two or more polymorphisms.

12. The method of claim 7, wherein method comprises detecting three or more polymorphisms in SEQ ID NO:1 in said human.

13. The method of claim 7, wherein said method comprises determining the size of said brain aneurysm.

14. The method of claim 7, wherein said method comprises determining the location of said brain aneurysm.

15. A method for determining to treat a brain aneurysm in a human, said method comprising:

(a) detecting the presence of two or more polymorphisms in SEQ ID NO:1 in said human, wherein at least two of said two or more polymorphisms are selected from the group consisting of 27 VNTR, T-786C SNP, and G894T SNP, (b) determining that the size of said brain aneurysm is between 2 and 10 mm in diameter or determining that the location of said brain aneurysm is in an anterior communicating artery or a posterior communicating artery of said human, wherein the presence of said two or more polymorphisms in said human and the presence of said size or said location indicates that said brain aneurysm should be treated, and (c) classifying said human as having a brain aneurysm that should be treated if said brain aneurysm comprises said size or said location.

16. The method of claim 15, wherein said method comprises determining that said human is homozygous for said two or more polymorphisms.

17. The method of claim 15, wherein said human is heterozygous for said two or more polymorphisms.

18. The method of claim 15, wherein said human is homozygous for said two or more polymorphisms.

19. The method of claim 15, wherein said method comprises detecting the presence of three or more polymorphisms in SEQ ID NO:1 in said human.

20. The method of claim 15, said method comprises determining that the size of said brain aneurysm is between 2 and 10 mm in diameter and comprises determining that the location of said brain aneurysm is in an anterior communicating artery or a posterior communicating artery of said human, wherein the presence of said two or more polymorphisms in said human and the presence of said size and said location indicates that said brain aneurysm should be treated.

* * * * *

SEQUENCE LISTING

```
<160> NUMBER OF SEQ ID NOS: 12

<210> SEQ ID NO 1
<211> LENGTH: 25106
<212> TYPE: DNA
```

-continued

<213> ORGANISM: Homo sapiens
<220> FEATURE:
<221> NAME/KEY: CDS
<222> LOCATION: (1945)..(2102)
<220> FEATURE:
<221> NAME/KEY: CDS
<222> LOCATION: (3344)..(3455)
<220> FEATURE:
<221> NAME/KEY: CDS
<222> LOCATION: (4545)..(4693)
<220> FEATURE:
<221> NAME/KEY: CDS
<222> LOCATION: (4904)..(5066)
<220> FEATURE:
<221> NAME/KEY: CDS
<222> LOCATION: (6498)..(6589)
<220> FEATURE:
<221> NAME/KEY: CDS
<222> LOCATION: (6680)..(6821)
<220> FEATURE:
<221> NAME/KEY: CDS
<222> LOCATION: (7087)..(7226)
<220> FEATURE:
<221> NAME/KEY: CDS
<222> LOCATION: (7331)..(7505)
<220> FEATURE:
<221> NAME/KEY: CDS
<222> LOCATION: (8639)..(8740)
<220> FEATURE:
<221> NAME/KEY: CDS
<222> LOCATION: (9372)..(9566)
<220> FEATURE:
<221> NAME/KEY: CDS
<222> LOCATION: (9685)..(9758)
<220> FEATURE:
<221> NAME/KEY: CDS
<222> LOCATION: (9962)..(10106)
<220> FEATURE:
<221> NAME/KEY: CDS
<222> LOCATION: (10341)..(10445)
<220> FEATURE:
<221> NAME/KEY: CDS
<222> LOCATION: (14569)..(14636)
<220> FEATURE:
<221> NAME/KEY: CDS
<222> LOCATION: (15032)..(15148)
<220> FEATURE:
<221> NAME/KEY: CDS
<222> LOCATION: (15245)..(15419)
<220> FEATURE:
<221> NAME/KEY: CDS
<222> LOCATION: (17074)..(17206)
<220> FEATURE:
<221> NAME/KEY: CDS
<222> LOCATION: (17333)..(17411)
<220> FEATURE:
<221> NAME/KEY: CDS
<222> LOCATION: (17542)..(17729)
<220> FEATURE:
<221> NAME/KEY: CDS
<222> LOCATION: (18259)..(18431)
<220> FEATURE:
<221> NAME/KEY: CDS
<222> LOCATION: (18741)..(18951)
<220> FEATURE:
<221> NAME/KEY: CDS
<222> LOCATION: (19043)..(19130)
<220> FEATURE:
<221> NAME/KEY: CDS
<222> LOCATION: (20496)..(20617)
<220> FEATURE:
<221> NAME/KEY: CDS
<222> LOCATION: (21376)..(21524)
<220> FEATURE:
<221> NAME/KEY: CDS
<222> LOCATION: (21869)..(22063)
<220> FEATURE:
<221> NAME/KEY: CDS
<222> LOCATION: (22153)..(22311)

-continued

<400> SEQUENCE: 1

```
gtggtgggta cctgtaatct cagctactca ggaggctggg tcaggagaat cgcttgaacc     60
caggaggcgg aggttacagt gagctgagat agcaccattg cattccagcc tggacaacaa    120
aagcgagact ctgtctcaaa aaaaaaaaaa aattagccag gcgtggtggt gggtgcctgt    180
cgtcctcggg aggctgaggc atgagaatca ctccgggagg cagaggttgc aatgaaccaa    240
gatcacacca ctgcactcca gcctgggtga cagagcaaga ctctgtctaa aaaaaaaaaa    300
aagacagaag gatgtcagca tctgatgctg cctgtcacct tgaccctgag gatgccagtc    360
acagctccat taactgggac ctaggaaaat gagtcatcct tggtcatgca catttcaaat    420
ggtggcttaa tatggaagcc agacttgggt tctgttgtct cctccagcat ggtagaagat    480
gcctgaaaag taggggctgg atcccatccc ctgcctcact gggaaggcga ggtggtgggg    540
tggggtgggg cctcaggctt ggggtcatgg gacaaagccc aggctgaatg ccgccccttcc   600
atctccctcc tcctgagaca ggggcagcag ggcacactag tgtccaggag cagcttatga    660
ggccccttca ccctccatcc tccaaaactg gcagacccca ccttcttggt gtgaccccag    720
agctctgagc acagcccgtt ccttccgcct gccggccccc cacccaggcc caccccaacc    780
ttatcctcca ctgcttttca gaggagtctg gccaacacaa atcctcttgt ttgtttgtct    840
gtctgtctgc tgctcctagt ctctgcctct cccagtctct cagcttccgt ttctttctta    900
aactttctct cagtctctga ggtctcgaaa tcacgaggct tcgacccctg tggaccagat    960
gcccagctag tggcctttct ccagcccctc agatgacaca gaactacaaa ccccagcatg   1020
cactctggcc tgaagtgcct ggagagtgct ggtgtacccc acctgcattc tgggaactgt   1080
agtttcccta gtcccccatg ctcccaccag ggcatcaagc tcttccctgg ctggctgacc   1140
ctgcctcagc cctagtctct ctgctgacct gcggccccgg gaagcgtgcg tcactgaatg   1200
acagggtggg ggtggaggca ctggaaggca gcttcctgct cttttgtgtc ccccacttga   1260
gtcatggggg tgtgggggtt ccaggaaatt ggggctggga ggggaaggga taccctaatg   1320
tcagactcaa ggacaaaaag tcactacatc cttgctgggc ctctatcccc aagaacccaa   1380
aaggactcaa gggtggggat ccaggagttc ttgtatgtat ggggggaggt gaaggagaga   1440
acctgcatga ccctagaggt ccctgtggtc actgagagtg tgggctgcca tcccctgcta   1500
cagaaacggt gctcaccttc tgcccaaccc tccagggaaa ggcacacagg ggtgaggccg   1560
aaggcccttc cgtctggtgc cacatcacag aaggaccttt atgacccccct ggtggctcta  1620
ccctgccact ccccaatgcc ccagccccca tgctgcagcc ccagggctct gctggacacc   1680
tgggctccca cttatcagcc tcagtcctca cagcggaacc caggcgtccg gccccccacc   1740
cttcaggcca gcgggcgtgg agctgaggct ttagagcctc ccagccgggc ttgttcctgt   1800
cccattgtgt atgggatagg ggcggggcga gggccagcac tggagagccc cctcccactg   1860
ccccctcctc tcggtcccct ccctcttcct aaggaaaagg ccagggctct gctggagcag   1920

gcagcagagt ggacgcacag taac atg ggc aac ttg aag agc gtg gcc cag      1971
                           Met Gly Asn Leu Lys Ser Val Ala Gln
                           1               5

gag cct ggg cca ccc tgc ggc ctg ggg ctg ggg ctg ggc ctt ggg ctg     2019
Glu Pro Gly Pro Pro Cys Gly Leu Gly Leu Gly Leu Gly Leu Gly Leu
10                  15                  20                  25

tgc ggc aag cag ggc cca gcc acc ccg gcc cct gag ccc agc cgg gcc     2067
Cys Gly Lys Gln Gly Pro Ala Thr Pro Ala Pro Glu Pro Ser Arg Ala
                30                  35                  40

cca gca tcc cta ctc cca cca gcg cca gaa cac ag  gtaagggcca          2112
Pro Ala Ser Leu Leu Pro Pro Ala Pro Glu His Ser
```

-continued

```
            45                  50

ggcagctagg agcaggtggg caacaagggt ggtgtcaagg cctgaagcct ggggctggga   2172

aggtctggaa cttgtagctg agtcgggagg gccaggtcac aaatgcaaaa gggctattaa   2232

tgtgcataga acaggacagt ctgggaggct cagaaaggag accaggatca gagtcggcag   2292

gtgaaagctg ggagtaaggg tgccagctat agaatctggc cagggtttga atgctgctct   2352

gccgccagga gctgtttgac tttgagcaag ttacttaatc tctctgaacc tccatttata   2412

taaaacgaga tatggcaata cttactccat ggggaagtaa gtttctagct cacagcaagc   2472

cttcaacagc agcgatgatt atttagctgg agaagaaagg agctgacagc agtggttaca   2532

ggagtgagaa agtggggtct cccagaagag ggagagagtt gggcaggaaa ctcgggccct   2592

tggggtaagc aggctgagaa gacagagcca ccaggctttt ttcccctgct ccagcccccct  2652

ctcctcgtgg ctgtcacccg aaaactggac catgcagttc ccacaagagt cctcccgggg   2712

gtagaggtcc caggagggag gaaagacccg gaggcctggt ggggtgccag gccgggggca   2772

ggctggggct gcaggcagct atgcagggaa ggctgagggc cggggccctg ctgctcaggc   2832

gcacccttgg cctgagtccc tcccttcctc cctgccgctg gtggctctgg gaggaagtga   2892

taaggcctgc gaggcttccc ttcacacatg gggctgctgt caggaggggt tgtgagtgcg   2952

gagggaaatc agagctgagg aatccctgca gggcttccct ccactcaagc accaggctct   3012

gtccccctca gggtagggct tatagcagct ttgcgggggg tggacacccc atctccagaa   3072

gaggtgaggt gggcgctgca ggtgggatgc gaacttagcc tcgggtcagg ggctcaggag   3132

ctcagcacca gcagcccctg cagcccagga ccctggtcta taaacggagg cacagctcgc   3192

ctctagctcc taaggcatgg ggaacgccag aaggcatgcg gcaggtgggc tgtgagatcg   3252

ccagtgctgt aacaggggcc tccgggtgac atctgggaag gctgaaagga aacaaaccct   3312

tcctgatgac cctatccctg gctcccaaca g c ccc ccg agc tcc ccg cta acc    3365
                                     Pro Pro Ser Ser Pro Leu Thr
                                         55                  60

cag ccc cca gag ggg ccc aag ttc cct cgt gtg aag aac tgg gag gtg     3413
Gln Pro Pro Glu Gly Pro Lys Phe Pro Arg Val Lys Asn Trp Glu Val
                65                  70                  75

ggg agc atc acc tat gac acc ctc agc gcc cag gcg cag cag             3455
Gly Ser Ile Thr Tyr Asp Thr Leu Ser Ala Gln Ala Gln Gln
            80                  85                  90

gtaaggccgg catgccctgt ccccatcgtc tccagggaaa gggtgggtaa ggcctggcct   3515

cagatggggc cggagaggga agctcaaccc ttctttgaat tggtcccttg tttccaaaaa   3575

gaggagagga ctgggaagaa ccagaggagt tgagggacat gcacgggact tgggtgaccc   3635

tcagcctcca gccttacccc caaccctggc tcaaactctc cccccatccca cccctgcacc  3695

cctttccccc ctcccacccc tgcacccttc ctccctctcc ccccgtcccc tgcctgcatt   3755

cctcctccct ctccccatct caccccctgca cccctcttcc ctctcccacc cctgcacccc  3815

tcctccctct ccccgtccca ccctgcactc ccgccctctc cagcgtccca cccctacacc   3875

cctcctccct ctgccccatt ccacccctgc accccctcct ccctctgccc cgacccaccc   3935

ctgcacccct cctccctctc ccccgtccca cccctgcatc cctcctccct ctgccccgtc   3995

ccacccctac acccctcctc cctctccccc atcccacccc taaacccctc ctccctctcc   4055

cctgtcccat ccctgcaccc ttcctccctc tccccgtccc atccctgcac ccttcctccc   4115

tctccccgtc ccatccctgc acccctcctc cctctgctcc catcccaccc ctgcacccct   4175

cctccctctg cccctacccc acctctgcac ccctcctcct tctccccatc ccacccctgc   4235
```

-continued

```
acccctcctc cctctgcccc taccccaccc ctgcacccct cctccttctc cccatcccac   4295

ctctgcaccc ctcctccctc tcccctctcc caccccctgta cccttcctcc ttctccccgt   4355

cccacccctg cacttctcct ccctctcacc catcccaccc ctgcaccctt cttccctctc   4415

ccccatccca ccactgcacc cctcctccct ctccccctgt tccacccctg cacccctcct   4475

ccctgccccc aactcccatc ccacccctgc accctggcct gtcctgacct ttgcactccc   4535

tcgacccag gat ggg ccc tgc acc cca aga cgc tgc ctg ggc tcc ctg gta   4586
          Asp Gly Pro Cys Thr Pro Arg Arg Cys Leu Gly Ser Leu Val
                      95                  100

ttt cca cgg aaa cta cag ggc cgg ccc tcc ccc ggc ccc ccg gcc cct     4634
Phe Pro Arg Lys Leu Gln Gly Arg Pro Ser Pro Gly Pro Pro Ala Pro
105                 110                 115                 120

gag cag ctg ctg agt cag gcc cgg gac ttc atc aac cag tac tac agc     4682
Glu Gln Leu Leu Ser Gln Ala Arg Asp Phe Ile Asn Gln Tyr Tyr Ser
                125                 130                 135

tcc att aag ag  gtgacagctt cccggacgcc acagcctccc ttgtcccact         4733
Ser Ile Lys Arg
            140

gaggccccag aaaccccgtg acgaccttcc catgaccccc tcccttccca gatcctaaca   4793

ccacgtgggc ccctcccgcc ctcccccagc acttgcacaa agcctggagg agggcctccc   4853

tgtcccacac aacttcctgc ttgtcccctt cccacccctc tcctccccag g agc ggc    4910
                                                         Ser Gly

tcc cag gcc cac gaa cag cgg ctt caa gag gtg gaa gcc gag gtg gca     4958
Ser Gln Ala His Glu Gln Arg Leu Gln Glu Val Glu Ala Glu Val Ala
        145                 150                 155

gcc aca ggc acc tac cag ctt agg gag agc gag ctg gtg ttc ggg gct     5006
Ala Thr Gly Thr Tyr Gln Leu Arg Glu Ser Glu Leu Val Phe Gly Ala
    160                 165                 170

aag cag gcc tgg cgc aac gct ccc cgc tgc gtg ggc cgg atc cag tgg     5054
Lys Gln Ala Trp Arg Asn Ala Pro Arg Cys Val Gly Arg Ile Gln Trp
175                 180                 185                 190

ggg aag ctg cag gtgcggctgg ccagcgactg agagacccgg gcgctaccaa         5106
Gly Lys Leu Gln

aaggggagcg gggtggcggg gcagttccta aggcttcccg ggggctggga ggtcccaaac   5166

tgtgggggag atccttgcct tttcccttag agactggaaa ggtaggggga ctgccccacc   5226

ctcagcaccc aggggaacct cagcccagta gtgaagacct ggttatcagg ccctatggta   5286

gtgccttggc tggaggaggg gaaagaagtc tagacctgct gcaggggtga ggaagtctag   5346

acctgctgca ggggtgagga agtctagacc tgctgcaggg gtgaggaagt ctagacctgc   5406

tgcgggggtg aggaagtcta gacctgctgc gggggtgagg acagctgagc ggagcttccc   5466

tgggcggtgc tgtcagtagc aggagcagcc tcctggaaaa gccctggctg ctgcttctcc   5526

cccaagagag aaggcttctc ccgccaggcc agtccagtgc agcccctcac ccacacccac   5586

tgctacccca gttcccctgc ttcggcccgc accctccctc acaccccagc ccacagactc   5646

ggggctggcc ttagttactg gaacgcctgt gaccacagca ctaagagaag caagctgccc   5706

catgggggac ttggtcccat ggccttggcc tccttcacca tcactggccg ccaaagagtt   5766

tgaaataaag ccacgtgccc agtgaatccc aaaggaacct caactaaaat aaaaacaatc   5826

ctatctgaca cttgcctgac cctctaagtc attcaaagct ttagctcaac ttcgatccat   5886

ctgagctgcc atagtggacc ccactcagag ctgcgtccct cccttgaccc caggttggtc   5946

cctgccactc ccctgcccct gtcactgaca catgtttcct cctccctcag gcaggagtgg   6006

gacctcccag cctcctcctg ggcctccac tcagaatgtc aggatgagca gggtcctagg   6066
```

-continued

```
aggcctctgg tgcagccttc ccttcccacc atccatgtgc tcaaagagaa tcacccgtcc   6126

tttcttgaat gccatggatc atgggggatt tgctgcccac actcctaggc ggcctcttag   6186

acatccgttg gtgcctaacc caagcatcag tttggcagag gccgagtccc tcctctgtac   6246

tggataccaa gtcagcttcc atagggatgg ggagacacct ggcccaggga ggagatgaga   6306

agcagcccgg atggtgctac atatgtcaga gagcagggca ggaagggatc agtgtggctg   6366

ccaatggtca ggagggcgcc atggagtgaa ccatggcccc tgcctcctca ccagcagctc   6426

ctctggagct gatactcaag acccccgtc tctctcctca ccctcctctc ccgctgcctc   6486

ggctggctca g gtg ttc gat gcc cgg gac tgc agg tct gca cag gaa atg    6536
             Val Phe Asp Ala Arg Asp Cys Arg Ser Ala Gln Glu Met
             195                 200                 205

ttc acc tac atc tgc aac cac atc aag tat gcc acc aac cgg ggc aac     6584
Phe Thr Tyr Ile Cys Asn His Ile Lys Tyr Ala Thr Asn Arg Gly Asn
        210                 215                 220

ctt cg  gtgagtgccc cccaccatgc caggccccag ccttcttccc caaggcaggg      6639
Leu Arg
    225

aaggcggggc tctgaccagc tctttcccca tgcgtgccag c tcg gcc atc aca gtg   6695
                                              Ser Ala Ile Thr Val
                                                              230

ttc ccg cag cgc tgc cct ggc cga gga gac ttc cga atc tgg aac agc     6743
Phe Pro Gln Arg Cys Pro Gly Arg Gly Asp Phe Arg Ile Trp Asn Ser
                235                 240                 245

cag ctg gtg cgc tac gcg ggc tac cgg cag cag gac ggc tct gtg cgg     6791
Gln Leu Val Arg Tyr Ala Gly Tyr Arg Gln Gln Asp Gly Ser Val Arg
            250                 255                 260

ggg gac cca gcc aac gtg gag atc acc gag gtgggcaccg agggccaccc       6841
Gly Asp Pro Ala Asn Val Glu Ile Thr Glu
        265                 270

atgagggtgt ccccaaggtg gagaatgagg aaaccagtgg gagaaggctc gggggatcca   6901

ggcaggaaga ggggagcctc ggtgagataa aggatgaaaa acaccaaagg aggggtgcct   6961

gggtggtcac ggagacccag ccaatgaggg accctggaga tgaaggcagg agacagtgga   7021

tggaggggtc cctgaggagg gcatgaggct cagccccaga accccctctg gcccactccc   7081

cacag ctc tgc att cag cac ggc tgg acc cca gga aac ggt cgc ttc gac   7131
      Leu Cys Ile Gln His Gly Trp Thr Pro Gly Asn Gly Arg Phe Asp
              275                 280                 285

gtg ctg ccc ctg ctg ctg cag gcc cca gat gag ccc cca gaa ctc ttc     7179
Val Leu Pro Leu Leu Leu Gln Ala Pro Asp Glu Pro Pro Glu Leu Phe
        290                 295                 300

ctt ctg ccc ccc gag ctg gtc ctt gag gtg ccc ctg gag cac ccc ac      7226
Leu Leu Pro Pro Glu Leu Val Leu Glu Val Pro Leu Glu His Pro Thr
    305                 310                 315

gtgagcacca aagggattga ctgggtggga tggagggggc catccctgag cctctcaaga   7286

agggcctgca aggggtgct gatcccacac cccaacaccc ccag g ctg gag tgg       7340
                                                  Leu Glu Trp
                                                  320

ttt gca gcc ctg ggc ctg cgc tgg tac gcc ctc ccg gca gtg tcc aac     7388
Phe Ala Ala Leu Gly Leu Arg Trp Tyr Ala Leu Pro Ala Val Ser Asn
        325                 330                 335

atg ctg ctg gaa att ggg ggc ctg gag ttc ccc gca gcc ccc ttc agt     7436
Met Leu Leu Glu Ile Gly Gly Leu Glu Phe Pro Ala Ala Pro Phe Ser
    340                 345                 350

ggc tgg tac atg agc act gag atc ggc acg agg aac ctg tgt gac cct     7484
Gly Trp Tyr Met Ser Thr Glu Ile Gly Thr Arg Asn Leu Cys Asp Pro
355                 360                 365                 370
```

-continued

```
cac cgc tac aac atc ctg gag gtgaggtgcg ggatggggct cgggcaccga        7535
His Arg Tyr Asn Ile Leu Glu
                375

atgcacctgt ccaaggcagg agtctggctc tcactccatc cccaaaatgc cagccacggg   7595

gacaatcaga gcaggtccag ggttgcctcc taaatgggaa ctgaggacaa gctctagaac   7655

cactgaagca aaggggtagg gggtggcagg ggtgtgtgtg ggggtgtgag tgggtgagtg   7715

tgagagtgtg ggtttctggg gtgtgcagtg ggtgagagtg tgggcttgtg gggtgtgtag   7775

tgggtgtgag actgtgggtt tgtaggggtg ggtgagtgtg ggtgtgtggg ggtaggtggg   7835

tgtgggtttg tgggtgtgta taggcagtga ctgtgagact gtgggtttgt gggggtaggt   7895

gactgtgggt ttgtggggtg tgtaggggtg agtgtgtgtg ggtttgtagg ggtaggcgag   7955

tgtgggtttg tggggtgtgt aggggtgagt gtgtgtgagt ttgtaggggt aggcgagtgt   8015

gggtttgtgg ggtgtgtagg ggtgagtgtg tgtgagtttg taggggtagg tgagtgtggg   8075

tttgtggggt gtgtaggggg tgtgtgtggg cttgtagggg taggcgagtg tgggtttgtg   8135

gggtgtgtag gggcgagtgt gagagtgtag gtatgtgggt gtgagtgtgg atgtgtgtag   8195

gcggtgagtg tgaaattgtg ggtttgtggg ggtgggtggg tgtgagtgtg tgggtttgtg   8255

ggtgggtgtg ggtgtgagtg ggtgggtgag gggggcatgg ggatgggtgt gaacatgtag   8315

ttgttctttc aggcatagga cccatagctc tagagctttc atcagattct caaaggggac   8375

cttgactcgg aaaaggttaa gacccatttt agagatgaga aattaaagcc tggagctgag   8435

gagcgactgg cccaaagtcc ctctctgctc tgaggtgcct tcgcaggcaa aaacctgaac   8495

cagcccccta ggcagccagg cctcccaatg gacaccactc acctcactcc ttccagccat   8555

gtacgggaaa cagagatagt ctccccaccc cacccccgtg atcacctctg tccctaccga   8615

tgccacacac ccttctgccc cag gat gtg gct gtc tgc atg gac ctg gat acc   8668
                          Asp Val Ala Val Cys Met Asp Leu Asp Thr
                                      380                 385

cgg acc acc tcg tcc ctg tgg aaa gac aag gca gca gtg gaa atc aac     8716
Arg Thr Thr Ser Ser Leu Trp Lys Asp Lys Ala Ala Val Glu Ile Asn
        390                 395                 400

gtg gcc gtg ctg cac agt tac cag gtgcagaggc ccagactggc caggaaggca    8770
Val Ala Val Leu His Ser Tyr Gln
    405                 410

aagggtttgc atacgggggc agcaggggcg ggggatggag gagaggcagc catttagaaa   8830

ctagggcagg atttggacag gcagaagaag ttccgtagtc ccagtgccat ggcgcacact   8890

ggcctgcggt tcggggacag ggcaggtact attccaggcg ctgtcatctg gtggcttact   8950

gtgtgccagg gaccttgctg tttactgcat gcccagtcat gctgattctc agggcatatt   9010

gggtattgca gtttgtggga cccgctggat cctggaaaca aataccagga tcaagggcac   9070

accaggagtc gtagtttgag gaagccgggg cctgctgaga atttctgtgg gctatttggt   9130

ttggggacca ggcatgcaga tgctggagat tagagctgct tgttgcatgt tgaacctgca   9190

gcatgaccat gcatgatgtg gtttggggtg agggtgacat tgtggtttga ggggacacag   9250

ggtgtgttag atatggggta atcgagggca catgtggttt ggggtgaccg gagtggtgga   9310

ggaagaatgg gcgaggtctg tgggtctggt ttgagcctct ccccctctct ctcccttcca   9370

g cta gcc aaa gtc acc atc gtg gac cac cac gcc gcc acg gcc tct ttc   9419
  Leu Ala Lys Val Thr Ile Val Asp His His Ala Ala Thr Ala Ser Phe
              415                 420                 425

atg aag cac ctg gag aat gag cag aag gcc agg ggg ggc tgc cct gca     9467
Met Lys His Leu Glu Asn Glu Gln Lys Ala Arg Gly Gly Cys Pro Ala
        430                 435                 440
```

-continued

```
gac tgg gcc tgg atc gtg ccc ccc atc tcg ggc agc ctc act cct gtt     9515
Asp Trp Ala Trp Ile Val Pro Pro Ile Ser Gly Ser Leu Thr Pro Val
    445                 450                 455

ttc cat cag gag atg gtc aac tat ttc ctg tcc ccg gcc ttc cgc tac     9563
Phe His Gln Glu Met Val Asn Tyr Phe Leu Ser Pro Ala Phe Arg Tyr
460                 465                 470                 475

cag gtgcccaccc taactggctc tgccagcctg ggcccagctc taattctaag          9616
Gln

cagcccctgg ggacctctaa cctttccttt tctttacctc ccctcccaac cccatcatct   9676

ctctgcag cca gac ccc tgg aag ggg agt gcc gcc aag ggc acc ggc atc    9726
         Pro Asp Pro Trp Lys Gly Ser Ala Ala Lys Gly Thr Gly Ile
                     480                 485                 490

acc agg aag aag acc ttt aaa gaa gtg gcc aa  gtgggtcccc tgggagcccc   9778
Thr Arg Lys Lys Thr Phe Lys Glu Val Ala Asn
                495                 500

gctctcccac acacaccctg ggggccccac tctcccccac acaccctggg ggaccctgcc   9838

ccagcagtgt tctgggccta ccactcagta tcccaaaacc ctgttgtgag ggggttggac   9898

ccttgcctgg ggaggccctg cctctgtgca cccgggacac cctcacacct tcctctcccg   9958

cag c gcc gtg aag atc tcc gcc tcg ctc atg ggc acg gtg atg gcg aag  10007
      Ala Val Lys Ile Ser Ala Ser Leu Met Gly Thr Val Met Ala Lys
                  505                 510                 515

cga gtg aag gcg aca atc ctg tat ggc tcc gag acc ggc cgg gcc cag    10055
Arg Val Lys Ala Thr Ile Leu Tyr Gly Ser Glu Thr Gly Arg Ala Gln
            520                 525                 530

agc tac gca cag cag ctg ggg aga ctc ttc cgg aag gct ttt gat ccc    10103
Ser Tyr Ala Gln Gln Leu Gly Arg Leu Phe Arg Lys Ala Phe Asp Pro
        535                 540                 545

cgg gtagggctga gcccagggga gcagggagct agaaagaggg ggctctatca         10156
Arg

gcatcttcag ggtgccctg gaggacagga agtgttacaa gtcaggactc atgaggaacc   10216

cggaaccaca ggtgttcaga gatcaagttg gggcctgaat cttgcactgc cagggaggcc  10276

agagtgagga gggcagggcc tccgggggcc acagcaccca ggacatctgt cttcccaccc  10336

acag gtc ctg tgt atg gat gag tat gac gtg gtg tcc ctc gaa cac gag   10385
     Val Leu Cys Met Asp Glu Tyr Asp Val Val Ser Leu Glu His Glu
     550                 555                 560

acg ctg gtg ctg gtg gta acc agc aca ttt ggg aat ggg gat ccc ccg    10433
Thr Leu Val Leu Val Val Thr Ser Thr Phe Gly Asn Gly Asp Pro Pro
565                 570                 575                 580

gag aat gga gag gtgagaactt ccaggaaagg ggctgctggg aatgaggaga        10485
Glu Asn Gly Glu

gactcagaat tggagtgact gggcaggaac ctctgcccaa cacacacaca cacacacaca  10545

cacacacaca cacacacaca cacacacaca cacacacaca cacacacacg ccaggatgga  10605

aagggagatg ctaagagacc cctggagcct gaaaccccac acaagctacg ctcccagccc  10665

acccatgtgg ctgcctccct gcaagcacat ttgcttaact gcgcgtcccc aagtcatttc  10725

cattatcagt gcaagttttt aatacaagga aggcacatcc tggctgacca agaggttaga  10785

ctgtgctcgg gcactgacaa gaaaaacagg gatacgtcac tgagggcggc ttctaggatg  10845

cgggtaatgt ttcttaatgg gatactggtt acacaggtgt gttcagtttg taaaaatcca  10905

cagagctgta catttacaac atgtacaaca ctattccagc attttatttt atttgtttta  10965

tttattttga gaacctattt acgttgccca ggctggcctt gaactcctag cctcaagaga  11025

tcctcctgcc gcaggctcct ttttcaaaag aagaaattga gcgctgttta gatgccaaca  11085

tagattaaat aacttcactt tttaaaaaga aacacaaagc tagagtacca tcattgaatt  11145
```

-continued

```
ccttctcttg caagcttagg tatctctgag gtgccccagg ctaggctcat ttctgagtct  11205
tacctgctcc agcttctagg tgttaaaggc cttattagca ctaagtactt cctcagtact  11265
ctttttcttt ttttcctttg agacagggtc tcactttgtg gcccaggctg gagtgcagta  11325
gtacaatcac ggctcactgc agcctcaacc tcctagactc aagcaatcct cccacttcaa  11385
cctcccaagt agttgggact acaggcgcat gccatgatgc ctagctaatt tttgtatttt  11445
ttatagagat ggggtttcgc catgttgccc aggctggtct ctaactcctg ggttcaagca  11505
atccacctgc ctcggcctcc caaagtgctg cgattataga cgtgagccac tgcacctggc  11565
cctcagtatc ttaagcaagt tggaatctcg tgaaaccctt tttgctgcct tagtgtccgt  11625
ttcagccctc attctgacct accttttcaa gaaaaatagc accagcaatt gacttttttt  11685
tagcataaag gtgtatagac acccatataa cctacagcct tcacaaggca tagcacattt  11745
tcaccaccct ggaaagttcc ctcatcagtt cctcacgtga atcccttccc agtctgtctc  11805
cctgccagaa gtgtctgtca ccacagaata gtttcgcctg ctctagaacg gcacctagat  11865
ggaagcacgc agtgttgcgg cgtctcctgc tgaggctgtt tttgaggcgc actcgtgttg  11925
ctgcgtgact cagtatttca ctcattctgc tgctgagtgc cgttcattgt gtgaatatcc  11985
ccagtttgtt tacccattct cttgttggtg acacttgggc tgtttccagg tcggggctat  12045
tatgaataaa cctgttatga acattcttgt acccggcttt tgtgggctta tgtttttatt  12105
tctcttgggt aaatacctag gagtagaatt ggtaggtcat agggtagatg catgtttaat  12165
ctttcacttt tttaaaaaat aaaactgcca ggccaggcgc ggtggctcac gcctgtgatc  12225
ccagcacttt gggaggccca ggtgggtgga tcacttgagg tcagaagctc aagaccagcc  12285
tggccaacat ggcaaaaccc tgtctctact aaaaatacaa aaattagctg ggcatggtgg  12345
cgcacgccta tagtcctagc tactcaggag gctaggcggg agaattgctt gaacctggga  12405
ggtggaggtt gcagtgagcc gagatcacgc cactgcactc cagcctgggt gacagagcaa  12465
gaattctact taaaataaaa tacaaataaa taaaataaaa ctgtcaaaca gcaaagcaaa  12525
ttaaactgcc ctttaacatc tgtgcagttc aatgtatgtt aattttatcc caaattttta  12585
acaaatctag gaatacagct cacagaaaat ggggtatatt cactaaaaat aaggaatatt  12645
tatagcaaat ttgtttgtaa taccccacac tggaaacaat tcaaatgacc atcgacaaat  12705
actgataaat tgtggtatat tcaagtgcca tatcgcacta agtgtgaacg aaacacaacc  12765
acacacaaca gtgcaggtga atctcaaaaa atgtgaagag aagaaaaagc cagaccaaag  12825
aatacatact gtactacagg gttcacttta tataaagttc agaaacaggc agaactaatc  12885
cacggagtta gaaattagga gaggagttag tcactgggat gggggtggca gtgacaggaa  12945
gaaggcacga agttggcttc taggatgcgg gtaatgtttg tttgtttgtt tgtttgtttg  13005
tttttgtttt tgagctggag tctcactctg ttgcccaggc tggagtgcaa tggcgtgatc  13065
tcggctcact gcaacctccg cctccccggt tcaagcgatt ctcctgcctc agcctcccga  13125
gtagctggga ttacaggtgc ccgccaccat ggccagctaa tttttgtgtt tttagtagag  13185
acgcggtttc accatgttgg ccaggctggt cttgaatccc tgacctcagc ctcccaaagt  13245
gctgggatta caggcgtgag ccaccacgcc cagccacggg taatgtttct cgatgggatg  13305
ctggttgcac aggtgtgttc agtttgtgaa aacttacaga gttgtacatt tacaacatgt  13365
gtgcacctct ggacttgtgt tgcacgttga caaaacattc aaaaatgaaa ttcaaatcgt  13425
tcttgctaac tctggcgcac ttgggaacca gcacccagag gcatctgcag ttgagcacca  13485
gatgcagttc cttccagctt ccttccccct gggaggtccg cttgatgcca cttcttcatg  13545
```

-continued

```
gcagcacaaa caaggccatg gtcttctgag gagggcaacc tgcacaatgt ctgctagtga  13605

ccaggacact gctgaaggaa ctgagagttt gtccacccat gaaatccact aaaacaggaa  13665

agattttgct ctagccgttg ttagccagga gtgaggaaag agctgtgccc tcccctgcag  13725

ctgcgaggac gatctgcctg ccccaacaag tggggattca gcaactccac ttctaaggat  13785

tacccagctg aagcatttaa aagtgggagc aaggcacacg tacaagggcg tttgagagag  13845

cacctgttcc cagaccaccg agctgccctt cagtctcagt gaagtacaat gtagccacta  13905

aaaagactga ggtcatgttt tggaaagtcc aggccggagg atcgcttgag cccaggagtt  13965

caaggccaga ctgaacaaca cagcgagact ccatctcttc agaaaattta aaaattaacc  14025

aagagtggtg gcacgcacct atagatctag ctactaggaa ggcagaaaaa tcccttaagc  14085

ccaggagtct gaggttacag tgaatgatga tggagccact gcaccccaac ctgggcgaca  14145

gagcaagacc catatctaaa aacaatacta ctacttacgt caatattgtt gtattgacct  14205

ggagggatgt ctgcaataaa ttattgatta aaaccaagga agtacagtat ggtaccactt  14265

ttacttaaaa aaaaaactat aaatatgcac atgcacgtaa gttcaaggaa aaagggctgg  14325

aaggttaaca cctgtcaatg gcgcatatgc ccggagggaa gatggggtgg tctttgtctt  14385

atcactttac acatttctgt aatgtcattt ttcaaaaaca tcagatcgct tttgaaattt  14445

tcaaaacaaa taaaaattaa gttacaaatc aataataatg aggatcagct ggtacagttt  14505

taaacttcta tgtagtttga aatgaaacaa aactaaccct gatgcaaaca ctcccctcgc  14565

cag agc ttt gca gct gcc ctg atg gag atg tcc ggc ccc tac aac agc    14613
    Ser Phe Ala Ala Ala Leu Met Glu Met Ser Gly Pro Tyr Asn Ser
    585                 590                 595

tcc cct cgg ccg gaa cag cac aa  gtgagttggg tgagagtttg ggggagctgg   14666
Ser Pro Arg Pro Glu Gln His Lys
600                 605

gggagctgat gcatttggag acacaaacag aaagggggtc tgaaaagctc tccctctgtg  14726

cctcaagtcg ttttcccacc aaaagccagg gctccaggat gccctccatt ccaggctgca  14786

atggcagtcc tagacctgcc tgcttctgag agccgggaca gtcctgaggt cttcagagat  14846

gggggtgtgg tgtgtcaggg ccccaggctc ggaaccccag ggatgctggc cctcagcccc  14906

tcccaagggc agggcctttc ctgtcccaga ggcagagacc ctgaagccgt ccctggggct  14966

ggggctgggc ctagcctgta tccccagggc cctgtgacaa ccttgtcttt gtcctctctt  15026

gccag g agt tat aag atc cgc ttc aac agc atc tcc tgc tca gac cca    15074
        Ser Tyr Lys Ile Arg Phe Asn Ser Ile Ser Cys Ser Asp Pro
                610                 615                 620

ctg gtg tcc tct tgg cgg cgg aag agg aag gag tcc agt aac aca gac    15122
Leu Val Ser Ser Trp Arg Arg Lys Arg Lys Glu Ser Ser Asn Thr Asp
            625                 630                 635

agt gca ggg gcc ctg ggc acc ctc ag  gtcagggcct caccaagagg          15168
Ser Ala Gly Ala Leu Gly Thr Leu Arg
        640                 645

ggtgcaacgg gtgggcaagc tgcctgggca aacgtggcct gcaaagggag ctccactgac  15228

gacccctgca ccccag g ttc tgt gtg ttc ggg ctc ggc tcc cgg gca tac    15278
                    Phe Cys Val Phe Gly Leu Gly Ser Arg Ala Tyr
                                650                 655

ccc cac ttc tgc gcc ttt gct cgt gcc gtg gac aca cgg ctg gag gaa    15326
Pro His Phe Cys Ala Phe Ala Arg Ala Val Asp Thr Arg Leu Glu Glu
        660                 665                 670

ctg ggc ggg gag cgg ctg ctg cag ctg ggc cag ggc gac gag ctg tgc    15374
Leu Gly Gly Glu Arg Leu Leu Gln Leu Gly Gln Gly Asp Glu Leu Cys
    675                 680                 685
```

```
ggc cag gag gag gcc ttc cga ggc tgg gcc cag gct gcc ttc cag        15419
Gly Gln Glu Glu Ala Phe Arg Gly Trp Ala Gln Ala Ala Phe Gln
690                 695                 700

gtgagcccag cccagcccct gctctgactc ctgccccctg ggatgcctcc tcctgcctca  15479

ctctgccctg attctgtttg gttctttggt cccttcctgt tccttccaaa atccaccctc  15539

atctctccat ggcatagcca gctcttctgg gtcaggggca gaggatgaca tggccctgcc  15599

gaccacaggg gtgcctagcc caggcagaag tgcagccgaa agagagcagg cagggccctg  15659

gcaggaggga gcttcagcca ggcacaggct gggcctcaca agtgggcgca caaagggagg  15719

gggtgcaggg cagggcaggg gaccccaccc aggatgggca ggatggaggg agaaggaagg  15779

gacagagaga aggtcagaca gaggcaaggg ctgaagctga ggccagcaca gaagccacag  15839

gaagccagag gccagacagc ctggggcggt gcctgcaccg cagaactggt cccgggccgg  15899

gcaagcaagc acagggagag gtggatccct gggggctgtg gctttttaag cctgggcttc  15959

ctcaggggca gtgctgcctg tctggggatc atgtctgcag ttgacaaggg ctcggtctcc  16019

ccagtgccac actgttcagg gcagtgctgc tgtcccgggg cccaggctgg agctcagcag  16079

atttgccttg attggaggag gagggcatcc taggaggaga gggagtgggg gctacctcag  16139

ggacggggag gtcaggctgc agaaacacat aggccctgat tgggaagaag ggaacggaaa  16199

ataagactta aagaatttaa acaaaaagag ccattgcagc gggatgagac cacatcatca  16259

ggttttggga ataggacttt agaggcgtag gatccattac agcatcaccg aaccagaagc  16319

aggaaggctg agctaagcag agcagcagca gtggagatag gaaggaaggg agggaggggc  16379

cgaggaagga aggaagagat ataagacttc acacgcacca caaaagaaag attaacggga  16439

cttggtgata tgaggctcag ccaatcacgg gtgagccctg catttcaagc ctgggactgg  16499

cccagcagtt ttccagctgt gtgcctgacc aggagtagac gggatccaca ccctcccagg  16559

gatctgcccc gtggggtccc ctctgccgcc cgaattgtgc gtcccttccc aggagcactt  16619

actatctgca cgcactttgt ggaaagctaa gggctttaca taaagtatct catttaatct  16679

tcaccagaac acaatgaggt gtaaagatgg ggaaactgag gcatgtcact gtaagtacgg  16739

gattcggaat ttgaatgcag gtctgaacac acagacgcct tcacagagct accgtgtgcc  16799

aagcactatg cttctcggat cacgggatta acacgcacca gataaggaac gatgcaccaa  16859

tcaggacgtg cagagaaaga gccagccggg tccctgggcc cagcggccaa tccatgaaat  16919

gggctggcgg aaaaggtgct gtccttggcg ccggcctcag ccactggggc tgccaacccc  16979

ccaggagcaa gacgcagtga agccgcccag gcgcctcact agggcgaccc ctggtggcgg  17039

ggaggtcctc agccctcacc ggcctgtccc gcag gcc gcc tgt gag acc ttc tgt  17094
                                     Ala Ala Cys Glu Thr Phe Cys
                                     705                 710

gtg gga gag gat gcc aag gcc gcc gcc cga gac atc ttc agc ccc aaa    17142
Val Gly Glu Asp Ala Lys Ala Ala Ala Arg Asp Ile Phe Ser Pro Lys
            715                 720                 725

cgg agc tgg aag cgc cag agg tac cgg ctg agc gcc cag gcc gag ggc    17190
Arg Ser Trp Lys Arg Gln Arg Tyr Arg Leu Ser Ala Gln Ala Glu Gly
        730                 735                 740

ctg cag ttg ctg cca g gtgggccctg ccctcaccct aacccggctg gttctctgag  17246
Leu Gln Leu Leu Pro
    745

gcccccacac cccgggacta aagcactctg gggccaggcc ctgctcccta gctcaggctg  17306

cctcatttgc ccctccccgc ccccag gt  ctg atc cac gtg cac agg cgg aag   17358
                             Gly Leu Ile His Val His Arg Arg Lys
                                 750                 755
```

```
atg ttc cag gct aca atc cgc tca gtg gaa aac ctg caa agc agc aag    17406
Met Phe Gln Ala Thr Ile Arg Ser Val Glu Asn Leu Gln Ser Ser Lys
        760                 765                 770

tcc ac  gtgaggacga cggctttacc gccccccaac ccctgtcctg aacaccctga     17461
Ser Thr

ccctggaccc tcctcctccc acattctccc gcccccaccc ctctctgact ccccataagt  17521

gcccctctcc ccaccccccag g agg gcc acc atc ctg gtg cgc ctg gac acc   17572
                        Arg Ala Thr Ile Leu Val Arg Leu Asp Thr
                                        780                 785

gga ggc cag gag ggg ctg cag tac cag ccg ggg gac cac ata ggt gtc    17620
Gly Gly Gln Glu Gly Leu Gln Tyr Gln Pro Gly Asp His Ile Gly Val
                790                 795                 800

tgc ccg ccc aac cgg ccc ggc ctt gtg gag gcg ctg ctg agc cgc gtg    17668
Cys Pro Pro Asn Arg Pro Gly Leu Val Glu Ala Leu Leu Ser Arg Val
            805                 810                 815

gag gac ccg ccg gcg ccc act gag ccc gtg gca gta gag cag ctg gag    17716
Glu Asp Pro Pro Ala Pro Thr Glu Pro Val Ala Val Glu Gln Leu Glu
        820                 825                 830

aag ggc agc cct g gtgaggggca gcctgggaag caacagggca caccagcccc      17769
Lys Gly Ser Pro
    835

atgcccagcc ccaccccccgg ccccaggcct ccaggagctc aggacccgac ccaggggggtg  17829

gccacctcct ccacagctca gcaggcaggc tcagagctgg ctgtgctgcc cactgccggg  17889

ctggccttgt tgctggacca tccccacacc ctcaaatgca cccccaccaa aaggctgtcc  17949

cctccctctg ggctcctctc caaggctccc ctagcaatct agcttgctct ggagctggca  18009

ctggggctat ttgctgccac atcaatgcct gggctttatt taaaataagg gggtggagtc  18069

agaggcagag gagcccagac caacccagtc cggccagggg cccccgaaca atacactgag  18129

gctacctaga caggccgacc ccgctgctca agggcaggct ctctaacagt caccaaaaca  18189

caaacatcag cccaggtact gcagtcctgc tgggccctgt cctcagagct ccctgtgcac  18249

tatccccag gt  ggc cct ccc ccc ggc tgg gtg cgg gac ccc cgg ctg ccc   18299
          Gly Gly Pro Pro Pro Gly Trp Val Arg Asp Pro Arg Leu Pro
                  840                 845                 850

ccg tgc acg ctg cgc cag gct ctc acc ttc ttc ctg gac atc acc tcc    18347
Pro Cys Thr Leu Arg Gln Ala Leu Thr Phe Phe Leu Asp Ile Thr Ser
            855                 860                 865

cca ccc agc cct cag ctc ttg cgg ctg ctc agc acc ttg gca gaa gag    18395
Pro Pro Ser Pro Gln Leu Leu Arg Leu Leu Ser Thr Leu Ala Glu Glu
        870                 875                 880

ccc agg gaa cag cag gag ctg gag gcc ctc agc cag gttgggggcc         18441
Pro Arg Glu Gln Gln Glu Leu Glu Ala Leu Ser Gln
    885                 890                 895

accccaatga ggcacagggg ctagagagac gggatgagct ggggggaccc cagtggcagg  18501

aaacccccat gcaaagtccc ccctggactt tcttctcctg gctgacatgc actggtgctt  18561

taagacccag ctcctcaggg aggaattcat ggctggattc tccaggtctt agagaaaact  18621

ctattggcct gaactgagca gggagaaacc ctaaagaggc tcagtggggg aggggtcaag  18681

aagggaggtt actaggaagg gctatggggc ctccaaccca ctgcatcctg ccccgccag   18740

gat ccc cga cgc tac gag gag tgg aag tgg ttc cgc tgc ccc acg ctg    18788
Asp Pro Arg Arg Tyr Glu Glu Trp Lys Trp Phe Arg Cys Pro Thr Leu
                900                 905                 910

ctg gag gtg ctg gag cag ttc ccg tcg gtg gcg ctg cct gcc cca ctg    18836
Leu Glu Val Leu Glu Gln Phe Pro Ser Val Ala Leu Pro Ala Pro Leu
            915                 920                 925
```

-continued

```
ctc ctc acc cag ctg cct ctg ctc cag ccc cgg tac tac tca gtc agc    18884
Leu Leu Thr Gln Leu Pro Leu Leu Gln Pro Arg Tyr Tyr Ser Val Ser
        930                 935                 940

tcg gca ccc agc acc cac cca gga gag atc cac ctc act gta gct gtg    18932
Ser Ala Pro Ser Thr His Pro Gly Glu Ile His Leu Thr Val Ala Val
    945                 950                 955

ctg gca tac agg act cag g gtgaggcaac aagcaggagc aggcctggcc        18981
Leu Ala Tyr Arg Thr Gln
960                 965

acagcagggt tgggaccggc ccctctctgg cccctcaccg gcctctcctt cccaccccca  19041

g at  ggg ctg ggc ccc ctg cac tat gga gtc tgc tcc acg tgg cta agc  19089
  Asp Gly Leu Gly Pro Leu His Tyr Gly Val Cys Ser Thr Trp Leu Ser
                970                 975                 980

cag ctc aag ccc gga gac cct gtg ccc tgc ttc atc cgg gg             19130
Gln Leu Lys Pro Gly Asp Pro Val Pro Cys Phe Ile Arg Gly
            985                 990                 995

gtaagtgaga tggaggactt ggtggggagc tgcccagggt cagggtggca gctttggtga  19190

ggagtgtcac tggtgagggg tgtcactgga aacaggaagg agctctgtaa catgtcaagg  19250

gtgtggtgtc attaggtcac ttcagaactc tggctaagct ttggctctct cattcattta  19310

gactcagagt tctgccctga aactatagct cccagagcca gagctggtat caaaccggct  19370

ggccctgtgg ctttctgaaa gcttctgtgt tcctctctat gtccctgggc tgtctgatgt  19430

tgggcagcat ggcacctggg aactacagtc actaaatcct cactcaatcc agggagaact  19490

actagttagg gttaagacca ccctttggcc ttggtgtcac caaggactca aagaaggtga  19550

aggttttggt tttttttcc cccagagatg gagtcttgct ctgtcgccca ggctggagtg  19610

cagtggtacg atctcggctt actgcaacct ccgcctcccg ggttcaagag attctcctat  19670

ggcgtgaacc tgggaggtgg agcttgcagt gagccaagat tgtgccactg cactccagcc  19730

tgggcgacag agccagactc tgtctcaaaa aaaaaaaaaa aaatattctc ctgtctcagc  19790

ctcctgagta gctgggatta caggcaccca ccaccacgcc cagctaattt ttgtattttt  19850

agtagagacg gtgtttcact atgttggcca ggctggtctc gagctcctga cctcacaatc  19910

ctcccacctc cgcctcccaa agtcttggga ttacaggtgt gagccaccgc gcccggaccg  19970

agggtgaagg attttaagag acccttcctt catgctgtgt ccagaagtct tgcccgctct  20030

cgcagccagg aaccaaaagt cctggtagga ctgagaacag ttcctaggct gccatcagct  20090

gggcctggtg attcaaatcc acccaggtgg ctaaactaca aataaaccgt acccatctac  20150

tgaacataaa ctaaatacca ctattaagga tacttaaaat aaacacactt agtgaaccca  20210

ttatgaactg aaagtgtctt tcacccttcc cacgttttct aaatcccctg agtcatctaa  20270

gtattcttca atccaaaatg aactatattt cctttggtgc aatctccaga aaccacagat  20330

ccaaggagtt tcagcaagta gagttgtttt ttgtttttg ttttttttt aattttttt  20390

tgagatggga agaacttggg tcctccttgc tccacccacc ctgcatggtg agaatggtgg  20450

agcaggaaag gcaaagggga cctgatggag tgtctctcct gccag g gct ccc tcc    20505
                                                    Ala Pro Ser

ttc cgg  ctg cca ccc gat ccc  agc ttg ccc tgc atc  ctg gtg ggt     20550
Phe Arg  Leu Pro Pro Asp Pro  Ser Leu Pro Cys Ile  Leu Val Gly
    1000                1005                 1010

cca ggc  act ggc att gcc ccc  ttc cgg gga ttc tgg  cag gag cgg     20595
Pro Gly  Thr Gly Ile Ala Pro  Phe Arg Gly Phe Trp  Gln Glu Arg
    1015                1020                 1025

ctg cat  gac att gag agc aaa  g gtgaggctgg ggactaaagg actgcctgaa   20647
Leu His  Asp Ile Glu Ser Lys
    1030                1035
```

```
                                                        -continued

gggagtcaca caatctaggg acagaggggt ggggctggaa ggcaggaaat aggaaagaga    20707

gggcaggaaa caaagtccac aaagctgaaa agacgctcat gagaccaagg ggagggcagg    20767

taccaaaggc aagggctggg ccctgagctt ctggcttcct ggtgcctggt acatagtagg    20827

tgttgactgg attgaggaca aaggaaaata gaattttcaa agggattagg gctaagactc    20887

aaagaagaac tgcccaaggt ggattcttga ctgtgccaga gctgaccgag gtctgtccaa    20947

gacctaagga tgctacaagg tgttcatatt gagcatgggg tgcccagggt ggtctgtcaa    21007

tcaaaagaag agggctgtga ctgggaggag agttataagt atgggagaat atgaagtggg    21067

agcggggaag gggactgcga tgtcacacaa tgcaaagggc atggaattct gagtccgaag    21127

ccgcgcattc tagcgcagct ccaccagggg ccaccacctc acccgcgctt ccctt ccctc    21187

tgtaaatcag ggctgtgcag ggtctctgtg aaagcattct acactctctt agagatgaaa    21247

cagccaaagt aatggtggtt tcagcccaaa acgctgggct gccaggctgg gcgacggtgg    21307

cctgtgggga ggccccacta gcactgtgcc ccggagaaga gccttcccaa gcgcggggtt    21367

gcttgcag gg ctg cag ccc act ccc atg act ttg gtg ttc ggc tgc         21413
         Gly Leu Gln Pro Thr Pro Met Thr Leu Val Phe Gly Cys
             1040                1045

cga tgc tcc caa ctt gac cat ctc tac cgc gac gag gtg cag aac         21458
Arg Cys Ser Gln Leu Asp His Leu Tyr Arg Asp Glu Val Gln Asn
    1050                1055                1060

gcc cag cag cgc ggg gtg ttt ggc cga gtc ctc acc gcc ttc tcc         21503
Ala Gln Gln Arg Gly Val Phe Gly Arg Val Leu Thr Ala Phe Ser
    1065                1070                1075

cgg gaa cct gac aac ccc aag gtgtgagacc ctgagggcgc aatggtaacc         21554
Arg Glu Pro Asp Asn Pro Lys
    1080                1085

tgaagatagg gagagagggg aggactcgcg ctctccagcg gggcacacca accacggccc    21614

tcccgtggcc tcccacgacc actcagccac ccctgcacac tctggcccac ccttgtgccc    21674

cggcccctct aggcccgcct cctcccgccc ctgccccgcc cctttggctc tgcccctgtt    21734

gacaccgccc cagggcacgc aggccccacc aggcccgctc cggagacttt cacgtccagg    21794

gccagccagc agccccgggc tgcgcccccg cgcccacccc caccagggcc cgccctaacc    21854

ccgccgcccc gcag acc tac gtg cag gac atc ctg agg acg gag ctg gct    21904
             Thr Tyr Val Gln Asp Ile Leu Arg Thr Glu Leu Ala
                             1090                1095

gcg gag gtg cac cgc gtg ctg tgc ctc gag cgg ggc cac atg ttt         21949
Ala Glu Val His Arg Val Leu Cys Leu Glu Arg Gly His Met Phe
    1100                1105                1110

gtc tgc ggc gat gtt acc atg gca acc aac gtc ctg cag acc gtg         21994
Val Cys Gly Asp Val Thr Met Ala Thr Asn Val Leu Gln Thr Val
    1115                1120                1125

cag cgc atc ctg gcg acg gag ggc gac atg gag ctg gac gag gcc         22039
Gln Arg Ile Leu Ala Thr Glu Gly Asp Met Glu Leu Asp Glu Ala
    1130                1135                1140

ggc gac gtc atc ggc gtg ctg cgg gtgcggaggg gcgggccggg               22083
Gly Asp Val Ile Gly Val Leu Arg
    1145                1150

cctgagcgtg cggggttcct gctaaggtct ccgagtcggg ttctgatcca ctgtgctctt    22143

ttccgacag gat cag caa cgc tac cac gaa gac att ttc ggg ctc acg      22191
          Asp Gln Gln Arg Tyr His Glu Asp Ile Phe Gly Leu Thr
              1155                1160

ctg cgc acc cag gag gtg aca agc cgc ata cgc acc cag agc ttt         22236
Leu Arg Thr Gln Glu Val Thr Ser Arg Ile Arg Thr Gln Ser Phe
    1165                1170                1175
```

```
tcc ttg  cag gag cgt cag ttg  cgg ggc gca gtg ccc  tgg gcg ttc     22281
Ser Leu  Gln Glu Arg Gln Leu  Arg Gly Ala Val Pro  Trp Ala Phe
    1180                 1185                 1190

gac cct  ccc ggc tca gac acc  aac agc ccc tgagagccgc ctggctttcc    22331
Asp Pro  Pro Gly Ser Asp Thr  Asn Ser Pro
    1195                 1200

cttccagttc cgggagagcg gctgcccgac tcaggtccgc ccgaccagga tcagccccgc  22391

tcctcccctc ttgaggtggt gccttctcac atctgtccag aggctgcaag gattcagcat  22451

tattcctcca ggaaggagca aaacgcctct tttccctctc taggcctgtt gcctcgggcc  22511

tgggtccgcc ttaatctgga aggcccctcc cagcagcggt accccagggc ctactgccac  22571

ccgcttcctg tttcttagtc gaatgttaga ttcctcttgc ctctctcagg agtatcttac  22631

ctgtaaagtc taatctctaa atcaagtatt tattattgaa gatttaccat aagggactgt  22691

gccagatgtt aggagaacta ctaaagtgcc taccccagct catgtggatt acagtttttt  22751

tttttgtttt tttttttttt gaaacggagt ctccctctgc cgcccgggct ggagtgcagt  22811

ggcgtgatct cagctcactg caacctccac cccacaagtt caagtgattc tcctgcctca  22871

gcctccccaag tagttgggat tacaggtgcc tgccaccgcg cccggctagg ttttgtattt  22931

ttagtaaaga cggggtttca ccatcttggc caggctggtc ttgaactcct gacctcgtga  22991

tccaaccgcc tcagcctccc aaagtgctgg gattacaggt gtgagctact gcacccggcg  23051

tggattacaa ttataaaatg acaagatttc tgttttaacc tgtgcagttg tgggtatgtg  23111

gtggggaaag gggtcattct tttgacagag tcctacacgc cacttgaccc tgcactctga  23171

aaacatggtt tccagccagt ctgggctgct cccccgtgca gttctcaggc tcgtgatcga  23231

gaaggcaggt gcagcactca gctgccagga gtggggcctg ccagaaacaa gagtcacaga  23291

gatgtgcaac agccatgagc aagctttact gcttatttca tacaggatgg ggagccacac  23351

ccacttcctg ggacatcaca cccgtactga agtccaaaaa catcatccct cccgtctttc  23411

cactgacaag tccccatccc ctacaagccc caaggaacct gaaagtgctg ctggcagccg  23471

ccagcatgac gaatccacag ccttaaagcc cacctgcctc actgtcgccc ttccatttag  23531

ctcggcctca tccttgacct ctgtccccca ccttgaggaa actcgaggac ttcttcccag  23591

gcagctgctc caggacacat tccagttggg gatgtctccc cttattccct ctgggtgcag  23651

accatctcta agacttgttt ccagatgcca tcagcatctc ctctccttgc ctacctttttc  23711

tctgttctcg gggcgagttc ctcactgact cccaggtcct gcccaactaa agcacctggg  23771

cctgtcatct atggggcctc taacaatgac tccttgtgtt tttctactcc accctccaat  23831

ctcctgtggc tgccgaagcc agggtacctg tgggaggaga cggctcttgg caagcagtcc  23891

aggggtctag attccagaga tgaccacctc ccatcacccc aaattcccac cactgctccc  23951

atcgcttcaa gtcggactcc aaaccaacta cctatgccgt cctttctccc tcccctcaca  24011

ggaggcaata ctgaccctga ggagtcgtct cagtcagtgc aagaggcccg gtcaggctcc  24071

ttctgggtgt ctgtggtcac ctgaaaccct ccggggaaca gattccgggc cttctgggtt  24131

ccccactgtt gtctggggct agaggcagga ctggagcctg gtgaaaaagg ccatcagctg  24191

ggcagttcca tgatgcccag tgtccaccag gctctgtccc ctgcaggccc caccctcctc  24251

accgtcactt gaccaggatg gcttctcctc atcaggcgag ggtggctgtg aggggctgga  24311

gcagggcctg gacaggatgg aggctgcagc ctcaccccac ggctcctgct gctgctgctg  24371

ctggtgaagc tgcatggaaa ggaggaggaa tgagggctgc accccaagga gggcagggcc  24431

aagcacctgg gctagaggca gagggctttt cagcctcctc ctgccactct gctagaccct  24491
```

```
tccgtagact ccaccccacc tcagtctcca tgttgttcac ctgccttctc tccacatttc  24551

tcctttgggc acccctctac tcacctggtg caggtagatg acatggagac tcatctcggc  24611

agaagcaagt tctgggagct gggccagctt ctggccccca gtgcctcctg ggacacacaga  24671

gctggaacat aacatgaagc aggtcaaaag tcatgccctc ctcccgccac accccagagg  24731

actccccttc tgaatccccc ctcagcgccc cagctcccca ctcctacagg atcagcccac  24791

ccccctccac atgcccctgc atctcagcct ccactcctca cctggggtcc tgggcaattc  24851

gggaaatgga ggcaaggagg ctggctgtgg ccgcagctgg acagggggct gtcgggctca  24911

gatctctcgg aggcaggaga gggtgcacga agaggttggc caggaaggcc tcaggctggg  24971

tgcaagagga gagggaaagc caaagaggga gtcagaagag aggacagaaa cggagtaggg  25031

aggaagcaga ggcctaaaga aggcaggaga gcaggctggg ggcgggggct ggtgaggcag  25091

gttactacct aaggt                                                   25106
```

<210> SEQ ID NO 2
<211> LENGTH: 1203
<212> TYPE: PRT
<213> ORGANISM: Homo sapiens

<400> SEQUENCE: 2

```
Met Gly Asn Leu Lys Ser Val Ala Gln Glu Pro Gly Pro Pro Cys Gly
1               5                   10                  15

Leu Gly Leu Gly Leu Gly Leu Gly Leu Cys Gly Lys Gln Gly Pro Ala
            20                  25                  30

Thr Pro Ala Pro Glu Pro Ser Arg Ala Pro Ala Ser Leu Leu Pro Pro
        35                  40                  45

Ala Pro Glu His Ser Pro Pro Ser Ser Pro Leu Thr Gln Pro Pro Glu
    50                  55                  60

Gly Pro Lys Phe Pro Arg Val Lys Asn Trp Glu Val Gly Ser Ile Thr
65                  70                  75                  80

Tyr Asp Thr Leu Ser Ala Gln Ala Gln Gln Asp Gly Pro Cys Thr Pro
                85                  90                  95

Arg Arg Cys Leu Gly Ser Leu Val Phe Pro Arg Lys Leu Gln Gly Arg
            100                 105                 110

Pro Ser Pro Gly Pro Pro Ala Pro Glu Gln Leu Leu Ser Gln Ala Arg
        115                 120                 125

Asp Phe Ile Asn Gln Tyr Tyr Ser Ser Ile Lys Arg Ser Gly Ser Gln
    130                 135                 140

Ala His Glu Gln Arg Leu Gln Glu Val Glu Ala Glu Val Ala Ala Thr
145                 150                 155                 160

Gly Thr Tyr Gln Leu Arg Glu Ser Glu Leu Val Phe Gly Ala Lys Gln
                165                 170                 175

Ala Trp Arg Asn Ala Pro Arg Cys Val Gly Arg Ile Gln Trp Gly Lys
            180                 185                 190

Leu Gln Val Phe Asp Ala Arg Asp Cys Arg Ser Ala Gln Glu Met Phe
        195                 200                 205

Thr Tyr Ile Cys Asn His Ile Lys Tyr Ala Thr Asn Arg Gly Asn Leu
    210                 215                 220

Arg Ser Ala Ile Thr Val Phe Pro Gln Arg Cys Pro Gly Arg Gly Asp
225                 230                 235                 240

Phe Arg Ile Trp Asn Ser Gln Leu Val Arg Tyr Ala Gly Tyr Arg Gln
                245                 250                 255

Gln Asp Gly Ser Val Arg Gly Asp Pro Ala Asn Val Glu Ile Thr Glu
```

-continued

```
            260                 265                 270

Leu Cys Ile Gln His Gly Trp Thr Pro Gly Asn Gly Arg Phe Asp Val
        275                 280                 285

Leu Pro Leu Leu Leu Gln Ala Pro Asp Glu Pro Pro Glu Leu Phe Leu
    290                 295                 300

Leu Pro Pro Glu Leu Val Leu Glu Val Pro Leu Glu His Pro Thr Leu
305                 310                 315                 320

Glu Trp Phe Ala Ala Leu Gly Leu Arg Trp Tyr Ala Leu Pro Ala Val
                325                 330                 335

Ser Asn Met Leu Leu Glu Ile Gly Gly Leu Glu Phe Pro Ala Ala Pro
            340                 345                 350

Phe Ser Gly Trp Tyr Met Ser Thr Glu Ile Gly Thr Arg Asn Leu Cys
        355                 360                 365

Asp Pro His Arg Tyr Asn Ile Leu Glu Asp Val Ala Val Cys Met Asp
    370                 375                 380

Leu Asp Thr Arg Thr Thr Ser Ser Leu Trp Lys Asp Lys Ala Ala Val
385                 390                 395                 400

Glu Ile Asn Val Ala Val Leu His Ser Tyr Gln Leu Ala Lys Val Thr
                405                 410                 415

Ile Val Asp His His Ala Ala Thr Ala Ser Phe Met Lys His Leu Glu
            420                 425                 430

Asn Glu Gln Lys Ala Arg Gly Gly Cys Pro Ala Asp Trp Ala Trp Ile
        435                 440                 445

Val Pro Pro Ile Ser Gly Ser Leu Thr Pro Val Phe His Gln Glu Met
    450                 455                 460

Val Asn Tyr Phe Leu Ser Pro Ala Phe Arg Tyr Gln Pro Asp Pro Trp
465                 470                 475                 480

Lys Gly Ser Ala Ala Lys Gly Thr Gly Ile Thr Arg Lys Lys Thr Phe
                485                 490                 495

Lys Glu Val Ala Asn Ala Val Lys Ile Ser Ala Ser Leu Met Gly Thr
            500                 505                 510

Val Met Ala Lys Arg Val Lys Ala Thr Ile Leu Tyr Gly Ser Glu Thr
        515                 520                 525

Gly Arg Ala Gln Ser Tyr Ala Gln Gln Leu Gly Arg Leu Phe Arg Lys
    530                 535                 540

Ala Phe Asp Pro Arg Val Leu Cys Met Asp Glu Tyr Asp Val Val Ser
545                 550                 555                 560

Leu Glu His Glu Thr Leu Val Leu Val Val Thr Ser Thr Phe Gly Asn
                565                 570                 575

Gly Asp Pro Pro Glu Asn Gly Glu Ser Phe Ala Ala Ala Leu Met Glu
            580                 585                 590

Met Ser Gly Pro Tyr Asn Ser Ser Pro Arg Pro Glu Gln His Lys Ser
        595                 600                 605

Tyr Lys Ile Arg Phe Asn Ser Ile Ser Cys Ser Asp Pro Leu Val Ser
    610                 615                 620

Ser Trp Arg Arg Lys Arg Lys Glu Ser Ser Asn Thr Asp Ser Ala Gly
625                 630                 635                 640

Ala Leu Gly Thr Leu Arg Phe Cys Val Phe Gly Leu Gly Ser Arg Ala
                645                 650                 655

Tyr Pro His Phe Cys Ala Phe Ala Arg Ala Val Asp Thr Arg Leu Glu
            660                 665                 670

Glu Leu Gly Gly Glu Arg Leu Leu Gln Leu Gly Gln Gly Asp Glu Leu
        675                 680                 685
```

-continued

```
Cys Gly Gln Glu Glu Ala Phe Arg Gly Trp Ala Gln Ala Ala Phe Gln
    690                 695                 700

Ala Ala Cys Glu Thr Phe Cys Val Gly Glu Asp Ala Lys Ala Ala Ala
705                 710                 715                 720

Arg Asp Ile Phe Ser Pro Lys Arg Ser Trp Lys Arg Gln Arg Tyr Arg
                725                 730                 735

Leu Ser Ala Gln Ala Glu Gly Leu Gln Leu Leu Pro Gly Leu Ile His
            740                 745                 750

Val His Arg Arg Lys Met Phe Gln Ala Thr Ile Arg Ser Val Glu Asn
        755                 760                 765

Leu Gln Ser Ser Lys Ser Thr Arg Ala Thr Ile Leu Val Arg Leu Asp
    770                 775                 780

Thr Gly Gly Gln Glu Gly Leu Gln Tyr Gln Pro Gly Asp His Ile Gly
785                 790                 795                 800

Val Cys Pro Pro Asn Arg Pro Gly Leu Val Glu Ala Leu Leu Ser Arg
                805                 810                 815

Val Glu Asp Pro Pro Ala Pro Thr Glu Pro Val Ala Val Glu Gln Leu
            820                 825                 830

Glu Lys Gly Ser Pro Gly Gly Pro Pro Pro Gly Trp Val Arg Asp Pro
        835                 840                 845

Arg Leu Pro Pro Cys Thr Leu Arg Gln Ala Leu Thr Phe Phe Leu Asp
    850                 855                 860

Ile Thr Ser Pro Pro Ser Pro Gln Leu Leu Arg Leu Leu Ser Thr Leu
865                 870                 875                 880

Ala Glu Glu Pro Arg Glu Gln Gln Glu Leu Glu Ala Leu Ser Gln Asp
                885                 890                 895

Pro Arg Arg Tyr Glu Glu Trp Lys Trp Phe Arg Cys Pro Thr Leu Leu
            900                 905                 910

Glu Val Leu Glu Gln Phe Pro Ser Val Ala Leu Pro Ala Pro Leu Leu
        915                 920                 925

Leu Thr Gln Leu Pro Leu Leu Gln Pro Arg Tyr Tyr Ser Val Ser Ser
    930                 935                 940

Ala Pro Ser Thr His Pro Gly Glu Ile His Leu Thr Val Ala Val Leu
945                 950                 955                 960

Ala Tyr Arg Thr Gln Asp Gly Leu Gly Pro Leu His Tyr Gly Val Cys
                965                 970                 975

Ser Thr Trp Leu Ser Gln Leu Lys Pro Gly Asp Pro Val Pro Cys Phe
            980                 985                 990

Ile Arg Gly Ala Pro Ser Phe Arg  Leu Pro Pro Asp Pro  Ser Leu Pro
        995                 1000                1005

Cys Ile  Leu Val Gly Pro Gly  Thr Gly Ile Ala Pro  Phe Arg Gly
    1010                1015                1020

Phe Trp  Gln Glu Arg Leu His  Asp Ile Glu Ser Lys  Gly Leu Gln
    1025                1030                1035

Pro Thr  Pro Met Thr Leu Val  Phe Gly Cys Arg Cys  Ser Gln Leu
    1040                1045                1050

Asp His  Leu Tyr Arg Asp Glu  Val Gln Asn Ala Gln  Gln Arg Gly
    1055                1060                1065

Val Phe  Gly Arg Val Leu Thr  Ala Phe Ser Arg Glu  Pro Asp Asn
    1070                1075                1080

Pro Lys  Thr Tyr Val Gln Asp  Ile Leu Arg Thr Glu  Leu Ala Ala
    1085                1090                1095

Glu Val  His Arg Val Leu Cys  Leu Glu Arg Gly His  Met Phe Val
    1100                1105                1110
```

```
Cys Gly  Asp Val Thr Met Ala  Thr Asn Val Leu Gln  Thr Val Gln
    1115                 1120                 1125

Arg Ile  Leu Ala Thr Glu Gly  Asp Met Glu Leu Asp  Glu Ala Gly
    1130                 1135                 1140

Asp Val  Ile Gly Val Leu Arg  Asp Gln Gln Arg Tyr  His Glu Asp
    1145                 1150                 1155

Ile Phe  Gly Leu Thr Leu Arg  Thr Gln Glu Val Thr  Ser Arg Ile
    1160                 1165                 1170

Arg Thr  Gln Ser Phe Ser Leu  Gln Glu Arg Gln Leu  Arg Gly Ala
    1175                 1180                 1185

Val Pro  Trp Ala Phe Asp Pro  Pro Gly Ser Asp Thr  Asn Ser Pro
    1190                 1195                 1200
```

```
<210> SEQ ID NO 3
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 3

gcatgcactc tggcctgaag t                                                21


<210> SEQ ID NO 4
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 4

caggaagctg ccttccagtg c                                                21


<210> SEQ ID NO 5
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 5

ctggagatga aggcaggaga c                                                21


<210> SEQ ID NO 6
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 6

ctccatccca cccagtcaat c                                                21


<210> SEQ ID NO 7
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 7

agggtcagcc a                                                           11
```

-continued

```
<210> SEQ ID NO 8
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 8

gggtcagccg                                                           10


<210> SEQ ID NO 9
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 9

gccagggaag agcttgatgc cctggtggga gc                                  32


<210> SEQ ID NO 10
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 10

gttctggggg c                                                         11


<210> SEQ ID NO 11
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 11

agttctgggg ga                                                        12


<210> SEQ ID NO 12
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 12

tcatctgggg cctgcagcag caggggcagc a                                   31
```